United States Patent
McClelland et al.

(10) Patent No.: US 9,829,499 B2
(45) Date of Patent: Nov. 28, 2017

(54) METHOD AND RELATED SYSTEMS FOR USE WITH A FLUIDICS DEVICE

(71) Applicant: SciKon Innovation, Inc., Chapel Hill, NC (US)

(72) Inventors: Randall Edwin McClelland, Chapel Hill, NC (US); David J. Sloan, Apex, NC (US); Timothy C. Jensen, Cary, NC (US); Maureen Kay Bunger, Morrisville, NC (US)

(73) Assignee: SciKon Innovation, Inc., Research Triangle Park, NC (US)

( * ) Notice: Subject to any disclaimer, the term of this patent is extended or adjusted under 35 U.S.C. 154(b) by 0 days.

(21) Appl. No.: 15/361,415

(22) Filed: Nov. 26, 2016

(65) Prior Publication Data

US 2017/0102404 A1   Apr. 13, 2017

Related U.S. Application Data

(63) Continuation of application No. PCT/US2016/023844, filed on Mar. 23, 2016.

(60) Provisional application No. 62/136,911, filed on Mar. 23, 2015, provisional application No. 62/308,207, filed on Mar. 14, 2016.

(51) Int. Cl.
    *G01N 33/50*    (2006.01)
    *G01N 35/10*    (2006.01)
    *B01L 3/00*     (2006.01)

(52) U.S. Cl.
    CPC ........ *G01N 35/1074* (2013.01); *B01L 3/5025* (2013.01); *G01N 33/5008* (2013.01); *B01L 2200/0694* (2013.01); *B01L 2300/0829* (2013.01); *B01L 2400/0457* (2013.01)

(58) Field of Classification Search
    CPC ....... B01L 2300/123; B01L 2400/0481; B01L 2400/0655; B01L 3/502738; B01L 2200/10; B01L 2300/0681; B01L 3/50273; B01L 3/502746; B01L 2200/0605; B01L 2200/027; B01L 2200/025; B01L 2300/0861; B01L 2300/14; B01L 2200/0694; B01L 2300/0829; B01L 2400/0457; B01L 3/5025; G01N 33/5008; G01N 35/1074
    See application file for complete search history.

(56) References Cited

U.S. PATENT DOCUMENTS

| | | |
|---|---|---|
| D246,466 S | 11/1977 | Attree et al. |
| 4,239,853 A | 12/1980 | Bradley |
| D264,810 S | 6/1982 | Voltmann |
| D271,239 S | 11/1983 | Lemieux et al. |
| 4,483,925 A | 11/1984 | Noack |
| D284,699 S | 7/1986 | Jolley |
| D288,484 S | 2/1987 | Mitchell |
| D302,207 S | 7/1989 | Matkovich |
| D303,149 S | 8/1989 | Andersen |
| 5,130,105 A | 7/1992 | Carter et al. |
| D335,348 S | 5/1993 | Frenkel et al. |
| 5,417,923 A | 5/1995 | Bojanic et al. |
| 5,487,872 A | 1/1996 | Hafeman et al. |
| 5,588,441 A | 12/1996 | Fishman |
| 5,801,055 A | 9/1998 | Henderson |
| 5,817,510 A | 10/1998 | Pandey et al. |
| D404,497 S | 1/1999 | Lahm et al. |
| D411,308 S | 6/1999 | Pandey et al. |
| 5,993,745 A | 11/1999 | Laska |
| D420,743 S | 2/2000 | Monks |
| 6,019,225 A | 2/2000 | Kalmakis et al. |
| 6,106,783 A | 8/2000 | Gamble |
| 6,395,234 B1 | 5/2002 | Hunnell et al. |
| 6,439,884 B1 | 8/2002 | Cronin |
| 6,485,690 B1 | 11/2002 | Pfost et al. |
| D469,544 S | 1/2003 | Lafond et al. |
| 6,632,656 B1 | 10/2003 | Thomas et al. |
| 6,637,463 B1 | 10/2003 | Lei et al. |
| 6,875,405 B1 | 4/2005 | Mathus et al. |
| 6,939,709 B2 | 9/2005 | Henderson et al. |
| 6,987,253 B2 | 1/2006 | Bedingham et al. |
| 7,005,029 B2 | 2/2006 | Khan et al. |
| 7,279,134 B2 | 10/2007 | Chan et al. |
| D574,505 S | 8/2008 | Muller-Cohn et al. |
| 7,452,510 B2 | 11/2008 | Weinfield et al. |
| 7,560,073 B1 | 7/2009 | Peters et al. |
| D632,803 S | 2/2011 | Motadel et al. |
| 7,922,672 B2 | 4/2011 | Hein, Jr. et al. |

(Continued)

FOREIGN PATENT DOCUMENTS

| | | |
|---|---|---|
| GB | 2147100 A | 5/1985 |
| WO | WO2011137039 A1 | 11/2011 |

OTHER PUBLICATIONS

U.S. Notice of Allowance for U.S. Appl. No. 14/016,913, dated Dec. 22, 2016.
U.S. Final Rejection for U.S. Appl. No. 14/016,913, dated Nov. 16, 2016.
U.S. Notice of Allowance for Design U.S. Appl. No. 29/465,155, dated May 4, 2016.

(Continued)

*Primary Examiner* — Debbie K Ware
(74) *Attorney, Agent, or Firm* — NK Patent Law, PLLC

(57) ABSTRACT

Disclosed are fluidics devices and assemblies allowing for fluid flow between a plurality of wells. The fluidics devices and assemblies that are provided mimic in vivo tissue environments by allowing for initially segregated tissue cultures that can then be linked through fluid flow to measure integrated tissue response. The fluidics devices and assemblies provide a pumpless system using surface tension, gravity, and channel geometries. By linking human tissue functional systems to better simulate in vivo feedback and response signals between the tissues, the need for testing in animals can be minimized.

20 Claims, 43 Drawing Sheets

(56) References Cited

U.S. PATENT DOCUMENTS

| | | |
|---|---|---|
| D672,053 S | 12/2012 | Chen et al. |
| 8,377,685 B2 | 2/2013 | Meyvantsson et al. |
| D699,370 S | 2/2014 | Motadel et al. |
| D699,859 S | 2/2014 | Motadel |
| D720,468 S | 12/2014 | Calderwood et al. |
| D724,236 S | 3/2015 | Motadel et al. |
| D730,537 S | 5/2015 | Burroughs et al. |
| 2003/0138941 A1 | 7/2003 | Gong et al. |
| 2004/0101439 A1 | 5/2004 | Fusco et al. |
| 2005/0072030 A1 | 4/2005 | Wu |
| 2005/0147958 A1 | 7/2005 | Hassanein et al. |
| 2006/0093530 A1 | 5/2006 | Ueda |
| 2006/0137434 A1 | 6/2006 | Cohen et al. |
| 2007/0166816 A1 | 7/2007 | Campbell et al. |
| 2008/0060424 A1 | 3/2008 | Babic et al. |
| 2009/0023610 A1 | 1/2009 | Peytavi |
| 2010/0041143 A1 | 2/2010 | Nishiyama et al. |
| 2010/0233694 A1 | 9/2010 | Kopf-Sill |
| 2010/0284859 A1 | 11/2010 | Cooney et al. |
| 2011/0236278 A1 | 9/2011 | Motadel et al. |
| 2012/0135452 A1 | 5/2012 | Shuler et al. |
| 2012/0328488 A1 | 12/2012 | Puntambekar et al. |

OTHER PUBLICATIONS

U.S. Non-Final Rejection for U.S. Appl. No. 14/016,913, dated May 13, 2016.

Inamdar NK; Borenstein JT.; Microfluidic cell culture models for tissue engineering, Current Opinion in Biotechnology, 2011, 22, 1-9.

Domanksy K.; Inman W.; Serdy J.; Dash A.; Lim M.; Griffith L.; Perfused multiwell plate for 3D liver tissue engineering, Lab Chip, 2010, 10, 51-58.

Dance A, Enter the Third Dimension, Cell culture goes 3-D with devices that better mimic in vivo conditions, The Scientist, Sep. 1, 2012.

Keenan T & Folch A, Biomolecular gradients in cell culture systems, Lab Chip, 2008, 8, 34-57.

ISA/KR, International Search Report and Written Opinion for PCT Patent Application No. PCT/US2016/023844, dated Jul. 25, 2016.

Toh, Yi-Chin et al., "A microfluidic 3D hepatocyte chip for drug toxicity testing", Lab on a Chip, 2009, vol. 9, No. 14, pp. 2026-2035.

Ye, Nannan et al., "Cell-based high content screening using an integrated microfluidic device", Lab on a Chip, 2007, vol. 7, No. 12, pp. 1696-1704.

Kim, Jeongyun et al., "A programmable microfluidic cell array for combinatorial drug screening", Lab on a Chip, 2012, vol. 12, No. 10, pp. 1813-1822.

| Well | Z-Height optimized (um) |
|---|---|
| 3 | 20858 |
| 4 | 20545 |
| 5 | 20545 |
| 6 | 20544 |
| 7 | 20231 |
| 8 | 19918 |
| 9 | 19918 |
| 10 | 19605 |
| 11 | 19605 |

Figure 32

| | Source | Regula tor | 3 | 4 | 5 | 6 | 7 | 8 | 9 | 10 | 11 | Syphon |
|---|---|---|---|---|---|---|---|---|---|---|---|---|
| A | 1uM Fluorescein | | Acellular Wells (no metabolism) | | | | | | | | | |
| B | | | | | | | | | | | | |
| C | Vehicle Control | | HepG2 cells, 30000 cells/well | | | | | | | | | |
| D | | | | | | | | | | | | |
| E | | | | | | | | | | | | |
| F | Treated (150uM Tamoxifen or 50mM APAP) | | HepG2 cells, 30000 cells/well | | | | | | | | | |
| G | | | | | | | | | | | | |
| H | | | | | | | | | | | | |

Figure 34

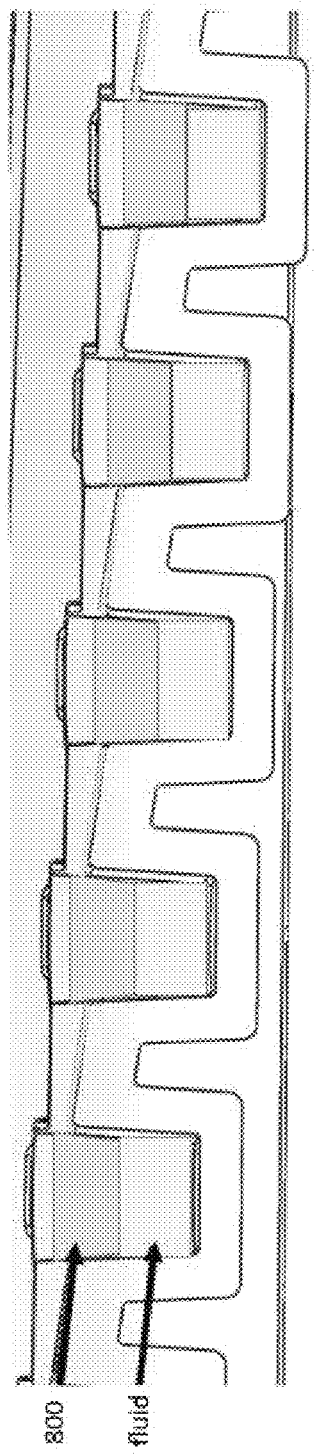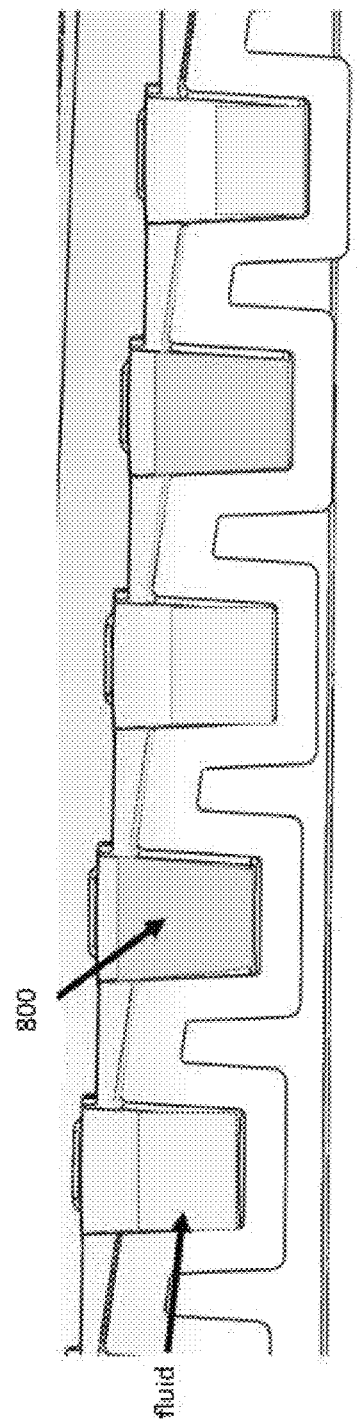
Figure 43
Figure 44

METHOD AND RELATED SYSTEMS FOR USE WITH A FLUIDICS DEVICE

CROSS REFERENCE TO RELATED APPLICATIONS

This application is a continuation of International Application No. PCT/US2016/023844 filed Mar. 23, 2016, which claims the benefit of U.S. Provisional Application No. 62/136,911 filed Mar. 23, 2015 and claims the benefit of U.S. Provisional Application No. 62/308,207 filed Mar. 14, 2016, each of which are incorporated by reference herein in their entirety.

TECHNICAL FIELD

This disclosure is related to a method and related systems for use with a fluidics device for providing a dosing fluid thereto and allowing fluid flow between a plurality of wells.

BACKGROUND

It is estimated to cost on the order of $1B dollars to bring a drug candidate to market and the pharmaceutical industry is enhancing its chances of success by investing in human pre-clinical research. This money has driven the absorption, distribution, metabolism, elimination, and toxicology (AD-MET) market in human-based products to a $5 billion dollar annual industry. The current technology for testing drug candidates is based on homogeneous culture techniques and animal models. Thus, there is an unmet need for biotool devices capable of linking human tissue functional systems to better simulate in vivo feedback and response signals between tissues and to minimize testing in animals. See Amit S. Kalgutkar's publication "Role of Bioactivation in Idiosyncratic Drug Toxicity: Structure-Toxicity Relationships" found in Advances in Bioactivation Research, edited by A. A. Elfarra (2008), which is incorporated herein by reference in its entirety.

This application is related to the subject matter of U.S. Provisional Application 62/086,623 filed Dec. 2, 2014, U.S. Provisional Application 61/697,395 filed Sep. 6, 2012, U.S. application Ser. No. 14/016,913 filed Sep. 3, 2013, and U.S. application Ser. No. 14/954,546 filed Nov. 30, 2015, each of which is incorporated by reference herein in its entirety. In some of the embodiments described in these applications, media is syphoned across wells of a fluidics device containing cell cultures through interconnecting capillaries.

Current in vitro biochemical assays used in evaluating cellular responses to drugs, toxicants, and other environmental stressors are dominated by traditional static well culture technologies. These assays may include a variety of live or dead cell enzyme assays that require the ability to isolate individual wells. The present invention enables fluidic devices having media flowing between adjacent downstream wells to effectively pause fluidic flow so as to prevent contamination from one well to an adjacent well so that measurements can be made. Further, the present invention permits fluid flow to be restarted once measurements are completed while sustaining gradients of chemical, toxicant, or cell metabolism. Additionally, the present invention provides methods for determining whether a parameter was diminished or enhanced by a cell culture response to a test compound.

Accordingly, fluidics devices and assemblies and their methods of use are provided in the present disclosure.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Disclosed herein is an in vitro assay method for determining whether a parameter was diminished or enhanced by a cell culture response to a test compound, comprising: applying a dynamic fluid including the test compound to a dynamic dosing well of a fluidics device, wherein the fluidics device includes a plurality of dynamic wells each containing a cell culture therein positioned downstream from the dynamic dosing well and in fluid communication therewith; applying a static fluid including the test compound to a static well; performing a dynamic bioassay to measure a parameter of at least one of the plurality of wells and determining a dynamic value; performing a static bioassay to measure the parameter of the static well and determining a static value; and comparing the dynamic value to the static value for determining whether the parameter was diminished or enhanced by the cell culture response to the test compound.

Disclosed herein is an in vitro assay method for determining whether a parameter was diminished or enhanced by a cell culture response to a test compound, comprising: applying a dynamic fluid including the test compound to a dynamic dosing well of a fluidics device, wherein the fluidics device includes a plurality of dynamic wells each containing a cell culture therein positioned downstream from the dynamic dosing well and in fluid communication therewith; applying a control fluid not including the test compound to a control dosing well of the fluidics device, wherein the fluidics device further includes a plurality of control wells each containing a cell culture therein positioned downstream from the control dosing well and in fluid communication therewith; performing a dynamic bioassay to measure the parameter of at least one of the plurality of dynamic wells and determining a dynamic value; performing a control bioassay to measure the parameter of at least one of the plurality of control wells and determining a control value; and comparing the dynamic value to the control value for determining whether the parameter was diminished or enhanced by the cell culture response to the test compound.

Disclosed herein is an in vitro assay method for determining whether a parameter was diminished or enhanced by a cell culture response to a test compound, comprising: applying a dynamic fluid having a first concentration of a test compound to a dynamic dosing well of a fluidics device, wherein the fluidics device includes a plurality of dynamic wells each containing a cell culture therein positioned downstream from the dynamic dosing well and in fluid communication therewith; performing a dynamic bioassay to measure the parameter of at least two of the plurality of dynamic wells and determining a first dynamic value and a second dynamic value; and comparing the first dynamic value to the second dynamic value for determining whether the parameter was diminished or enhanced by the cell culture response to the test compound.

According to one or more embodiments, the dynamic value includes a dynamic effective concentration at a percentage X (ECx) for the parameter, wherein $0 \leq X \leq 100$; the static value includes a static ECx for the parameter; and a lower value of the at least one dynamic ECx relative to the static ECx is predictive of the cell culture response to the test compound enhancing the parameter and a higher value of the at least one dynamic ECx relative to the static ECx is predictive of the cell culture response to the test compound diminishing the parameter.

According to one or more embodiments, the dynamic value includes a dynamic effective concentration at a percentage X (ECx) for the parameter, wherein $0 \leq X \leq 100$; the control value includes a control ECx for the parameter; and a lower value of the at least one dynamic ECx relative to the control ECx is predictive of the cell culture response to the test compound enhancing the parameter and a higher value of the at least one dynamic ECx relative to the control ECx is predictive of the cell culture response to the test compound diminishing the parameter.

According to one or more embodiments, X is 50 and the cell culture response and/or the parameter is cytotoxicity.

According to one or more embodiments, the test compound comprises one or more of a drug, a legal or illegal drug, a toxin, an agent of warfare, a tracing compound, a fragrance, a food spice, an oil, a gas, a metabolite, a compound, a hormone, a solution, a solute, a composite, a nutraceutical, a nutrient media, differentiation media, or a growth media with varying dissolved oxygen levels.

According to one or more embodiments, the effect is one or more of a cell culture response (as described herein), pharmacokinetics, drug metabolism, toxicity, cell receptor response, cell feedback signals, cell growth, cytotoxicity, cell differentiation, or cell regeneration.

According to one or more embodiments, the cell culture comprises one or more of: a tumor cell line; primary hepatocytes; stem cells; progenitor cells; differentiated products of stem cells; primary cells or tissues from liver, kidney, lung, heart, muscle, brain, pancreas or thyroid; a HepG2 cell line culture; a HepaRG cell line culture; or a cell culture derived directly from human, dog, non-human primate, mouse or rat tissue cultured in 2-dimensional or 3-dimensional formats.

According to one or more embodiments, the cell culture response comprises one or more of a pharmacokinetic response, a pharmodynamic response, metabolism of the test compound, metabolism of a fluidic component, cytotoxicity, cell receptor response, cell feedback signals, cell growth, cell differentiation, or cell regeneration.

According to one or more embodiments, the parameter comprises one or more of metabolism byproducts, toxicity, cell receptor responses, cell feedback signals, cell growth, cytotoxicity, cell differentiation, cell regeneration concentration, radiation, optical qualities, fluorescence, luminescence, presence of chemical constituents, presence of antigen constituents, colorimetrics, image or visualization qualities, electrical properties, magnetic properties, or light absorbance.

According to one or more embodiments, the method further comprises removing a portion of the dynamic fluid from at least one stop well, the stop well being one of the plurality of dynamic wells; and applying a liquid stop to the at least one stop well for controlling the flow of the dynamic fluid in preparation for the dynamic bioassay.

According to one or more embodiments, the method further comprises removing the dynamic fluid from at least one stop well, the stop well being one of the plurality of dynamic wells; and applying a liquid stop to fill the at least one stop well for controlling the flow of the dynamic fluid in preparation for the dynamic bioassay.

According to one or more embodiments, the method further comprises providing a physical stop selectively engageable with at least one of the plurality of dynamic wells; and engaging the physical stop with the at least one of the plurality of dynamic wells for controlling the flow of the dynamic fluid therefrom in preparation for the dynamic bioassay.

According to one or more embodiments, the performing of any one or more of the bioassays includes removing an aliquot of the respective fluid from the respective well at one or more time periods.

According to one or more embodiments, the applying of the dynamic fluid and/or the control fluid is repeated using a specific volume at determined intervals over a specified period of time.

According to one or more embodiments, the applying of the dynamic fluid and/or the control fluid is performed automatically by a robotic liquid handling apparatus or by using a piston assembly nestably engaged with the fluidics device.

According to one or more embodiments, the method further comprises syphoning the respective fluid from the downstream well furthest from the respective dosing well when the applying of the dynamic fluid and/or the control fluid is repeated.

According to one or more embodiments, the syphoning the respective fluid is performed automatically by a robotic liquid handling apparatus.

According to one or more embodiments, the method further comprises applying a tracing fluid having a known concentration of a detectable tracing compound to a tracing dosing well of the fluidics device, wherein the fluidics device further includes a plurality of tracing wells each containing a cell culture therein positioned downstream from the tracing dosing well and in fluid communication therewith; and determining the concentration of the tracing compound as a standard curve to calculate a concentration of the test compound in each of the plurality of dynamic wells.

According to one or more embodiments, an effect detection reagent is present in the plurality of dynamic wells having a cell culture therein, and wherein determination of the dynamic ECx includes detection of the effect detection reagent.

According to one or more embodiments, removing the fluid from at least one stop well is performed using a pipette, a wick, a vacuum or a syphon.

According to one or more embodiments, the dynamic fluid, static fluid and/or control fluid is a gas.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings:

FIG. 32 is a table showing the determined optimal Z-height focus.

FIG. 34 depicts the experimental plate configuration.

FIG. 43 depicts a liquid plug intra-well method according to one or more embodiments of the present invention.

FIG. 44 depicts a liquid plug inter-well method according to one or more embodiments of the present invention.

DETAILED DESCRIPTION

Figure 1:
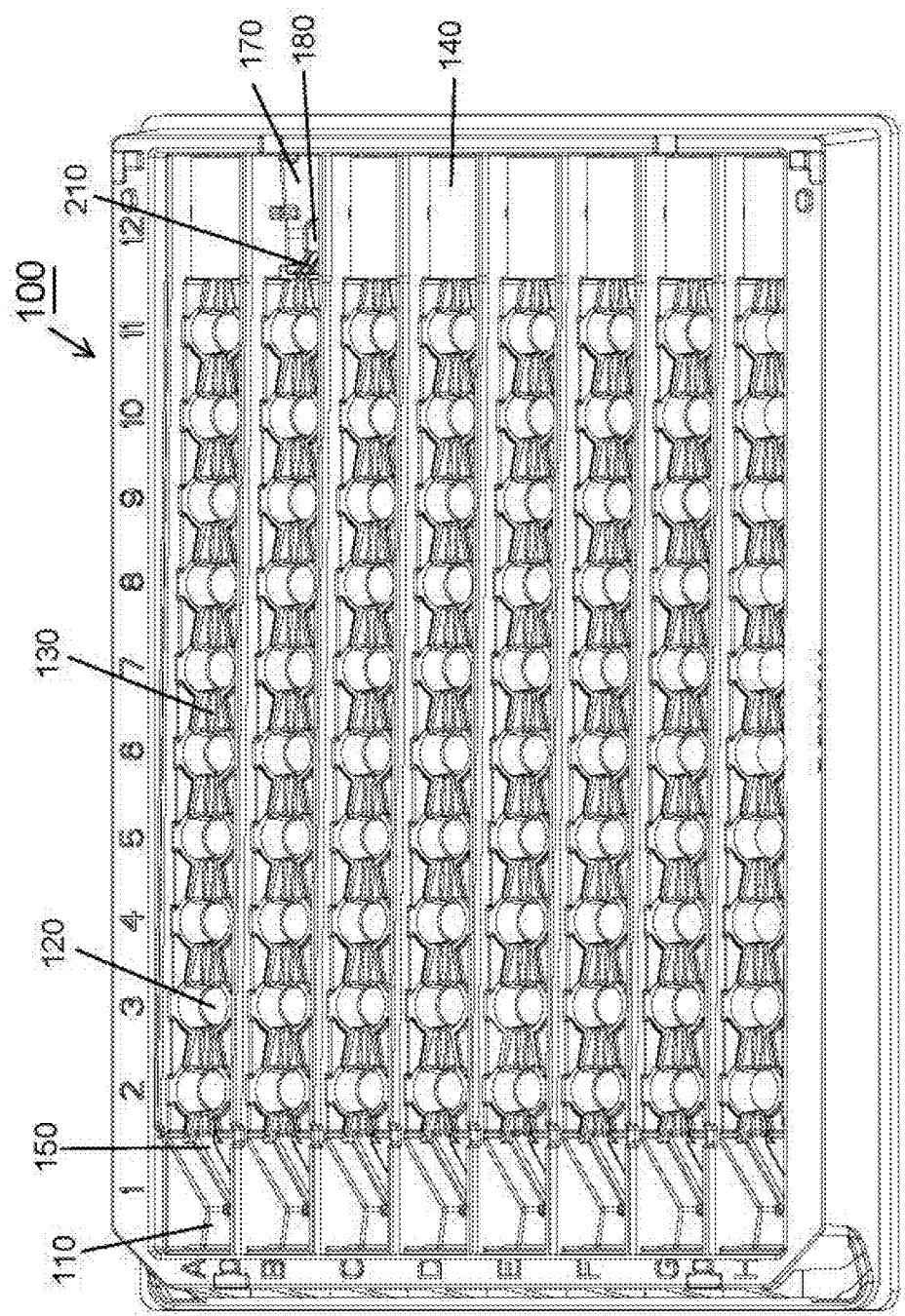
FIG. 1 is a perspective view of a fluidics device in accordance with embodiments of the present disclosure.

The presently disclosed subject matter provides fluidics devices and assemblies that in one aspect are capable of linking human functional systems to better simulate in vivo feedback and response signals between tissues and to minimize the need for testing in animal models. For example, the devices and assemblies of the presently disclosed subject matter can mimic in vivo tissue environments by allowing for initially segregated tissue cultures that can then be linked through fluid flow to measure integrated tissue response. The devices and assemblies of the present disclosure can allow for cell culture integration and media flow activated on demand. The devices and assemblies of the presently disclosed subject matter can provide a pumpless system using surface tension, gravity, and channel geometries. The devices and assemblies of the present disclosure can provide timed and tempered nutrient flow through integrated channels. The devices and assemblies of the present disclosure can provide an option to induce toxin exposure (e.g., drug exposure) at a particular cell site.

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies.

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

FIG. 1 is a perspective view of a fluidics device 100 in accordance with embodiments of the present disclosure. The fluidics device 100 can include a dosing well 110 positioned upstream from a plurality of wells 120 for containing a respective host fluid, and one or more channels 130 extending between adjacent upstream and downstream wells 120 to define a fluid flow channel 130 there between such that a dosing fluid 1 deposited into the dosing well 110 flows to the respective host fluid of the adjacent downstream well 120 along the fluid flow channel 130 there between, and the respective host fluid subsequently flows to each adjacent downstream well 120 along the fluid flow channel 130 there between.

According to one or more embodiments, the fluidics device 100 can have a structure such that each adjacent downstream well 120 is oriented in a step-down position relative to its adjacent upstream well 120. An example of a fluidics device 100 having this step-down well positioning structure is shown in FIG. 1.

According to one or more embodiments, the fluidics device 100 can include a wick 140 downstream from at least a portion of the plurality of wells 120. The wick 140 is in fluid contact with the fluid flow channel 130 for regulating fluid flow through the plurality of wells 120. For purposes of the specification and claims, the term "wick" is meant to be used in the broadest sense to refer to a piece of material that can convey liquid by capillary action.

According to one or more embodiments, the fluidics device 100 can include a dosing well channel 150 extending from a bottom of the dosing well 110 to the fluid flow channel 130 such that the dosing fluid 1 flows to the respective host fluid of the adjacent downstream well 120 through the dosing well channel 150 and along the fluid flow channel 130. A side of the dosing well 110 can define an angle of greater than 90° extending from a bottom of the dosing well 110 up to the fluid flow channel 130 of the adjacent well 120. According to one or more embodiments, the fluidics device 100 can include a collection well 170 downstream from the plurality of wells 120 to collect the respective host fluid after having flowed through the plurality of wells 120. The collection well 170 of the fluidics device 100 can include a floor that defines a divot 180, wherein the floor is angled such that the divot 180 is defined at a lower portion of the floor. In certain embodiments according to the present disclosure as described herein below, the lower portion of the floor of the collection well 170 can define an aperture as an alternative to the divot 180. In another example, the divot 180 can be converted to an aperture for use of the fluidics device 100 in an assembly as described herein below.

In accordance with embodiments of the present disclosure, the collection well 170 of fluidics device 100 can include one or more collection well channels 210 extending from the fluid flow channel 130 to a bottom of the collection well 170 such that the respective host fluid of the adjacent upstream well 120 flows along the fluid flow channel 130 and through the collection well channel 210 into the collection well 170. The collection well channel 210 can have a width ranging from about 10 to 3500 microns and a depth ranging from about 10 to 3500 microns. The collection well 170 can define a ramp extending from a bottom of the collection well 170 up to the fluid flow channel 130 of the adjacent upstream well 120. The ramp can include 1, 2, 3 or 4 of the collection well channels 210 that are contiguous with the ramp.

Figure 2:
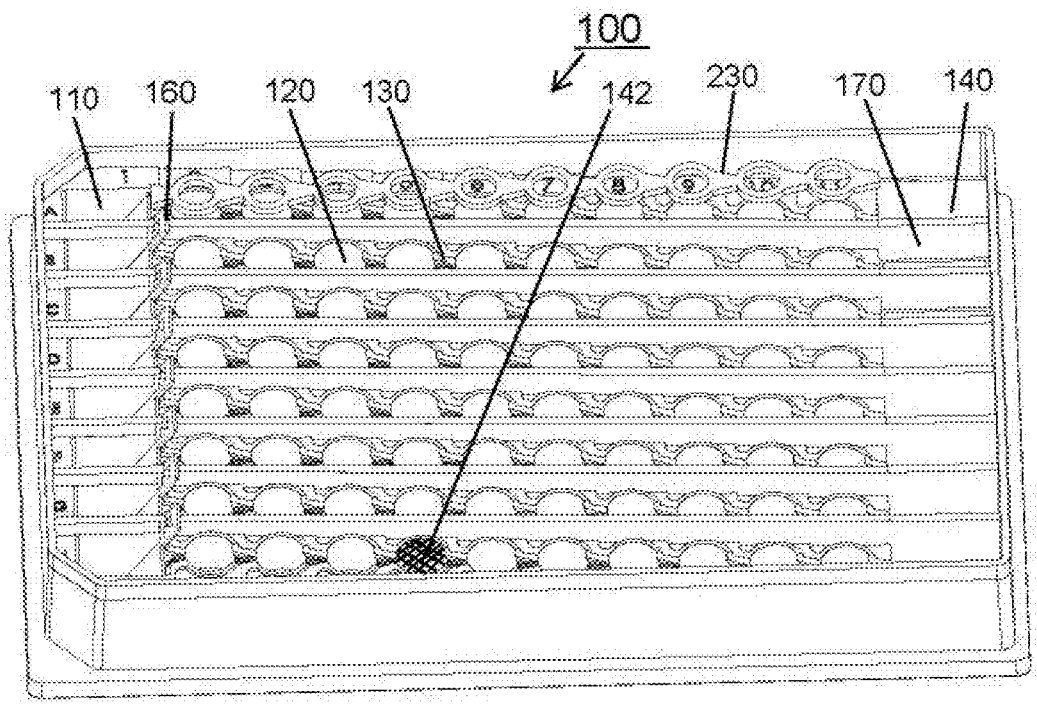
FIG. 2 is a perspective view of the fluidics device of FIG. 1 illustrating dosing well channel cover to enclose dosing well channel and channel cover to enclose the one or more channels extending between the adjacent wells in accordance with embodiments of the present disclosure.
Figure 41:
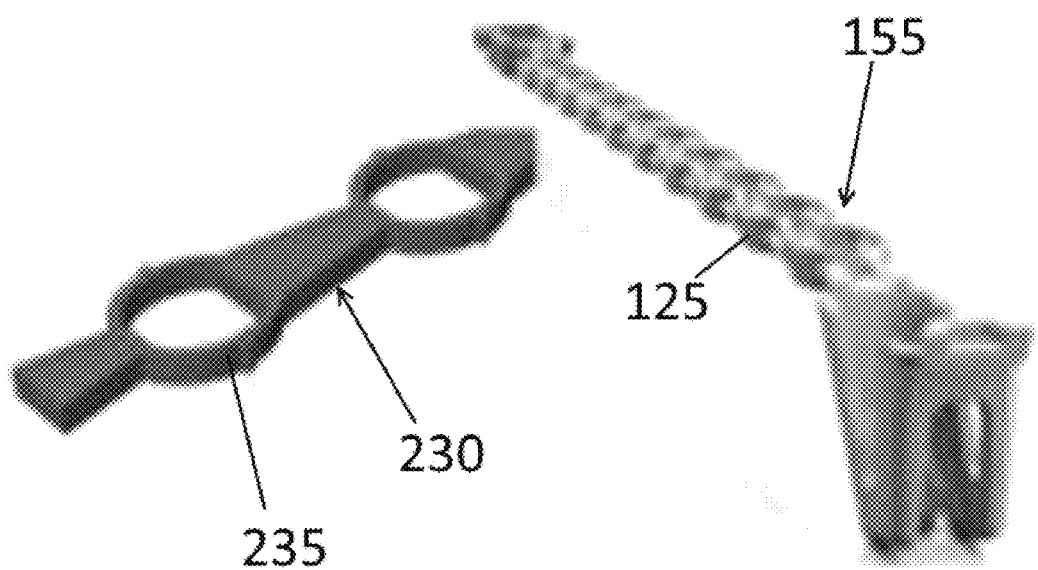
FIG. 41 depicts a channel cover and well row according to one or more embodiments of the present invention.

FIG. 2 is a perspective view of the fluidics device 100 in accordance with embodiments of the present disclosure. FIG. 2 illustrates that the fluidics device 100 can include a dosing well channel cover 160 configured to enclose the dosing well channel 150. An example of the dosing well channel cover 160 is shown in FIG. 2 where each of the 8 dosing wells (A-H) are covered with the dosing well channel cover 160. FIGS. 2 and 41 also illustrate that the fluidics device 100 can include a channel cover 230 configured for engagement on top of the one or more channels 130 extending between the adjacent wells 120 to enclose the channels 130.

The wick of the present disclosure can define any shape that is suitable for being in fluid contact with the fluid flow channel 130 and for regulating fluid flow through the plurality of wells 120. For example, the wick of the presently disclosed subject matter can be any absorbent material. The wick can regulate fluid flow through the plurality of wells 120 at a rate ranging from 0.0007 ml/min to 30 ml/min. In one example, the respective host fluid after having flowed through each of the plurality of wells 120 and onto the wick can evaporate off the wick.

Figure 3A:
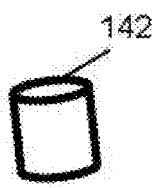
FIGS. 3A-3C illustrate the wick separate from the fluidics device of FIG. 2 in accordance with embodiments of the present disclosure.
Figure 3B:
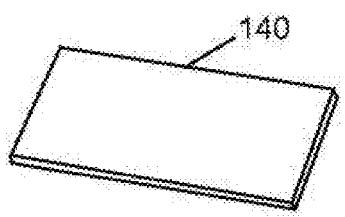
Figure 3C:
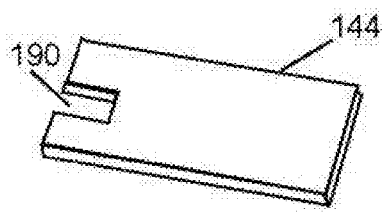

FIG. 2 illustrates two examples of the wick (i.e., wick 140 and wick 142) at separate positions downstream from a portion of the plurality of wells 120. FIGS. 3A-3C illustrate the wick in accordance with one or more embodiments of the present disclosure. FIG. 3A illustrates an example of the wick 142 having a cylindrical shape. FIG. 3C illustrates an example of the wick 140 defining a generally flat shape. The wick defining a generally flat shape can define a gap such that only a portion of an edge of the wick is in fluid contact with the fluid flow channel 130. FIG. 3C illustrates an example of the wick 144 defining a gap 190.

The wick 142 defining a cylindrical shape is illustrated in FIG. 2 and FIG. 3A. The wick of the present disclosure can be positioned anywhere downstream from at least a portion of the plurality of wells 120. For example, the wick 142 defining a cylindrical shape is shown contained in well 120 in row eight of the fluidics device 100 in FIG. 2 such that the wick 142 is in fluid contact with the fluid flow channel 130 for regulating fluid flow through the plurality of upstream wells 120.

The wick can define a generally flat shape. According to one or more embodiments, the wick 140 or 144 defining a generally flat shape can be contained in the collection well 170 such that the wick 140 or 144 is in fluid contact with the fluid flow channel 130 for regulating fluid flow through the plurality of wells 120. The wick defining a generally flat shape can be carried by a shoulder defined by the collection well 170 such that the wick does not contact a bottom surface of the collection well 170. An example of the wick 140 defining a generally flat shape and carried by a shoulder defined by the collection well 170 is illustrated in FIG. 2 and in FIG. 3B. The wick defining a generally flat shape can be carried by one or more posts defined by the collection well 170 such that the wick does not contact a bottom surface of the collection well 170. In one embodiment, the wick can define a generally flat shape and can be carried by six of the posts defined by the collection well 170 such that the wick does not contact a bottom surface of the collection well 170.

Figure 4:
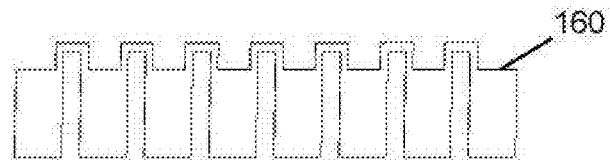
FIG. 4 illustrates the dosing well channel cover separate from the fluidics device of FIG. 2 in accordance with embodiments of the present disclosure.

FIG. 4 illustrates the dosing well channel cover 160 separate from the fluidics device 100.

Figure 5:
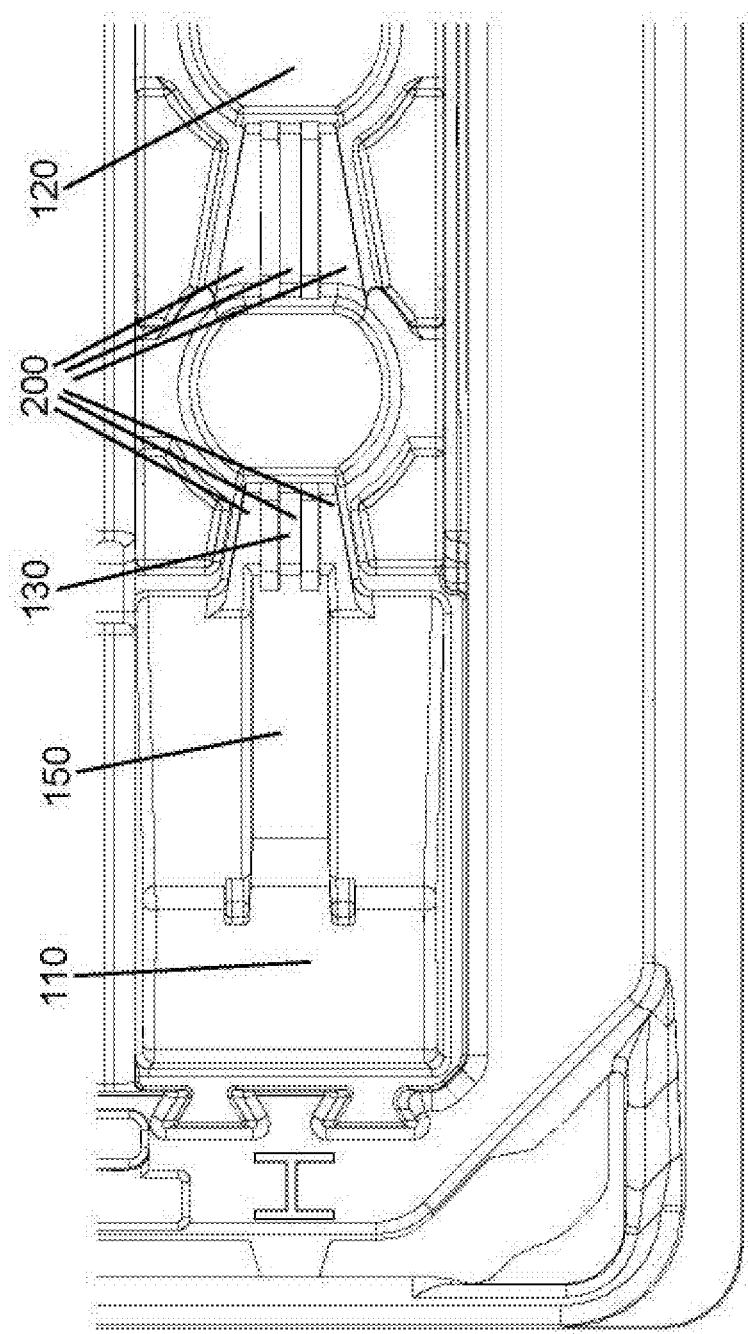
FIG. 5 illustrates an enlarged top view of the fluidics device of FIG. 1 showing an enlarged view of the dosing well, dosing well channel, adjacent downstream well, and the one or more channels extending there between in accordance with embodiments of the present disclosure.

FIG. 5 illustrates a top view of the fluidics device of FIG. 1 showing an enlarged view of the dosing well 110, dosing well channel 150, adjacent downstream well 120, and the one or more channels 130 extending there between in accordance with embodiments of the present disclosure. The dosing well channel 150 can have a width ranging from about 10 to 3500 microns and a depth ranging from about 10 to 3500 microns. The dosing well channel 150 can include 2, 3 or 4 channels contiguous with the dosing well channel 150 and each of the channels can have a width ranging from about 200 to 1500 microns and a depth ranging from about 10 to 1500 microns.

The one or more channels 130 extending between adjacent upstream and downstream wells 120 of the fluidics device 100 can have a width ranging from 10 to 3500 microns and a depth of 10 to 1500 microns. An example of a fluidics device 100 having a single channel 130 is shown in FIG. 5. The channel 130 can define a triangular-shape that extends between each of the adjacent wells 120. The triangular-shape channel 130 can be positioned such that the triangular shape generally converges at each adjacent downstream well 120. An example of a fluidics device 100 having the triangular-shape channel 130 positioned such that the triangular shape generally converges at each adjacent downstream well 120 is shown in FIG. 5.

The fluidics device 100 can have 2, 3 or 4 channels 130 and each of the channels 130 can have a width ranging from 200 to 750 microns and a depth ranging from 10 to 1500 microns. The fluidics device 100 can include 2, 3 or 4 microchannels 200 that are contiguous with the channel 130 and each of the microchannels 200 can have a width ranging from 200 to 750 microns and a depth ranging from 10 to 1500 microns. An example of a fluidics device 100 having 3 microchannels 200 that are contiguous with the triangular-shape channel 130 is shown in FIG. 5.

The channel cover 230 can include 1 or more projections extending from the channel cover 230 such that when the channel cover 230 is engaged on top of the channels 130 of the fluidics device 100 the channel cover 230 defines 2 or more microchannels 200 contiguous with the channel 130. For example, the channel cover 230 can have two projections such that when the channel cover 230 is engaged on top of the channel 130 of the fluidics device 100 the channel cover 230 defines 3 microchannels 200 contiguous with the channel 130. In one embodiment, each of the microchannels 200 defined by the channel cover 230 can have a width ranging from 200 to 750 microns and a depth ranging from 10 to 1500 microns.

The bottom surface of each of the channels 130, the dosing well channel 150, the microchannels 200, and the collection well channels 210 can define different shapes. For example, the channels 130, the dosing well channel 150, the microchannels 200, and the collection well channels 210 can define an arcuate bottom surface or a generally flat bottom surface.

Figure 8:
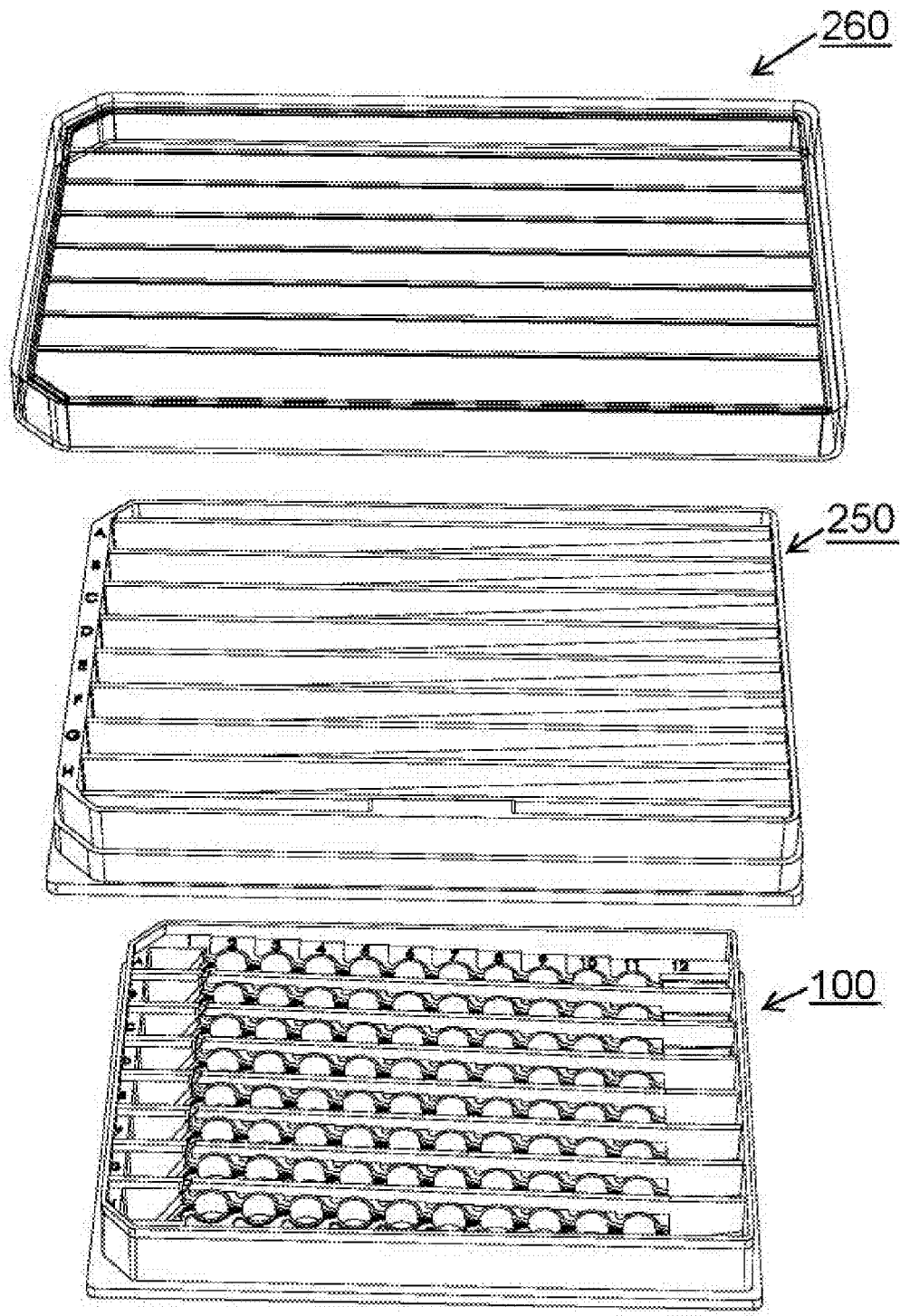
FIG. 8 shows an exploded perspective view of the fluidics device of FIG. 1 as part of an assembly including a reservoir tray nestably engaged on top of the fluidics device and a cover tray nestably engaged on top of the reservoir tray in accordance with embodiments of the present disclosure.

According to one or more embodiments, the fluidics device 100 can have a structure where the plurality of wells 120 are aligned in a row. The fluidics device 100 can have 12 wells in a respective row and a total of 8 rows. An example of a fluidics device 100 having this structure is shown in FIGS. 1, 2, and 8. The fluidics device 100 can have 3 wells in a row and a total of 2 rows. The fluidics device 100 can have 6 wells in a row and a total of 4 rows. The fluidics device 100 can have 8 wells in a row and a total of 6 rows. The fluidics device 100 can have 12 wells in a row and a total of 8 rows. The fluidics device 100 can have 24 wells in a row and a total of 16 rows. The fluidics device 100 can have 48 wells in a row and a total of 32 rows.

According to one or more embodiments, the fluidics device 100 can have a structure where the plurality of wells 120 for containing a respective host fluid are oriented in a configuration such that each downstream well 120 is positioned lower relative to each adjacent upstream well 120 and the dosing well 110 is upstream from the plurality of wells 120 and in fluid communication therewith.

The fluidics device 100 of the presently disclosed subject matter can be employed for any use requiring the tempered flow of fluid between a plurality of wells. According to one or more embodiments, a method for employing the fluidics device 100 includes adding a dosing fluid 1 to the dosing well 110 and adding the respective host fluid to the plurality of wells 120 such that the fluid is in fluid contact with the fluid flow channel 130, whereby the dosing fluid 1 flows to each of the respective host fluids in the plurality of wells 120 in a tempered manner. The method can include removing an aliquot of the respective host fluid from the wells 120 at one or more time periods to measure the effect of the dosing fluid 1 being tempered through the plurality of wells 120 over time.

The dosing fluid 1 can include, for example, but is not limited to a drug, a legal or illegal drug, a toxin, an agent of warfare, a fragrance, a food spice, an oil, a gas, a metabolite, a compound, a hormone, a solution, a solute, a composite, a nutrient media, differentiation media, or a growth media, and combinations thereof. The plurality of wells 120 can contain a respective cell culture whereby an effect or parameter or response of the tempered exposure to the dosing fluid 1 on the cells can be measured. The effect or parameter or response of the tempered exposure to the dosing fluid 1 on the cell cultures to be measured can be one or more of pharmacokinetics, drug metabolism, toxicity, pre-clinical pharmaceutical studies, cell response, cell receptor response, cell feedback signals, cell growth, cell death, cell differentiation, or cell regeneration, and combinations thereof. The respective cell culture can be, for example, a stem cell culture or a progenitor cell culture.

According to one or more embodiments, the plurality of wells 120 of the fluidics device 100 can contain a respective cell culture, and a method for employing the fluidics device 100 containing the respective cell cultures includes adding a dosing fluid 1 to the dosing well 110, adding the desired respective host fluid to the wells 120 such that the fluid is in fluid contact with the fluid flow channel 130. Subsequently, the dosing fluid 1 flows to each of the respective host fluids in the plurality of wells 120 in a tempered manner. The method can further include removing an aliquot of the respective host fluid from the wells 120 at one or more time periods to measure the effect or parameter or response of the dosing fluid 1 on the cells.

The fluidics device 100 can be made of any material that is suitable for use in fluid transfer between the plurality of wells 120. The type of material chosen can depend on the desired use of the fluidics device 100. For example, the user of the fluidics device 100 can choose the material based on the dosing well fluid that will be used and the expected interaction of the dosing well fluid with the material. Thus, the fluidics device 100 can be made of any suitable material including, for example, a polymer, a synthetic polymer, a TOPAS® COC polymer, a biodegradable polymer, a plastic, a biodegradable plastic, a thermoplastic, a polystyrene, a polyethylene, a polypropylene, a polyvinyl chloride, a polytetrafluoroethylene, a silicone, a glass, a PYREX, or a borosilicate, or combinations thereof. In addition, the dosing well channel cover 160, the channel cover 230, and the wick 140, 142, 144 may each be made from the same materials as the fluidics device 100. In one example, a user may wish to have each of the fluidics device 100, the dosing well channel cover 160, the channel cover 230, and the wick 140, 142, 144 made from the same material such that the interaction of the dosing well fluid with the material does not vary.

According to one or more embodiments, the surface of one or more of the plurality of wells 120 of the fluidics device 100 can be modified with one or both of a chemical layer or a protein layer to support a cell culture. The protein layer for supporting the cell cultures can include one or more of collagen I, collagen II, collagen III, laminin, or fibronectin, or combinations thereof.

Figure 6:
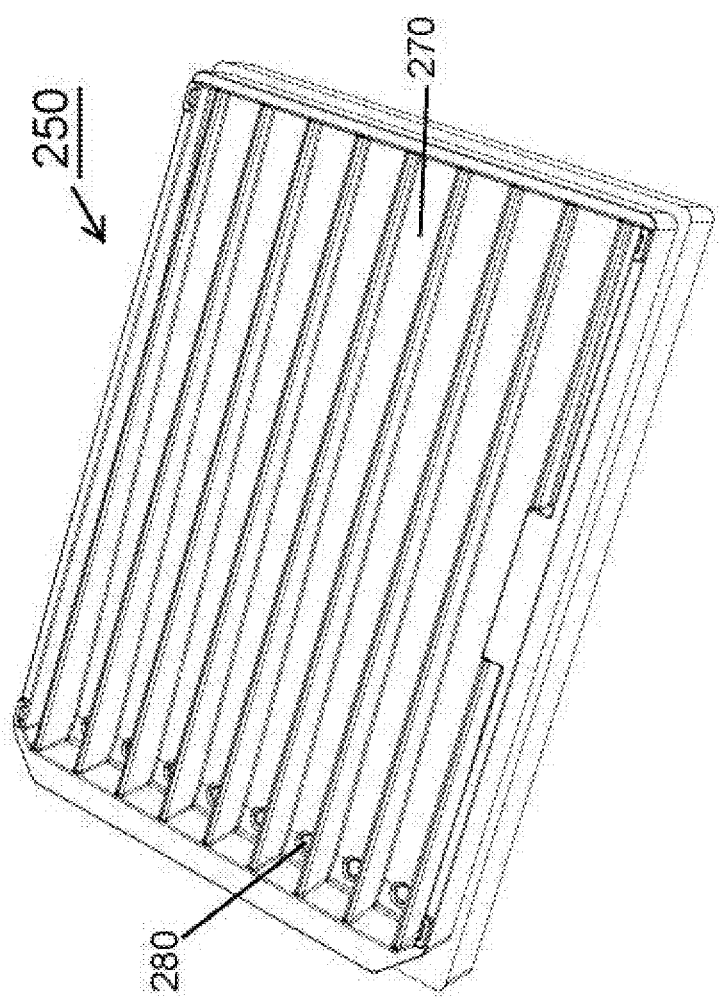
FIG. 6 shows a perspective view of the reservoir tray in accordance with embodiments of the present disclosure
Figure 7:
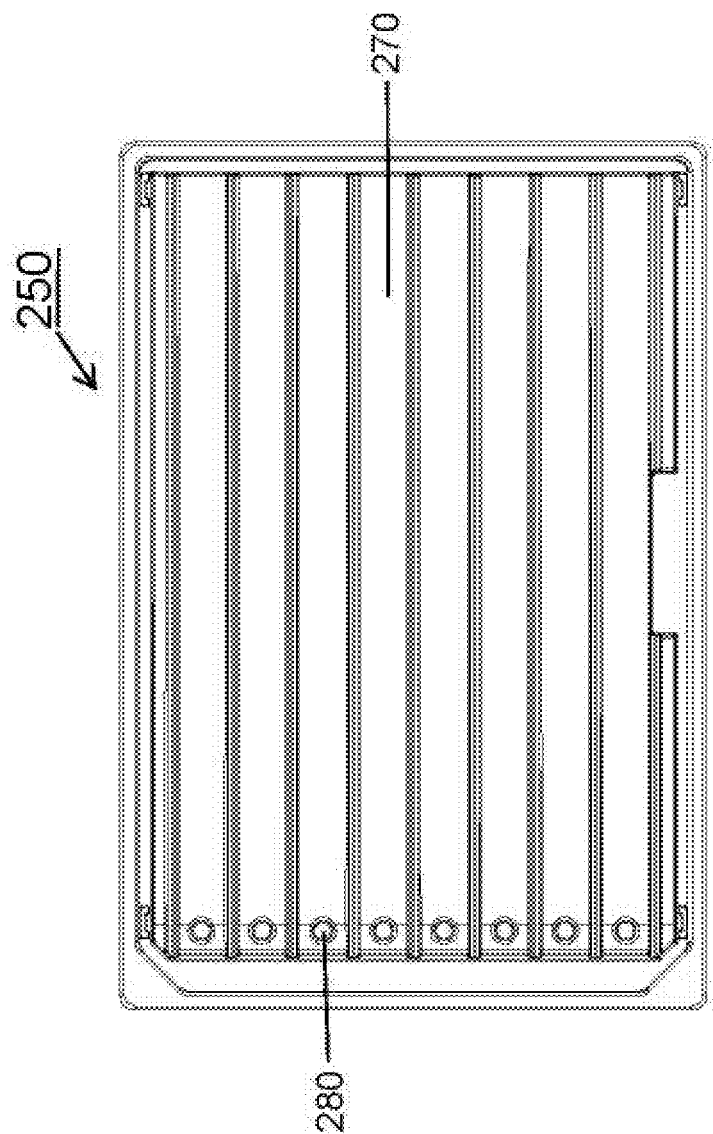
FIG. 7 shows a bottom view of the reservoir tray in accordance with embodiments of the present disclosure.

According to one or more embodiments of the presently disclosed subject matter, an assembly is provided for allowing fluid flow between the plurality of wells 120 of the fluidics device 100. The assembly can include the fluidics device 100 and a reservoir tray 250 configured for nesting engagement on top of the fluidics device 100. FIG. 6 shows a perspective view of the reservoir tray in accordance with embodiments of the present disclosure. FIG. 7 shows a bottom view of the reservoir tray in accordance with embodiments of the present disclosure. According to one or more embodiments, an assembly is provided that includes the fluidics device 100, the reservoir tray 250, and a cover tray 260 configured for nesting engagement on top of the reservoir tray 250 or the fluidics device 100. FIG. 8 shows an exploded perspective view of the fluidics device 100 as part of an assembly including the reservoir tray nestably engaged on top of the fluidics device 100 and the cover tray 260 nestably engaged on top of the reservoir tray in accordance with embodiments of the present disclosure.

According to one or more embodiments of the presently disclosed subject matter, an assembly is provided for allowing fluid flow between the plurality of wells 120 of the fluidics device 100, the assembly including the fluidics device 100 and the reservoir tray 250 configured for nesting engagement on top of the fluidics device 100. Turning to FIGS. 6 and 7, the reservoir tray 250 can include at least one chamber 270 for containing a respective chamber fluid and an aperture 280 defined in the chamber floor and configured such that the aperture 280 is positioned above the dosing well 110 of the fluidics device 100 when in nesting engagement with the fluidics device 100. The floor of the chamber 270 can be angled and the aperture 280 can be defined at a lower portion of the chamber floor such that the chamber fluid flows through the aperture 280 into the dosing well 110 when the reservoir tray 250 and the fluidics device 100 are nestably engaged. When nestably engaged, the reservoir tray 250 can be positioned just above the fluidics device 100 and the respective chamber fluid flows from each chamber 270 of the reservoir tray 250 through each aperture 280 and into each dosing well 110 of the fluidics device 100.

According to one or more embodiments, the assembly can further include the cover tray 260 configured for nesting engagement on top of the reservoir tray 250 of the fluidics device 100. According to one or more embodiments, the assembly can include one or more additional reservoir trays 250 configured for nesting engagement on top of the fluidics device 100.

Figure 9:
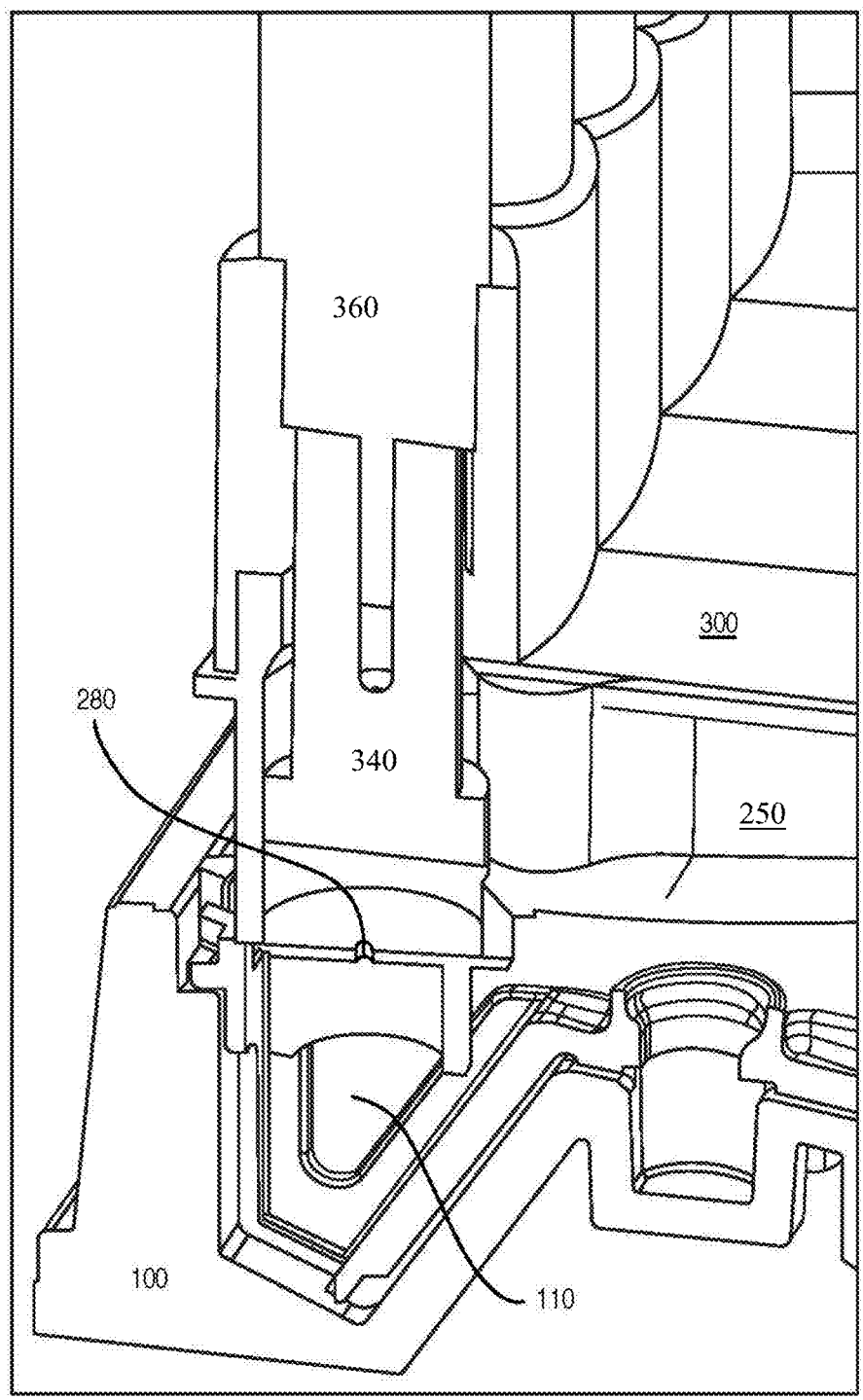
FIG. 9 shows a cross-section view of the piston assembly engaged on top of the fluidics device in accordance with one or more embodiments of the present disclosure.
Figure 10:
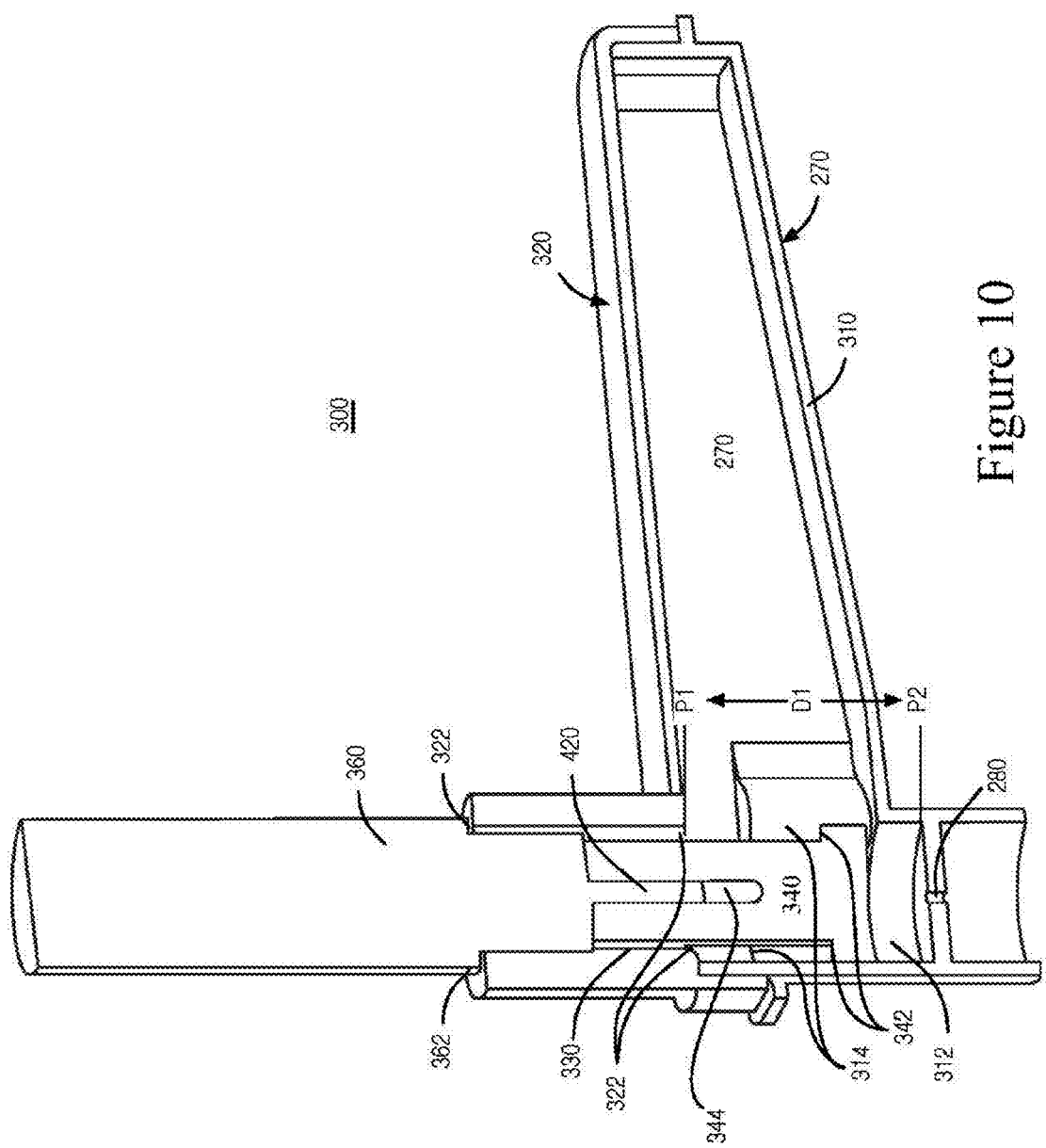
FIG. 10 shows a cross-section view of the piston assembly in accordance with one or more embodiments of the present disclosure.
Figure 11:
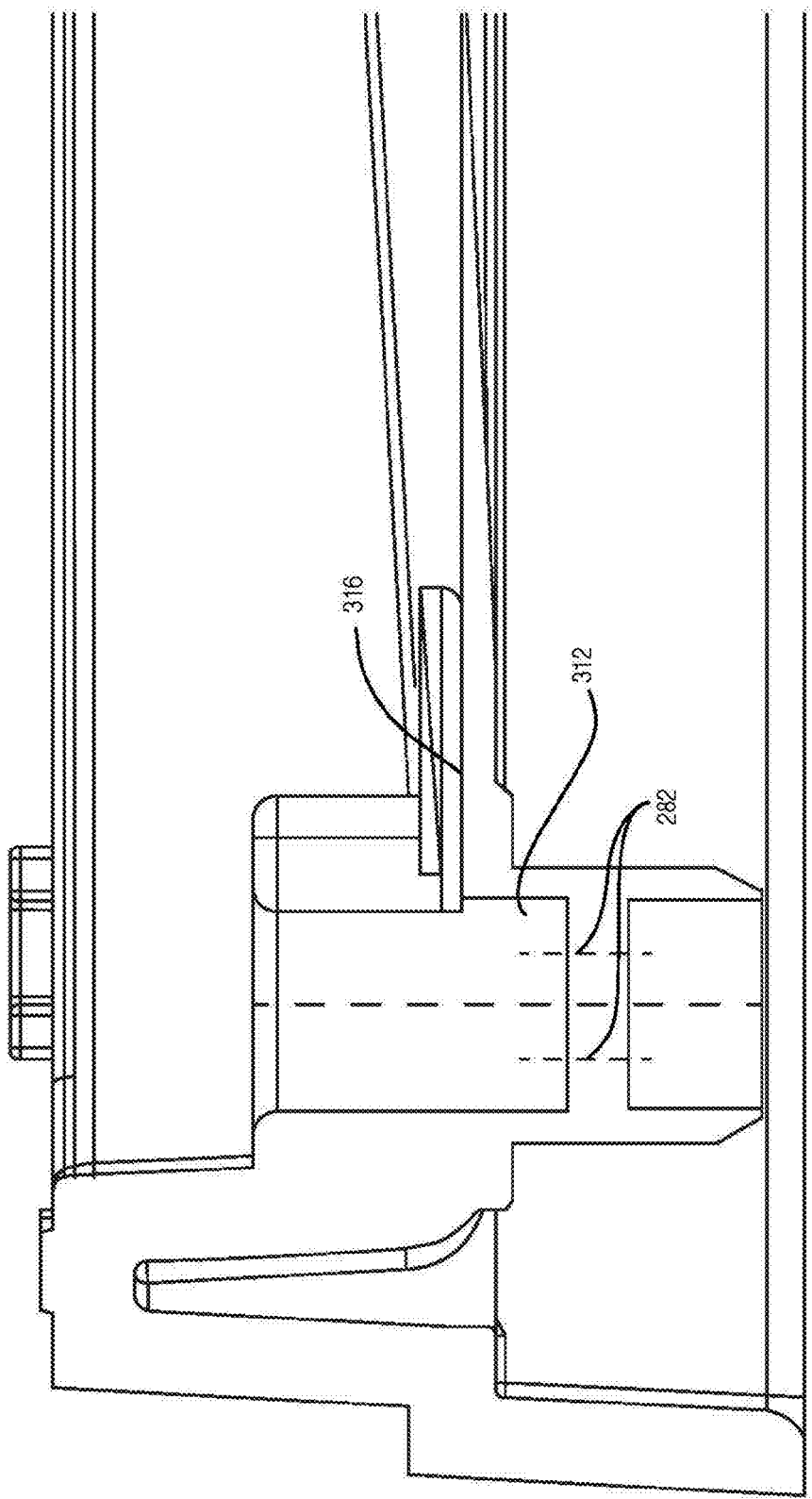
FIG. 11 shows a side view of the piston assembly in accordance with one or more embodiments of the present disclosure.
Figure 12:
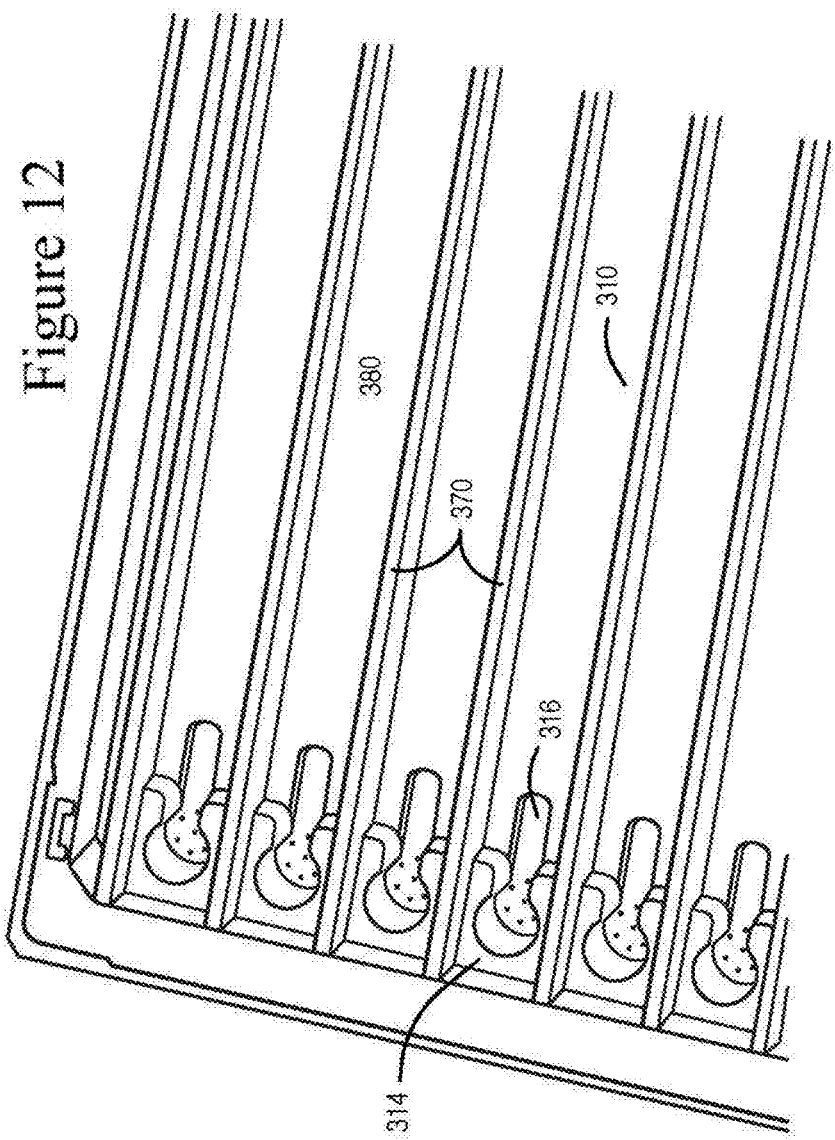
FIG. 12 shows a top view of the reservoir tray of the piston assembly in accordance with one or more embodiments of the present disclosure.
Figure 13:
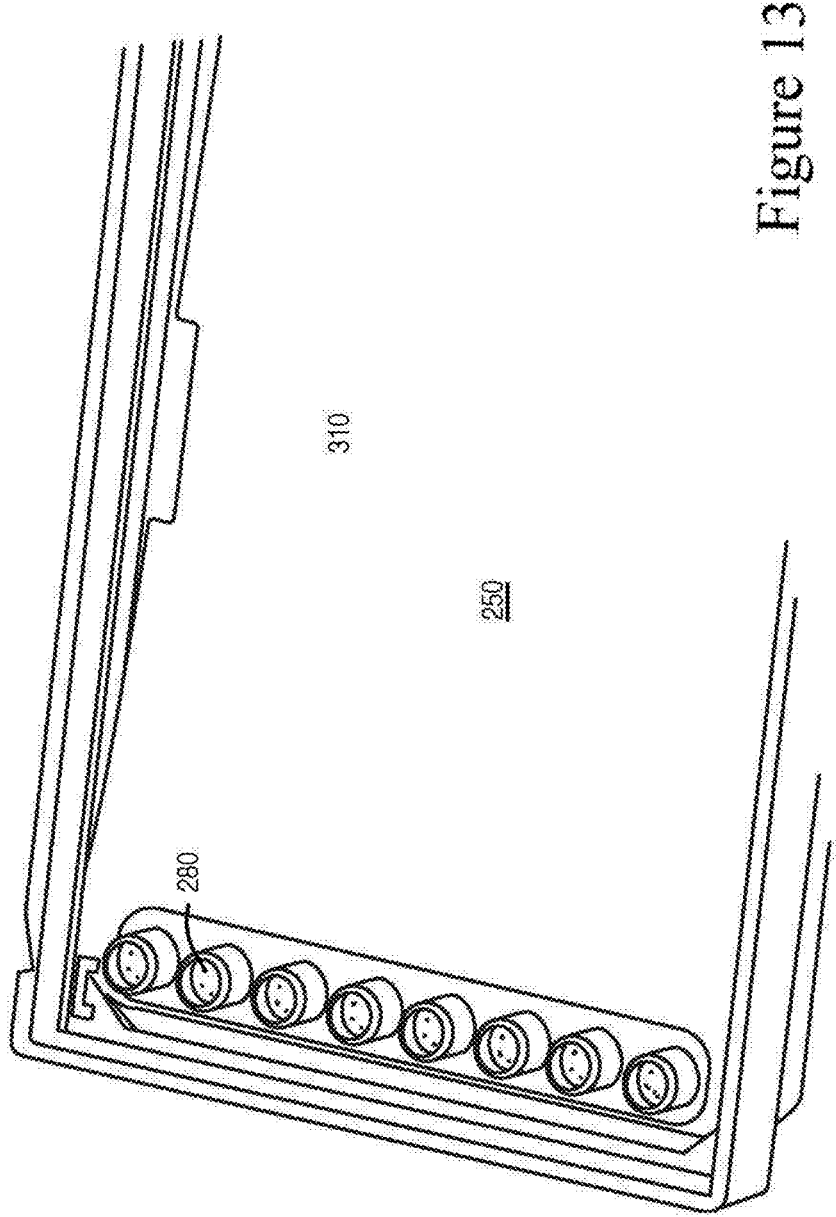
FIG. 13 shows a bottom view of the reservoir tray of the piston assembly in accordance with one or more embodiments of the present disclosure.

According to one or more embodiments of the presently disclosed subject matter, a piston assembly 300 is provided for allowing fluid flow between a reservoir tray 250 and a fluidics device 100, the piston assembly 300 including the reservoir tray 250 configured for nesting engagement with the fluidics device 100. FIG. 9 shows a cross-section view of the piston assembly 300 engaged on top of the fluidics device 100 in accordance with one or more embodiments of the present disclosure. FIG. 10 shows a cross-section view of the piston assembly 300 in accordance with one or more embodiments of the present disclosure. FIG. 11 shows a side view of the piston assembly 300 in accordance with one or more embodiments of the present disclosure. FIG. 12 shows a top view of the reservoir tray 250 of the piston assembly 300 in accordance with one or more embodiments of the present disclosure. FIG. 13 shows a bottom view of the reservoir tray 250 of the piston assembly 300 in accordance with one or more embodiments of the present disclosure.

Turning to FIGS. 9-11, the reservoir tray 250 can include a liquid chamber 270 defining a chamber floor 310 for containing a dosing fluid 1, an aperture 280 defined in the chamber floor 310 and positioned above a dosing well 110 of the fluidics device 100 when the reservoir tray 250 is nestably engaged with the fluidics device 100. The chamber floor 310 can be angled and the aperture 280 can be defined at a lower portion of the chamber floor 310 such that the dosing fluid 1 flows through the aperture 280 into the dosing well 110 of the fluidics device 100 when the reservoir tray 250 and the fluidics device 100 are nestably engaged. The piston assembly 300 can further includes a reservoir cover 320 defining a piston chamber 330 that receives at least a portion of a piston 340 for allowing the piston 340 to translate between a first position P1 a distance D1 from the aperture 280 and a second position P2 proximal to the aperture 280. Additionally, the piston assembly 300 can include a crank 360 engaged with the piston 340 for translating the piston 340 between the first position P1 and the second position P2 such that the translation from the first position P1 to the second position P2 results in a portion of the dosing fluid 1 flowing through the aperture 280 to the dosing well 110 when the reservoir tray 250 and the fluidics device 100 are nestably engaged.

Alternatively, in accordance with one or more embodiments of the presently disclosed subject matter, a piston assembly 300 is provided for allowing fluid flow between a reservoir tray 250 and a fluidics device 100, the piston assembly 300 including a reservoir tray 250 configured for nesting engagement with a fluidics device 100 and including a liquid chamber 270 defining a chamber floor 310 and dividing walls 370 creating subchambers 380 for housing a dosing fluid 1. Each of the subchambers 380 can include an aperture 280 defined in the chamber floor 310 and positioned above a dosing well 110 of the fluidics device 100 when the reservoir tray 250 is nestably engaged with the fluidics device 100. The chamber floor 310 can be angled and the aperture 280 can be defined at a lower portion of the chamber floor 310 such that the dosing fluid 1 flows through the aperture 280 into the dosing well 110 of the fluidics device 100 when the reservoir tray 250 and the fluidics device 100 are nestably engaged. The reservoir cover 320 can define a piston chamber 330 housing a piston 340 for each of subchambers 380 for allowing the piston 340 to translate a between a first position P1 a distance D1 from the aperture 280 and a second position P2 proximal to the aperture 280. Additionally the piston assembly 300 can include a crank assembly 390 engaged with the pistons 340 for translating the pistons 340 such that a portion of the dosing fluid 1 flows through the aperture 280 when the reservoir tray 250 and the fluidics device 100 are nestably engaged.

The piston chamber 330 serves at least two purposes. First, the piston chamber 330 serves to guide and locate the pistons 340 during translation between the first position P1 and the second position P2. In one example, the piston chamber 330 may have a 5.2 mm diameter and the piston 340 may have a 5.0 mm diameter such that the pistons 340 do not bind to the piston chamber. Secondly, the piston chamber 330 serves, along with the reservoir cover 320 generally, to form a barrier between the sterile and non-sterile components, namely the crank 360, crank assembly 390, solenoid 400 and/or electronics unit 440.

According to one or more embodiments, the piston(s) 340 translates from the first position P1 to the second position P2 a distance D1 such that a volume of dosing fluid 1 is transferred from the liquid chamber 270 of the reservoir tray 250 to the dosing well 110 of the fluidics device 100 through the aperture 280. In some embodiments, the piston(s) 340 repeatedly translates between the first position P1 and second position P2 a distance D1 such that the same volume of dosing fluid 1 is repeatedly transferred from the liquid chamber 270 of the reservoir tray 250 to the dosing well 110 of the fluidics device 100. In alternative embodiments, the piston(s) 340 may translate varying distances D1 during each translation, each distance D1 having a different starting first position P1 and therefore transferring a different volume of dosing liquid upon each translation. In one example, the piston(s) may translate at certain predetermined time intervals. Any number of translations of the piston(s) 340 may occur at any number of time intervals, whether varying or the same, and each of these translations may occur over a distance D1, which may vary or remain the same.

According to one or more embodiments, a piston assembly 300 can include an aperture 280 defining one or more openings 282. The one or more openings 282 can be configured for communication with the dosing fluid 1 in the liquid chamber 270 such that surface tension of the dosing fluid 1 maintains the dosing fluid 1 in the liquid chamber 270 until the piston 340 is translated from the first position P1 to the second position P2.

According to one or more embodiments, a piston assembly 300 can include a piston chamber 330 defining a chamber lip 332 for engaging with a piston catch 342 defined by a piston 340, thereby retarding the translation of the piston 340 when the piston 340 translates from the second position P2 to the first position P1.

According to one or more embodiments, a piston assembly 300 can include a reservoir cover 320 defining a cover lip 322 for engaging with a crank catch 362 defined by the crank 360, thereby retarding the translation of the crank 360 when the piston 340 is translating from the second position P2 to the first position P1.

According to one or more embodiments, a piston assembly 300 can include a chamber floor 310 defining a piston well 312 including the aperture 280 for receiving the piston 340 in the second position P2 and the dosing fluid 1.

According to one or more embodiments, a piston assembly 300 can include a piston well 312 having a piston well wall 314 for nestably engaging at least half of the circumference of the piston 340 during the entire translation between the first position P1 and the second position P2 and for delivering the dosing fluid 1 to the piston well 312. Additionally, the piston well wall 314 can aid in preventing the dosing liquid 1 from collecting between the piston 340 and the wall of the subchamber 380 at the lower portion of the liquid chamber 270.

According to one or more embodiments, a piston assembly 300 can include a chamber floor 310 defining a floor recess 316 at the lower portion of the chamber floor 310 proximal to the piston well 312 and the piston well wall 314 for receiving the dosing fluid 1 and delivering the dosing fluid 1 to the piston well 312.

According to one or more embodiments, a piston assembly 300 can include a crank 360 having a pin 420 engaged within a piston channel 344 defined in the piston 340 for engaging the crank 360 to the piston 340. Further, a piston assembly 300 can include a crank 360 in communication with a solenoid 400.

Figure 14:
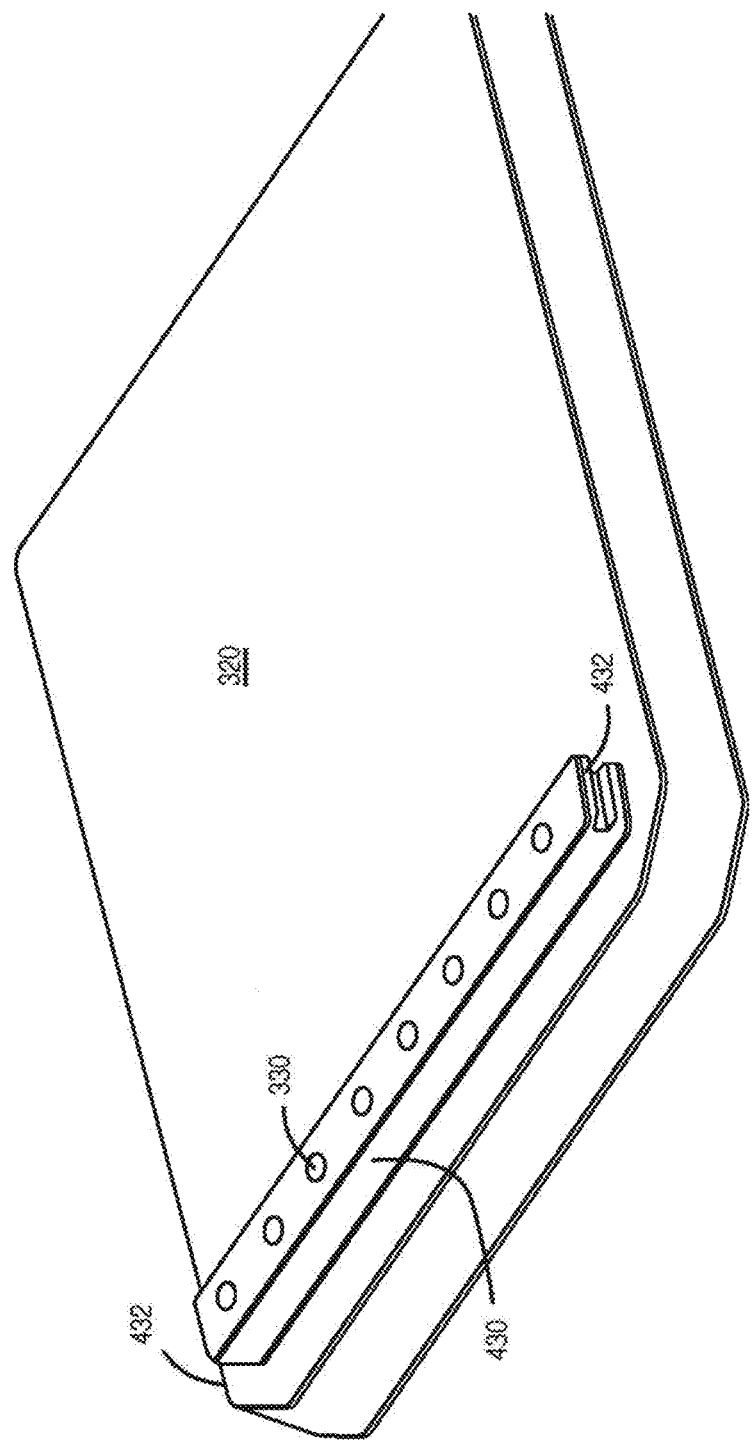
FIG. 14 shows a top view of the reservoir cover of the piston assembly in accordance with one or more embodiments of the present disclosure.

FIG. 14 shows a top view of the reservoir cover 320 of the piston assembly 300 in accordance with one or more embodiments of the present disclosure. In FIG. 14, the reservoir cover 320 defines several piston chambers 330, each housing a piston 340 corresponding to each underlying subchamber 380 and allowing each piston 340 to translate a between a first position P1 and a second position P2. The piston chambers 330 can define a piston guide 430 extending above the remainder of the reservoir cover 320 for guiding the translation of the pistons 340 between the first position and the second position. Further, the piston guide 430 defines electronic guides 432 on each end for receiving an electronic unit 440 (not shown) for controlling the translation of the pistons 340, cranks 360 and/or crank assembly 390. In one example, the electronics unit 440 may include a timer that can be programmed via a dip switch so that varying piston 340 translation cycles may be implemented.

Figure 15:
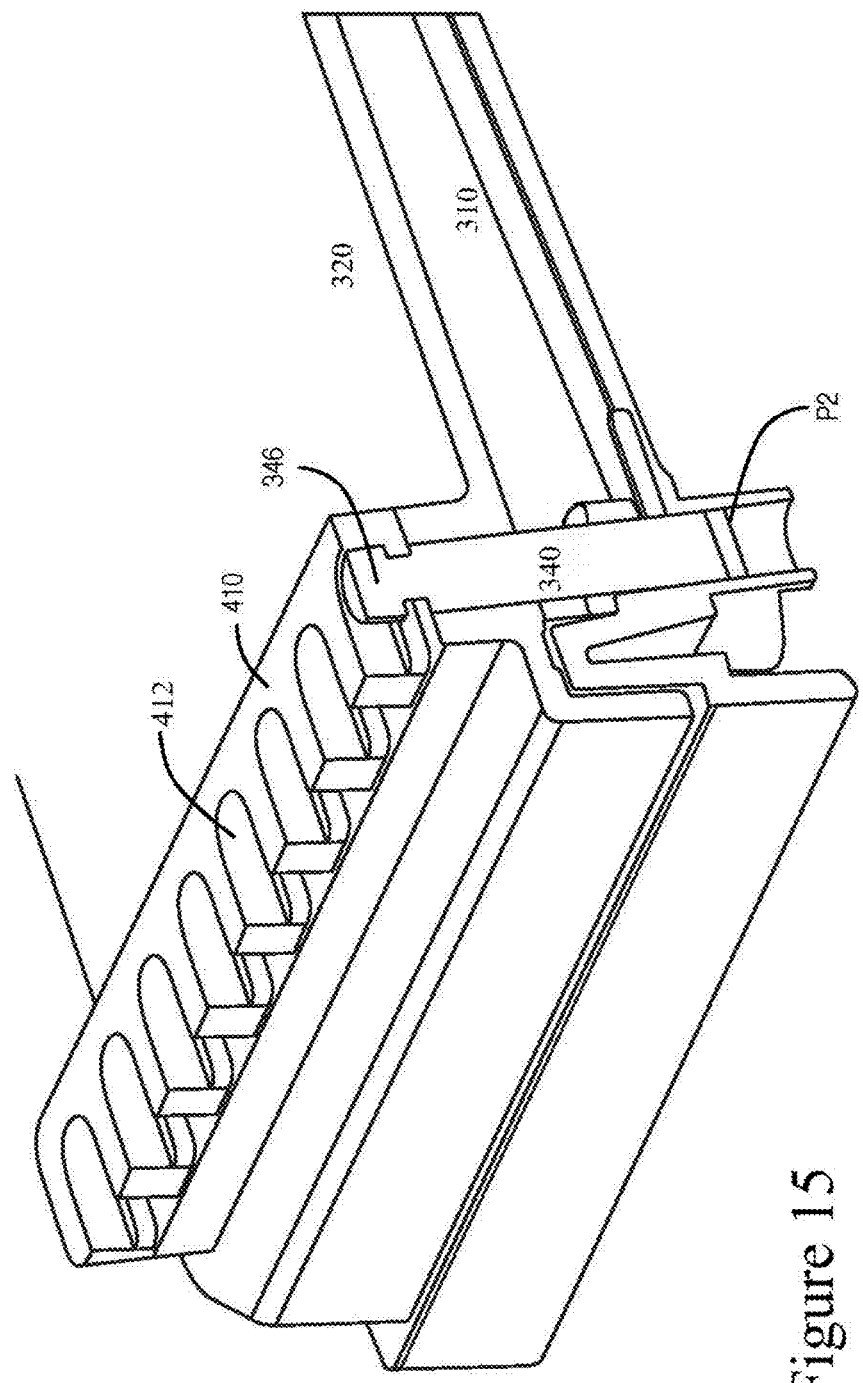
FIG. 15 illustrates the piston assembly including a crank assembly in accordance with one or more embodiments of the present disclosure.

FIG. 15 illustrates the piston assembly 300 including a piston bar 410 in accordance with one or more embodiments of the present disclosure. A piston assembly 300 can include a crank assembly 390 having one or more cranks 360. Each crank 360 can be engaged with the piston 340 of each of one of the subchambers 380 for translating the piston 340 between the first position P1 and the second position P2. In some embodiments, each crank 360 can be in communication with a solenoid 400 including a pin 420 engaged with a piston channel 344 defined by each piston 340.

According to one or more embodiments, a piston assembly 300 can include pistons 340, each of the pistons 340 defining a piston head 346. Further, the piston assembly can include a crank assembly 390 having a piston bar 410 engaged with all of the piston heads 346 for translating the pistons 340 simultaneously between the first position P1 and the second position P2. The crank assembly can additionally include at least one crank 360 engaged with the piston bar 410 for translating the piston bar 410, thereby translating the pistons 340 between the first position P1 and the second position P2. The at least one crank 360 can be in communication with at least one solenoid 400 including a pin 420 engaged with a piston bar channel 412 defined by the piston bar 410. In one example, three 13.5 mm solenoids 400 can be in communication with a crank assembly 390. In another example, one 20 mm solenoid 400 can be in communication with a piston bar 410. In an alternative embodiments an electronics unit 440 can be in communication with one or more solenoids 400 for translating the piston bar 410, crank assembly 390, cranks 360 and/or pistons 340.

The piston assembly 300 can be made of any material that is suitable for allowing fluid flow between a reservoir tray 250 and a fluidics device 100. The type of material chosen can depend on the desired use of the piston assembly 300. For example, the user of the piston assembly 300 can choose the material based on the dosing fluid 1 that will be used and the expected interaction of the dosing fluid 1 with the material. Thus, the piston assembly 300 can be made of any suitable material including, for example, a polymer, a synthetic polymer, a TOPAS® COC polymer, a biodegradable polymer, a plastic, a biodegradable plastic, a thermoplastic, a polystyrene, a polyethylene, a polypropylene, a polyvinyl chloride, a polytetrafluoroethylene, a silicone, a glass, a PYREX, or a borosilicate, or combinations thereof. In addition, the fluidics device 100, the dosing well channel cover 160, the channel cover 230, and the wick 140, 142, 144 may each be made from the same materials as the piston assembly 300. In one example, a user may wish to have each of the piston assembly 300, the fluidics device 100, the dosing well channel cover 160, the channel cover 230, and the wick 140, 142, 144 made from the same material such that the interaction of the dosing well fluid with the material does not vary.

Figure 16:
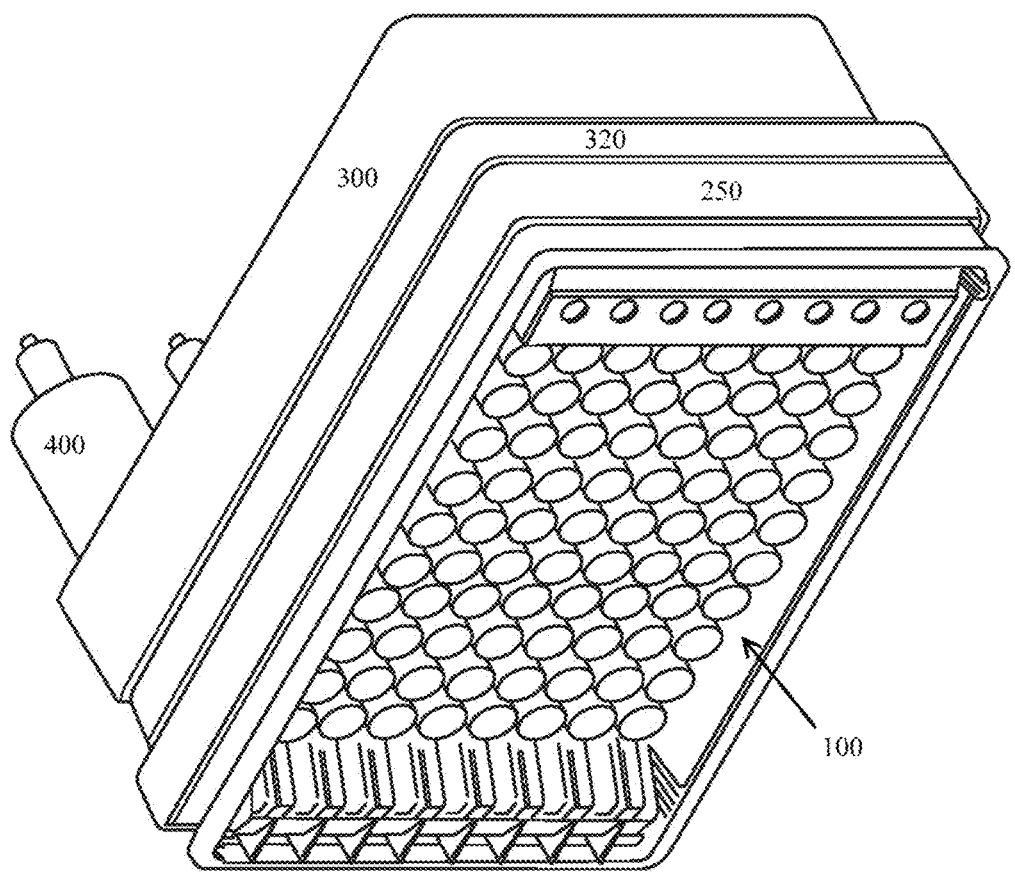
FIG. 16 shows a bottom perspective view of the piston assembly engaged on top of the fluidics device in accordance with one or more embodiments of the present disclosure.
Figure 17:
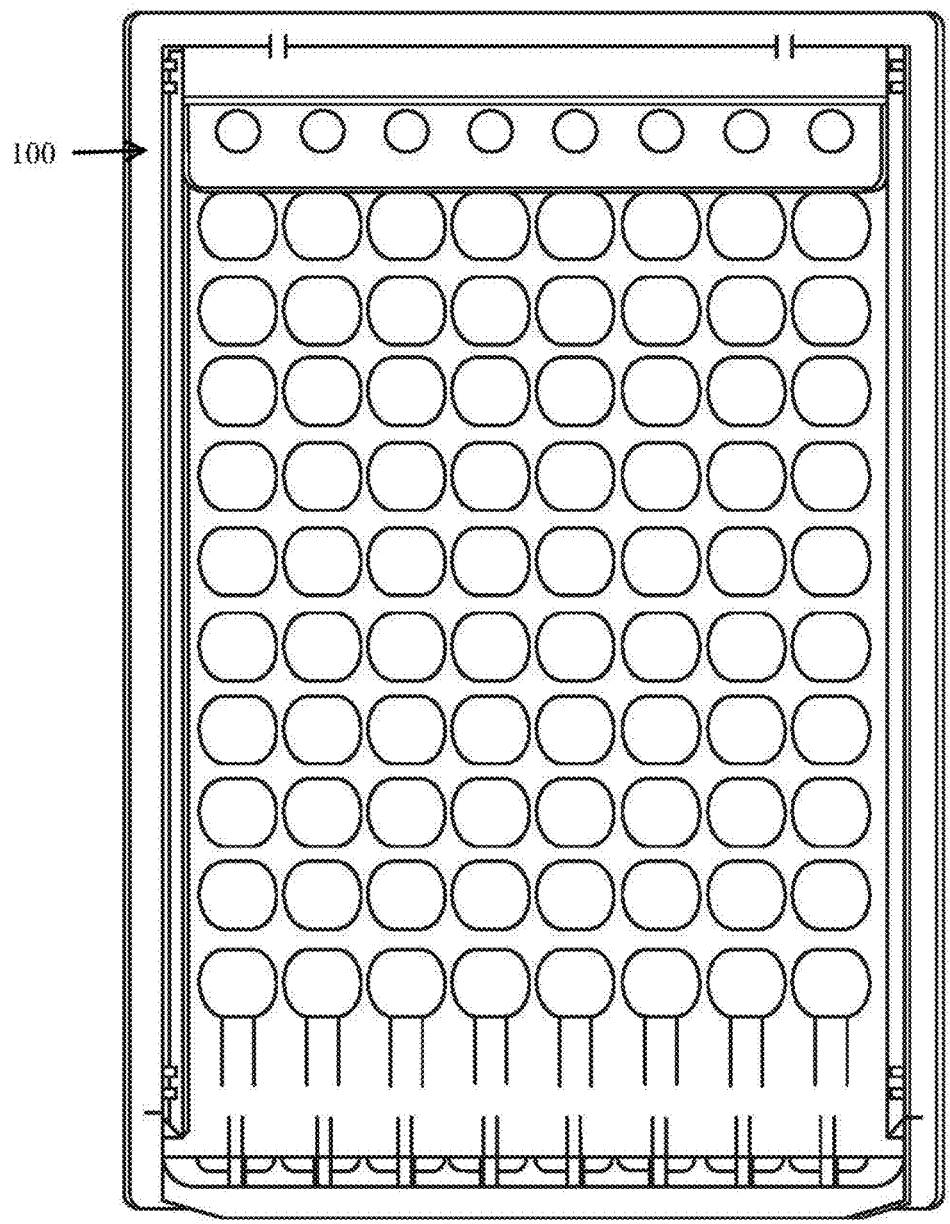
FIG. 17 shows a bottom view of the fluidics device in accordance with one or more embodiments of the present disclosure.
Figure 18:
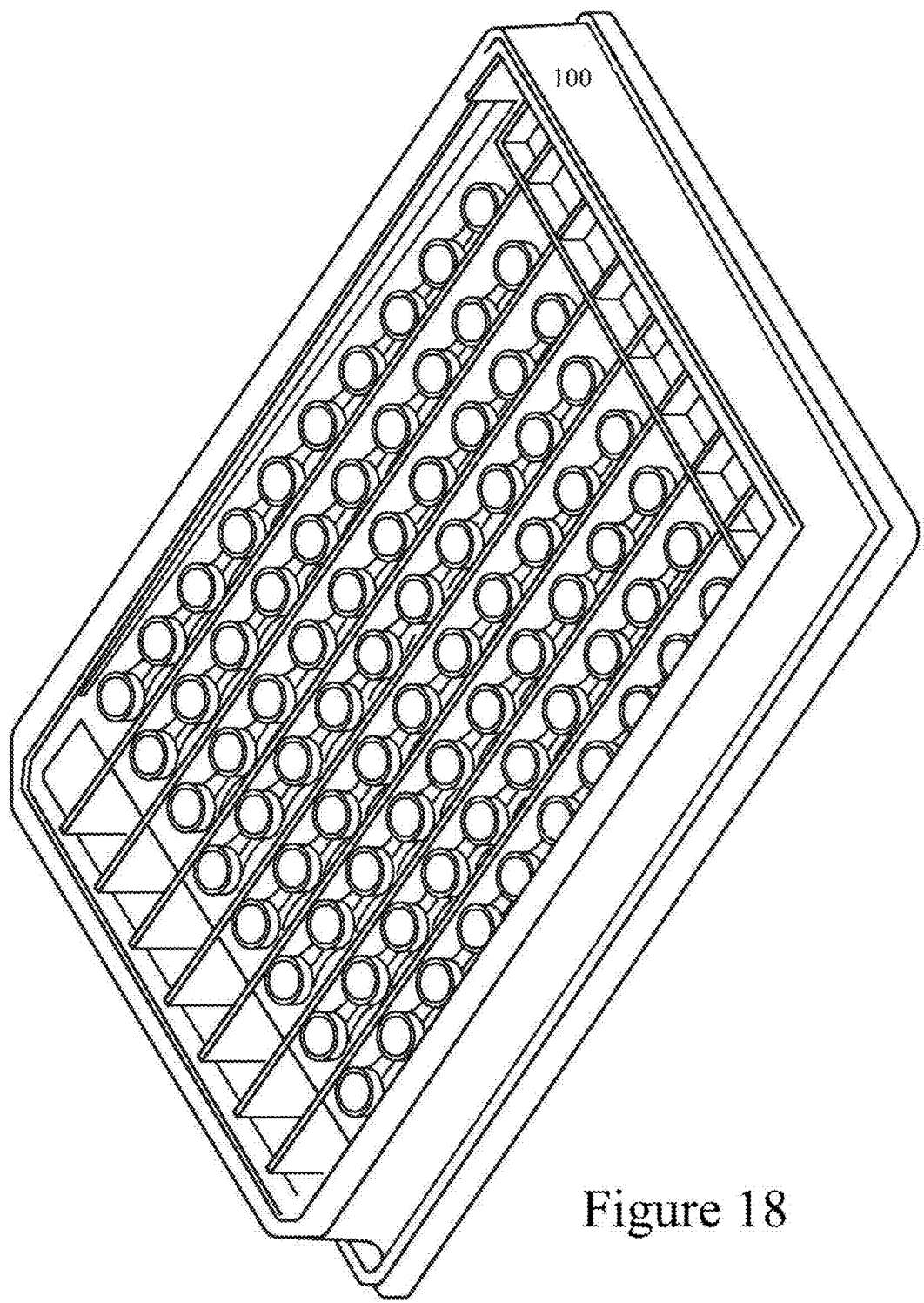
FIG. 18 shows a top view of the fluidics device in accordance with one or more embodiments of the present disclosure.
Figure 19:
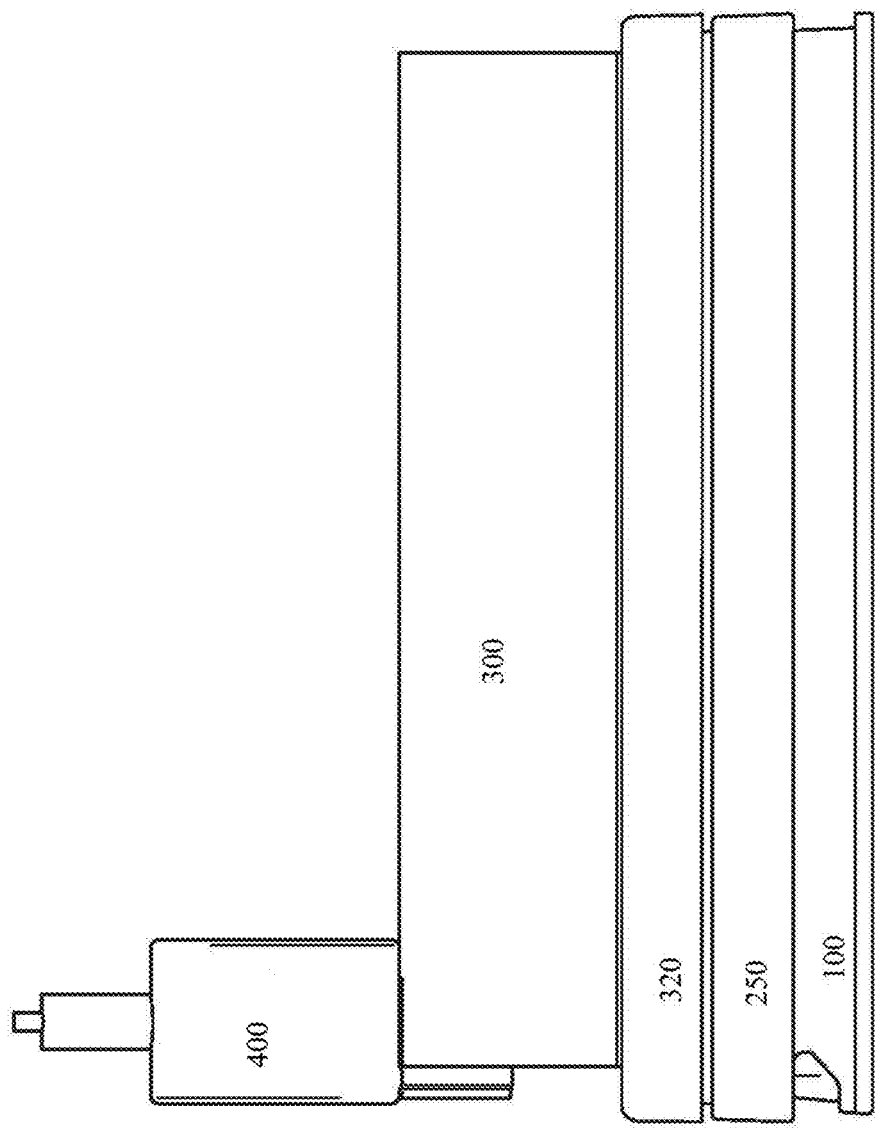
FIG. 19 shows a side view of the piston assembly engaged on top of the fluidics device in accordance with one or more embodiments of the present disclosure.
Figure 20:
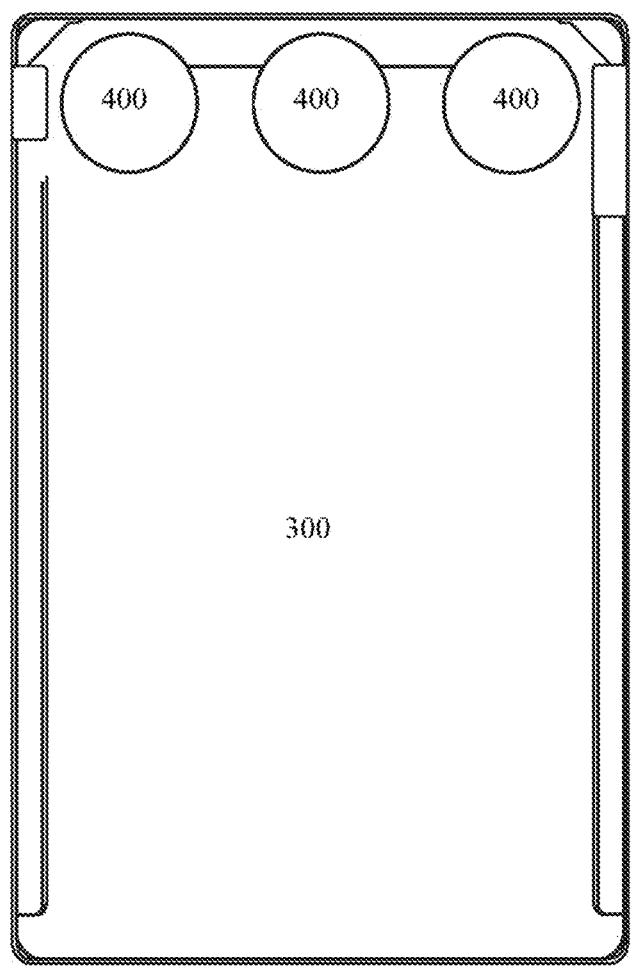
FIG. 20 shows a top view of the piston assembly including three solenoids in accordance with one or more embodiments of the present disclosure.
Figure 21:
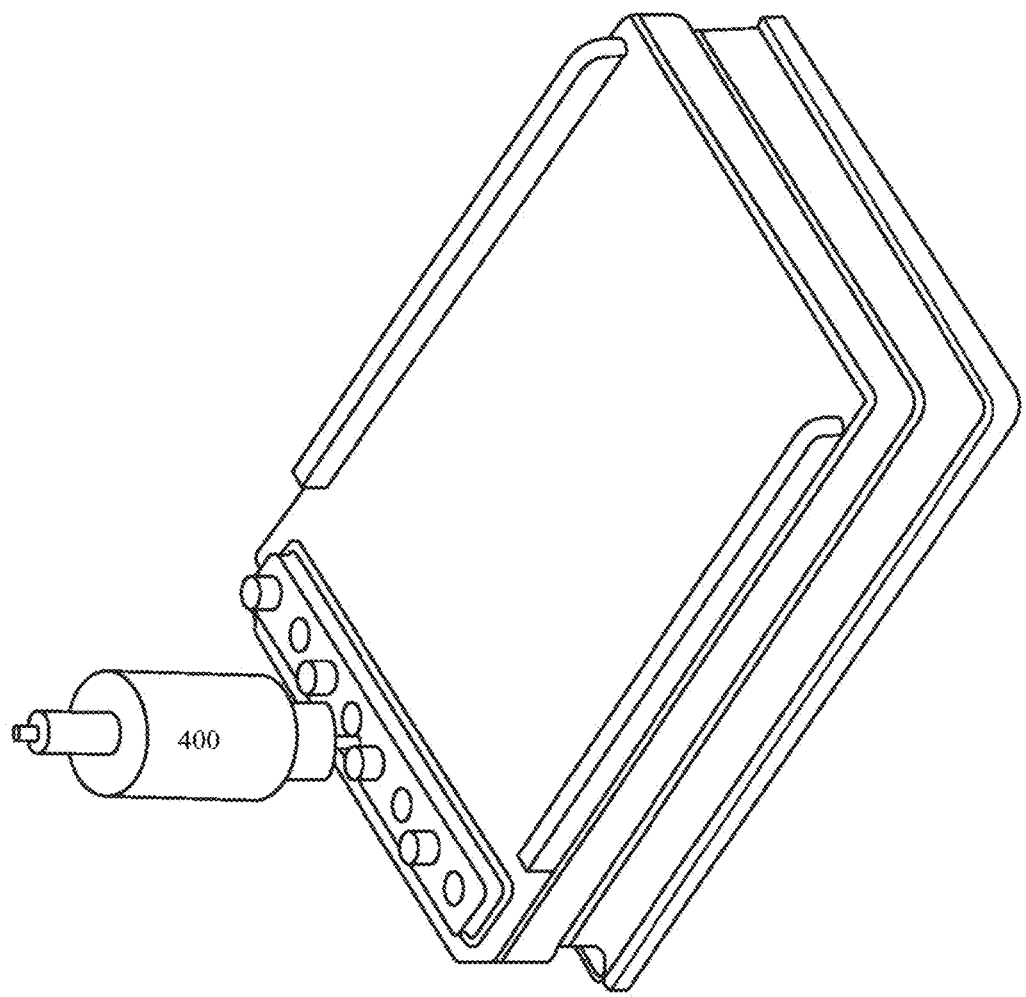
FIG. 21 shows an upward facing perspective of the piston assembly including one solenoid in accordance with one or more embodiments of the present disclosure.
Figure 22:
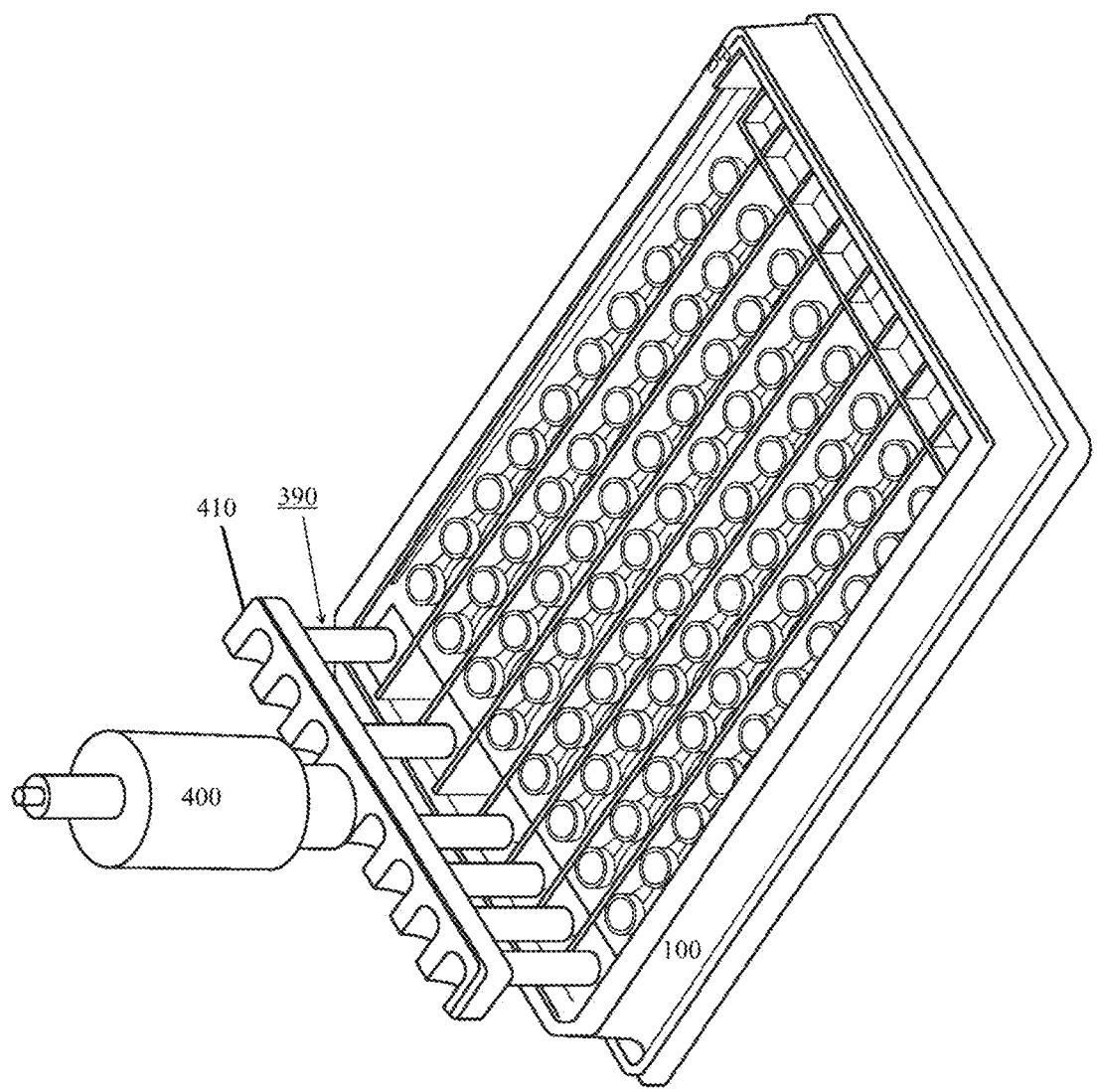
FIG. 22 shows an upward facing perspective of the fluidics device, pistons, a piston bar, and one solenoid in accordance with one or more embodiments of the present disclosure.
Figure 23:
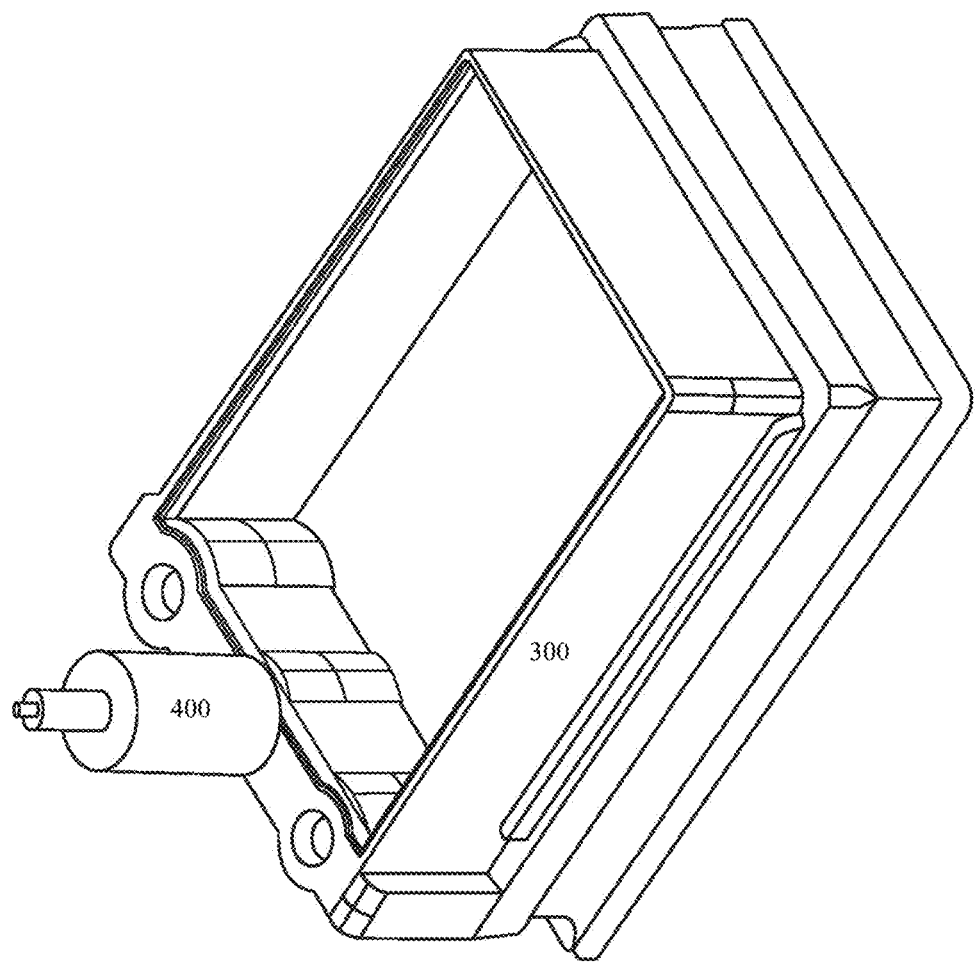
FIG. 23 shows an upward facing perspective of the solenoid and electronics unit in accordance with one or more embodiments of the present disclosure.
Figure 24:
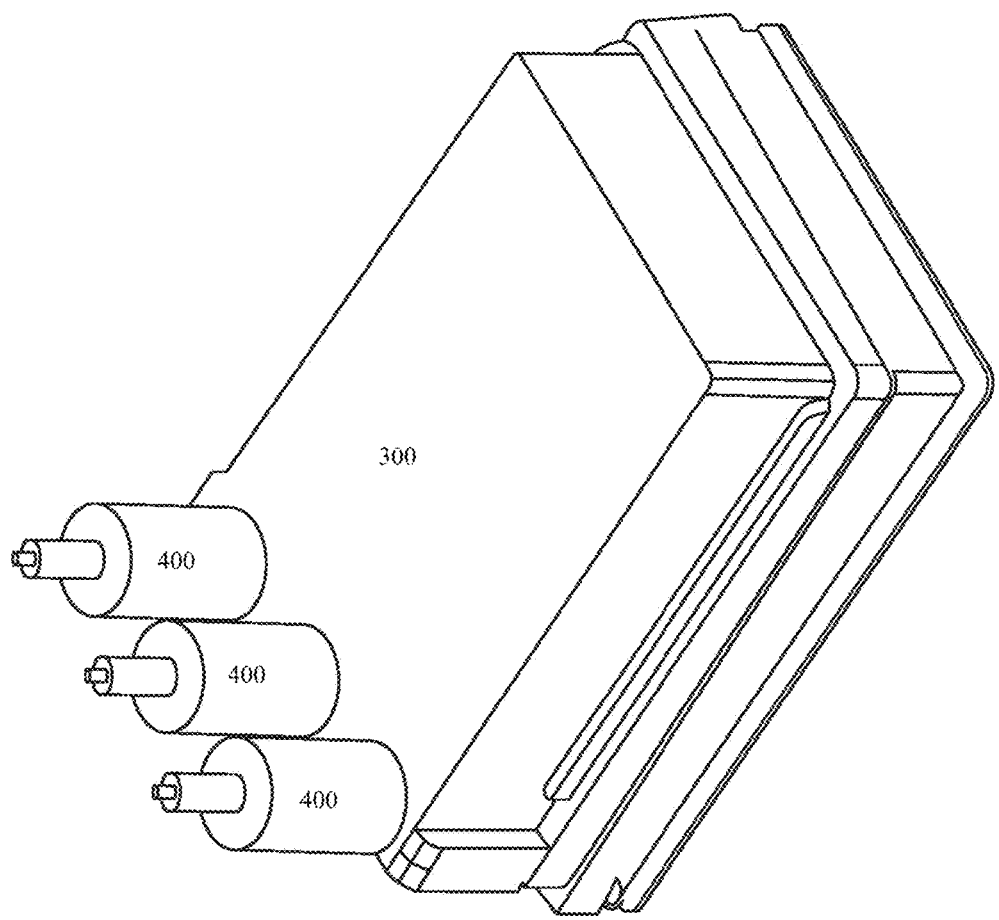
FIG. 24 shows an upward facing perspective of the piston assembly including solenoids in accordance with one or more embodiments of the present disclosure.

FIG. 16 shows a bottom perspective view of the piston assembly 300 engaged on top of the fluidics device 100 in accordance with one or more embodiments of the present disclosure. FIG. 17 shows a bottom view of the fluidics device 100 in accordance with one or more embodiments of the present disclosure. FIG. 18 shows a top view of the fluidics device 100 in accordance with one or more embodiments of the present disclosure. FIG. 19 shows a side view of the piston assembly 300 having a crank assembly 390, the piston assembly 300 engaged on top of the fluidics device 100 in accordance with one or more embodiments of the present disclosure. FIG. 20 shows a top view of the piston assembly 300 having a crank assembly 390 including three solenoids 400 in accordance with one or more embodiments of the present disclosure. FIG. 21 shows an upward facing perspective of the piston assembly 300 including one solenoid 400 in accordance with one or more embodiments of the present disclosure. FIG. 22 shows an upward facing perspective of the fluidics device 100, pistons 340, a piston bar 410, and one solenoid 400 in accordance with one or more embodiments of the present disclosure. FIG. 23 shows an upward facing perspective of the solenoid 400 and electronics unit 440 in accordance with one or more embodiments of the present disclosure. FIG. 24 shows an upward facing perspective of the piston assembly 300 including solenoids 400 in accordance with one or more embodiments of the present disclosure.

Figure 25:
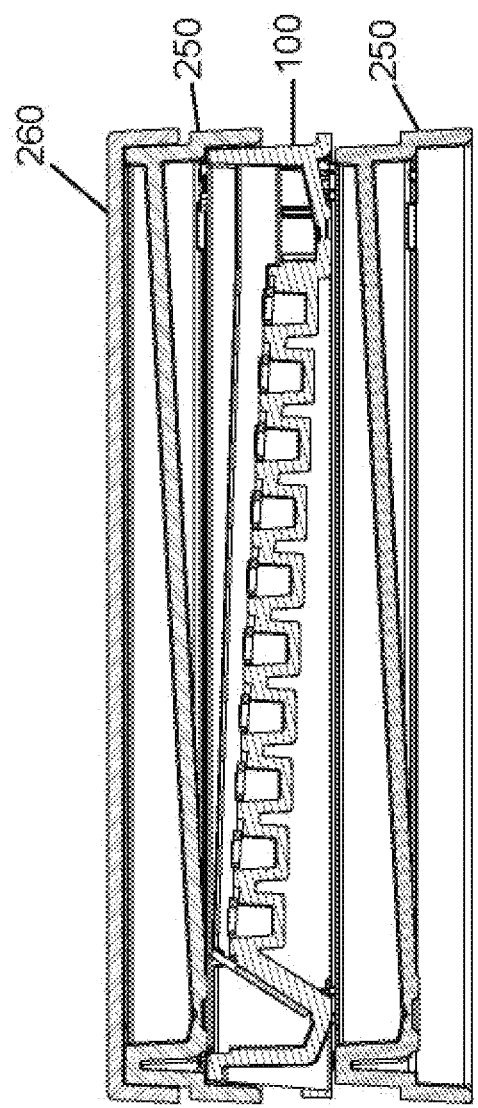
FIG. 25 shows a side view of the fluidics device of FIG. 1 as part of an assembly including a cover tray, a reservoir tray nestably engaged on top of the fluidics device, and a second reservoir tray nestably engaged underneath the fluidics device in accordance with embodiments of the present disclosure.

According to one or more embodiments of the presently disclosed subject matter, the overall assembly can further include a second reservoir tray 250 configured for nesting engagement underneath the fluidics device 100. FIG. 25 shows an exploded side view of this overall assembly including the second reservoir tray 250 in accordance with embodiments of the present disclosure. For this assembly, the fluidics device 100 can include the collection well 170 that is downstream from the plurality of wells 120 and the collection well 170 can define an aperture such that when the second reservoir tray 250 is in nesting engagement underneath the fluidics device 100, fluid from the collection well 170 of the fluidics device 100 flows through the aperture into the chamber 270 of the second reservoir tray 250. Referring to FIG. 25, the fluid can flow from the reservoir tray 250 nestably engaged on top of the fluidics device 100 from right to left through the aperture 280 of the reservoir tray 250 into the dosing well 110 of the fluidics device 100. The fluid can flow from the dosing well 110 from left to right through the aperture of the collection well 170 of the fluidics device 100 into the chamber 270 of the reservoir tray 250 nestably engaged underneath the fluidics device 100. The fluid can then flow in the second reservoir tray 250 from right to left.

According to one or more embodiments, the assembly can include one or more additional reservoir trays 250 configured for nesting engagement underneath the fluidics device 100.

According to one or more embodiments of the presently disclosed subject matter, the assembly can include a second fluidics device 100 configured for nesting engagement underneath the fluidics device 100. In this assembly, the fluidics device 100 can include the collection well 170 downstream from the plurality of wells 120 and the collection well 170 can define an aperture such that fluid from the collection well 170 flows through the aperture into the dosing well 110 of the second fluidics device 100 underneath when the fluidics devices 100 are nestably engaged.

Figure 26:
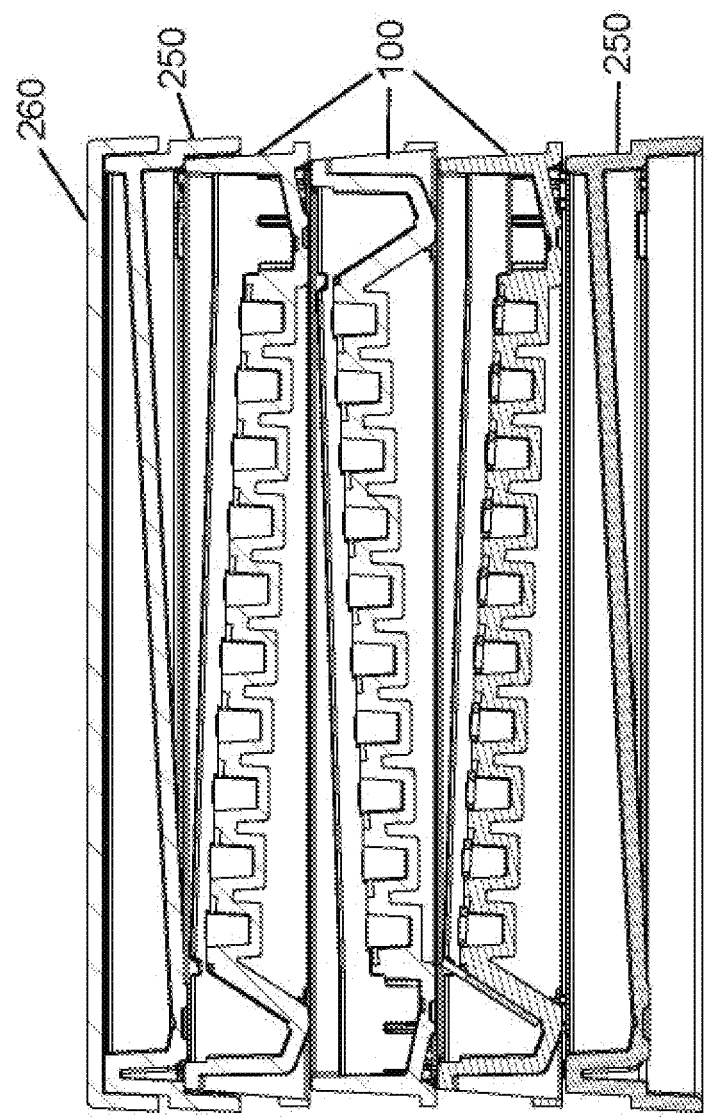
FIG. 26 shows a side view of the assembly of FIG. 25 further including two additional fluidics devices in nestable engagement in accordance with embodiments of the present disclosure.

According to one or more embodiments of the presently disclosed subject matter, the assembly can include one or more additional fluidics devices 100 configured for nesting engagement underneath the second fluidics device 100. The additional fluidics devices 100 can each include the collection well 170 downstream from the plurality of wells 120 and each collection well 170 can define an aperture such that fluid from the collection well 170 flows through the aperture into the dosing well 110 of the additional fluidics device 100 positioned underneath when the multiple fluidics devices 100 are nestably engaged. FIG. 26 shows an exploded side view of this assembly including a total of three fluidics devices 100 nestably engaged, reservoir trays 250 engaged on top of and underneath the three fluidics devices 100, and cover tray 260 engaged on top of the top reservoir tray 250 in accordance with embodiments of the present disclosure.

According to one or more embodiments of the presently disclosed subject matter, a method is provided for employing an assembly including one or more nestably engaged fluidics devices 100 and one or more reservoir trays 250 nestably engaged on top of and/or underneath the fluidics devices 100 as exemplified in FIGS. 8 and 25-26. The method can include adding a dosing fluid to the dosing well 120 and adding a respective host fluid to the plurality of wells 120 of the fluidics device(s) 100 such that the fluid is in fluid contact with the fluid flow channel 130, whereby the dosing fluid flows to each of the respective host fluids in the plurality of wells 120 in a tempered manner. The method includes positioning the reservoir tray 250 above the fluidics device(s) 100 such that the reservoir tray 250 and the fluidics device(s) 100 are in nesting engagement, and adding the respective chamber fluid to the respective chamber 270 of the reservoir tray 250, whereby the respective chamber fluid flows into the dosing well 110 of the fluidics device 100 that is nestably engaged underneath the reservoir tray 250. In this manner, a larger supply of dosing fluid than can be contained by the dosing well 110 alone can be provided at a tempered rate to the one or more fluidics devices 100 that are nestably engaged underneath the reservoir tray 250.

According to one or more embodiments, the dosing fluid can include one or more of a drug, a legal or illegal drug, a toxin, an agent of warfare, a fragrance, a food spice, an oil, a gas, a metabolite, a compound, a hormone, a solution, a solute, a composite, a nutrient media, a differentiation media, or a growth media.

According to one or more embodiments, the plurality of wells 120 of the fluidics device 100 can contain a respective cell culture, whereby an effect or parameter or response of the tempered exposure to the dosing fluid on the cells can be measured. The effect or parameter or response of the tempered exposure to the dosing fluid on the cell cultures to be measured can be one or more of pharmacokinetics, drug metabolism, toxicity, pre-clinical pharmaceutical studies, cell response, cell receptor response, cell feedback signals, cell growth, cell death, cell differentiation, or cell regeneration. The respective cell culture can be a stem cell culture or a progenitor cell culture.

According to one or more embodiments, the method for employing the assembly can further include removing an aliquot of the respective host fluid from one or more of the plurality of wells 120 at one or more time periods to measure an effect or parameter or cell response of or to the dosing fluid from having been tempered through the plurality of wells 120. The plurality of wells 120 can contain a respective cell culture, and the method can include removing an aliquot of the respective host fluid from one or more of the plurality of wells 120 at one or more time periods to measure an effect or parameter (e.g., cytotoxicity of the individual cells of the cell culture) of the dosing fluid (e.g., fluid including a test compound) on the cells, or the response of the cells thereto. Notably, fluid, as used herein, may include either a liquid, a gas, or both.

According to at least one embodiment, the an in vitro assay method for determining whether a parameter was diminished or enhanced by a cell culture response to a test compound is provided. The method may include applying a dynamic fluid (e.g., a liquid or a gas being applied to a 'dynamic' dosing well 110D, where dynamic is a label and not a qualitative descriptor) including the test compound to a dynamic dosing well 110D of a fluidics device 100. The fluidics device 100 may include any of the number of embodiments described herein. For example, the fluidics device may include a plurality of dynamic wells 120D each containing a cell culture therein positioned downstream from the dynamic dosing well 110D and in fluid communication therewith. Additionally, the fluidics device 100 may include a plurality of 'control' wells 120C each containing a cell culture therein positioned downstream from the 'control' dosing well 110C and in fluid communication therewith. The fluidics device 100 may include a number of different dosing wells 110 associated with their respective plurality of downstream wells 120—each dosing well 110 being positioned in a distinct row of one or separate fluidics devices 100. In another embodiment, the method may include applying a control fluid not including the test compound to a control dosing well 110C of the fluidics device 100.

The assay method may further include the step of applying a static fluid (again, the term 'static' is a label and not a qualitative descriptor of the fluid itself) including the test compound to a static well 120S. Analysis may be performed on the fluids in the wells 120D, 120S for comparison. For example, any number of bioassays may be performed. A bioassay may include biological, biochemical, microscopic, visualization techniques or plate imaging bioassays. Further, the bioassay may be any method involving an instrumentality for measuring a parameter of the fluidic environment or intracellular environment of the cell culture or fluids. The bioassay may be performed to measure a parameter of any of a number of wells, either together or individually. The measurement of the parameter may determine a value associated therewith for further analysis. In at least one embodiment, the parameter may include one or more of metabolism byproducts, toxicity, cell receptor responses, cell feedback signals, cell growth, cytotoxicity, cell differentiation, cell regeneration, concentration, radiation, optical qualities, fluorescence, luminescence, presence of chemical constituents, presence of antigen constituents, colorimetrics, image or visualization qualities, electrical properties, magnetic properties, or light absorbance. For example, the bioassay may measure parameters such as the concentrations of byproducts or metabolites, or may measure the cytotoxicity of the cell culture. In another example, the parameters may include ionizations or mass for analysis by mass spectroscopy bioassays.

In one embodiment, the method may include performing a 'dynamic' bioassay to measure a parameter of at least one of the plurality of wells and determining a dynamic value. The method may also include performing a static bioassay to measure the parameter of the static well 120S and determining a static value. Additionally, the method may include performing a control bioassay to measure the parameter of at least one of the plurality of control wells 120C and determining a control value. Any number of bioassays may be performed on any number of wells 120 to measure a parameter and determine a respective value. In yet another example, the method may include performing a dynamic bioassay to measure the parameter of at least two of the plurality of dynamic wells 120D and determining a first dynamic value and a second dynamic value.

In at least one embodiment, the method may include comparing the values obtained to make determinations about the relationship between the parameter, cell culture and test compound in static and/or fluidic environments. For example, the method may include any one or more of the following steps: comparing the dynamic value to the static value for determining whether the parameter was diminished or enhanced by the cell culture response to the test compound; comparing the dynamic value to the control value for determining whether the parameter was diminished or enhanced by the cell culture response to the test compound; comparing the first dynamic value to the second dynamic value for determining whether the parameter was diminished or enhanced by the cell culture response to the test compound.

In some embodiments, the dynamic value includes a dynamic effective concentration at a percentage X (ECx) for the parameter, wherein $0 \leq X \leq 100$. In one embodiment, the value of X is 50, and the value may include an EC50 with relation to the parameter and the test compound in the fluidic environment of the row of the fluidics device. In other embodiments, the static value may include a static ECx for the parameter. In embodiments including a dynamic and static ECx, they may be compared and, with respect to some parameters and test compounds, a lower value of the at least one dynamic ECx relative to the static ECx is predictive of the cell culture response to the test compound enhancing the parameter and a higher value of the at least one dynamic ECx relative to the static ECx is predictive of the cell culture response to the test compound diminishing the parameter. With respect to other parameters and test compounds, the opposite may hold true, where a lower value of the at least one dynamic ECx relative to the static ECx is predictive of the cell culture response to the test compound diminishing the parameter and a higher value of the at least one dynamic ECx relative to the static ECx is predictive of the cell culture response to the test compound enhancing the parameter. In other embodiments, the control value may include a control ECx for the parameter and may be compared similarly to the dynamic ECx, resulting in the same predictions.

In yet another method of using the fluidics device 100, a row of the fluidics device 100 may include empty wells 120 for capturing fluidic components therein. For example, upstream wells may contain cell cultures, which may interact with test compounds to create metabolites. As the metabolites flow downstream, they may be captured in the downstream empty wells for collection. In one example, if a drug has a toxic metabolite, it can be challenging to produce significant amounts of that metabolite. The capturing and accumulation of significant amounts (concentrations) of metabolites in wells without cells would ensure a less diverse population of biomolecules present in these empty wells. The high concentration of metabolites could be used for MetID, purification/concentration, or downstream dosing in subsequent experiments. In essence the fluidics device 100 could function as a method for producing high quality, high concentrations of metabolites.

For example, as is described in detail infra, an in vitro assay method for determining whether a parameter was diminished or enhanced by a cell culture response to a test compound is provided. Stated in another way, the method may include predicting effects on a cell culture in response to a test compound. While the disclosure infra specifically relates to determining EC50 values, the steps and methods disclosed are also applicable generally to the methods described supra.

Figure 27:
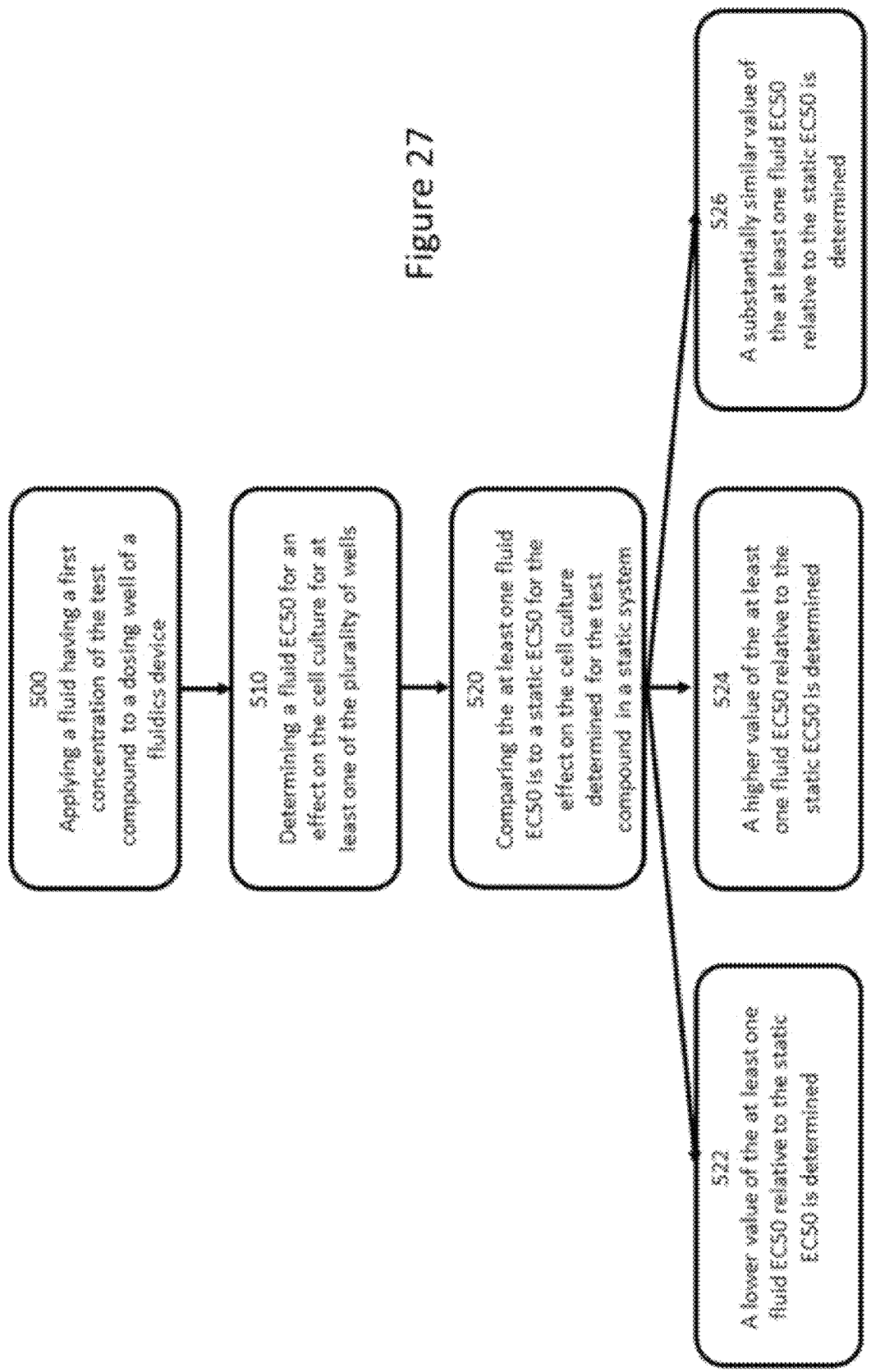
FIG. 27 is a flow diagram showing the steps of one embodiment of the in vitro assay method for predicting the effects on the cell culture.

FIG. 27 is a flow diagram showing the steps of one embodiment of the in vitro assay method for predicting the effects on the cell culture (or the cell culture response effect on the parameter(s)). In step 500, a fluid having a first concentration of the test compound is applied to a dosing well of a fluidics device. In step 510, a fluid EC50 for an effect on the cell culture for at least one of the plurality of wells is determined. Subsequently, in step 520, the at least one fluid EC50 is compared to a static EC50 for the effect on the cell culture determined for the test compound in a static system. Following step 520, at least three determinations are possible: a lower value of the at least one fluid EC50 relative to the static EC50 is determined 522, a higher value of the at least one fluid EC50 relative to the static EC50 is determined 524, or a substantially similar value of the at least one fluid EC50 relative to the static EC50 is determined 526.

Figure 28:
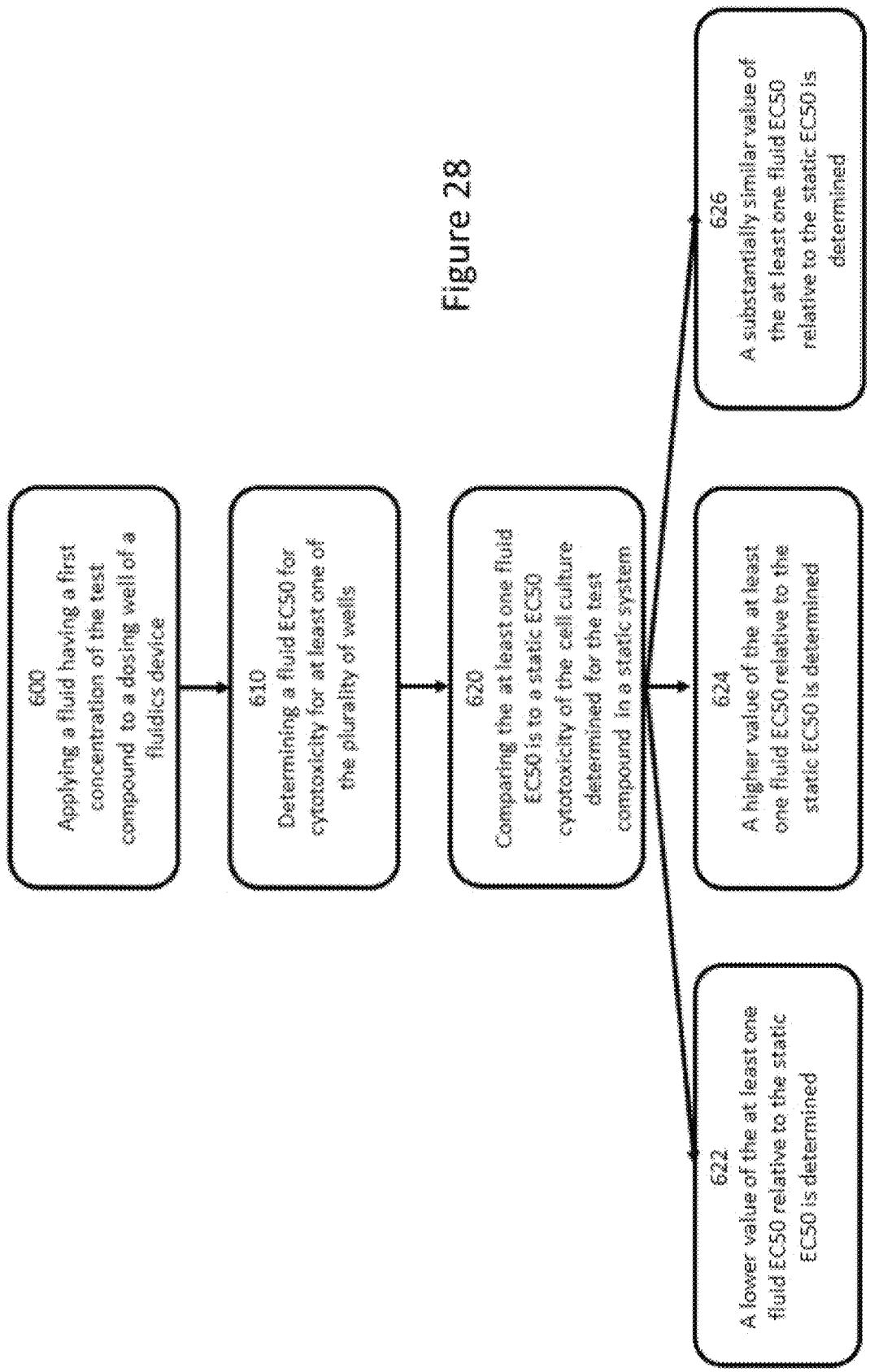
FIG. 28 is a flow diagram showing the steps of one embodiment of the in vitro assay method for predicting cytotoxicity of the cell culture.

Alternatively, in accordance with one or more embodiments of the presently disclosed subject matter, an in vitro assay method for predicting cytotoxicity of a cell culture in response to a test compound is provided. FIG. 28 is a flow diagram showing the steps of one embodiment of the in vitro assay method for predicting cytotoxicity of the cell culture. In step 600, a fluid having a first concentration of the test compound is applied to a dosing well of a fluidics device. In step 610, a fluid EC50 for cytotoxicity for at least one of the plurality of wells is determined. Subsequently, in step 620, the at least one fluid EC50 is compared to a static EC50 for cytotoxicity of the cell culture determined for the test compound in a static system. Following step 620, at least three determinations are possible: a lower value of the at least one fluid EC50 relative to the static EC50 is determined 622, a higher value of the at least one fluid EC50 relative to the static EC50 is determined 624, or a substantially similar value of the at least one fluid EC50 relative to the static EC50 is determined 626.

FIG. 27 is a flow diagram showing the steps of one embodiment of the in vitro assay method for predicting the effects on the cell culture. FIG. 28 is a flow diagram showing the steps of one embodiment of the in vitro assay method for predicting cytotoxicity of the cell culture. In each of the method embodiments described herein, a fluidics device may be used to perform at least portions of the in vitro assay method. In any of these method embodiments, any of the fluidic device embodiments described supra may be used. For example, in one embodiment, the fluidics device includes a plurality of wells for containing the fluid, each downstream well positioned lower relative to each adjacent upstream well, wherein each of the plurality of wells has a cell culture therein; and a dosing well upstream from the plurality of wells and in fluid communication therewith. In another example, in an alternative embodiment, the fluidics device includes the dosing well positioned upstream from a plurality of wells for containing the fluid, wherein the plurality of wells have a cell culture therein; and one or more channels extending between the adjacent upstream and downstream wells to define a fluid flow channel there between such that the fluid deposited into the dosing well flows to the respective fluid of the adjacent downstream well along the fluid flow channel there between, and the respective fluid subsequently flows to each adjacent downstream well along the fluid flow channel there between.

Numerous additional examples and embodiments of the fluidics device described herein, as well as combinations of these embodiments, may be used in the method embodiments described herein. As examples of, and not limitations to, such embodiments of the fluidics device, the fluidics device may include one or more of the following: each adjacent downstream well of the fluidics device being oriented in a step-down position relative to its adjacent upstream well; the plurality of wells of the fluidics device being aligned in a row; the plurality of wells of the fluidics device comprising at least 8 wells in a respective row and a total of at least 2 rows; a wick downstream from at least a portion of the plurality of wells for regulating fluid flow through the plurality of wells and/or in fluid contact with the fluid flow channel for regulating fluid flow through the plurality of wells; a collection well downstream from the plurality of wells for collecting fluid overflow from the downstream well furthest from the dosing well; a wick contained in the collection well for regulating fluid flow through the plurality of wells; a collection well having a floor defining a divot, wherein the floor is angled such that the divot is defined at a lower portion of the floor; a collection well channel extending from a fluid flow channel to a bottom of the collection well such that the respective fluid of the adjacent upstream well flows along the fluid flow channel and through the collection well channel into the collection well; a dosing well channel extending from a bottom of the dosing well to a fluid flow channel such that the dosing fluid flows to the respective fluid of the adjacent downstream well through the dosing well channel and along the fluid flow channel; a channel of the fluidics device having a width ranging from 10 to 3500 microns and a depth of 10 to 1500 microns; a channel of the fluidics device defines a triangular-shape extending between each of the adjacent wells and generally converging at each adjacent downstream well; a channel of the fluidics device comprises 2, 3 or 4 microchannels contiguous with the triangular-shape channel, and each of the microchannels having a width ranging from 200 to 750 microns and a depth of 10 to 1500 microns.

Furthermore, in the method embodiments described herein, the fluidics device may be used in conjunction with at least one of the following: a cover tray, a reservoir tray, additional fluidics device(s), at least one piston assembly, or at least one robotic liquid handling apparatus. For example, FIG. 8 shows an exploded perspective view of the fluidics device of FIG. 1 as part of an assembly including a reservoir tray nestably engaged on top of the fluidics device and a cover tray nestably engaged on top of the reservoir tray in accordance with embodiments of the present disclosure. Furthermore, in alternative embodiments, FIG. 25 shows a side view of the fluidics device as part of an assembly including a cover tray, a reservoir tray nestably engaged on top of the fluidics device, and a second reservoir tray nestably engaged underneath the fluidics device. Additionally, in alternative embodiments, FIG. 26 shows a side view of the assembly of FIG. 25 further including two additional fluidics devices in nestable engagement. FIGS. 19-24, for example, show various embodiments of a piston assembly.

In embodiments such as the method embodiment depicted in FIG. 27, the effect on the cell culture may include one or more of pharmacokinetics, drug metabolism, toxicity, cell receptor response, cell feedback signals, cell growth, cytotoxicity, cell differentiation, or cell regeneration. In additional embodiments, additional effects of the cell culture may be apparent to one skilled in the art in light of the disclosure herein. For example, one skilled in the art may want to predict the effects of the cell culture's tempered exposure to the dosing fluid during pre-clinical pharmaceutical studies and/or experiments involving upregulation or downregulation of factors, cytokines, cell responses, cell receptor responses, cell feedback signals or cell growth.

In one embodiment, depicted in the flow diagram of FIG. 28, the effect on the cell culture is cytotoxicity of the cells of the cell culture. In another embodiment, the plurality of wells contain a respective cell culture, whereby an effect of the tempered exposure to the fluid having a first concentration of the test compound on the cell culture can be analyzed.

In the embodiments described herein, the cell culture may include any of the cell cultures described supra and/or may include one or more of: a tumor cell line (e.g., an immortalized cell line derived from a tumor); primary hepatocytes; stem cells; progenitor cells; differentiated products of stem cells; primary cells or tissues from liver, kidney, lung, heart, muscle, brain, pancreas or thyroid; a HepG2 cell line culture; a HepaRG cell line culture; or a cell culture derived directly from human, dog, non-human primate, mouse or rat tissue cultured in 2-dimensional or 3-dimensional formats. For example, the cell culture may include a HepG2 cell line culture (e.g., in 2-dimensional or 3-dimensional formats such as a spheroid).

In some embodiments, the wells 120 of any row in a fluidics device may include different cell cultures for emulating in vivo environments or exposures. The capability of evaluating the downstream parameters and effects of one cell culture in response to an upstream cell culture's interaction with the fluidic environment is a signification advantage of the present invention. Any of the methods and devices described herein may be employed and applied to differing cell cultures arranged within a row of the fluidics device 100. Static systems cannot accurately predict the effects of chemical exposures on human cells and tissues. The fluidics device 100 described herein may be arranged to better evaluate the effects of corrosive/caustic chemicals on human systems in multiple industries. The methods described herein may be employed to help establish lower exposure limits (LEL), upper exposure limits (UEL), recommended exposure limits (REL), and Occupational Safety and Health permissible exposure limits (PEL). Advantageously, the significance of a corrosive resistant fluidics device 100, as is provided herein, stems from at least three major advances over current technologies: 1) dramatically improved biological relevance due to the fluidic and non-linear exposure gradients; 2) ability to test corrosive chemicals at higher doses for longer periods of time without degradation of the tissue culture plate and exposure of the cells to the plastic breakdown products; 3) compatibility with bioassays such as high content imagers and plate readers due to the optical properties of the glass-like plastic polymers and SBS compliant plate format.

In step 500 of FIG. 27 and step 600 of FIG. 28, a fluid having a first concentration of the test compound is applied to a dosing well of a fluidics device. In alternative embodiments, the fluid may be applied to a source well, another fluidics device, a piston assembly, or a robotic liquid handling apparatus. The fluid may include any of the dosing fluids described supra, the dosing fluid including a concentration of the test compound. The test compound may include one or more of one or more of drug, a legal or illegal drug, a toxin, an agent of warfare, a tracing compound, a fragrance, a food spice, an oil, a gas, a metabolite, a compound, a hormone, a solution, a solute, a composite, a nutraceutical, a nutrient media, differentiation media, or a growth media with varying dissolved oxygen levels.

The step 500, 600 of applying the fluid having the first concentration of the test compound to the dosing well may be repeated using a specific volume at determined intervals over a specified period of time. The specific volume may be used to define the rate at which the total fluid turnover in each well, the fluidics device as a whole, or a portion of the fluidics device occurs. For example, if the fluidic device holds a total volume of 1400 µL, then adding a specific volume of 50 µL during each application step 500, 600 would result in a slower turnover rate than adding a specific volume of 300 µL. Depending on the effect being measured, the test compound being used, the cell culture being used or the predictions desired, the specific volume, and therefore the turnover rates, will vary. In one embodiment, the specific volume is a value between 1 µL and 1500 µL. Further, the specific volume desired may correlate to the determined intervals and/or the specified period of time, both of which additionally may depend on the effect being measured, the test compound being used, the cell culture being used or the predictions desired. For example, in the aforementioned example, to achieve a similar fluid turnover result, adding a specific volume of 50 µL during each application step 500, 600 would require additional determined intervals and/or a greater specified period of time. In one embodiment, the specific volume is between 1 uL and 1500 uL and the determined intervals are once every 4 hours or 8 hours. In another embodiment, the specified period of time is 24 hours, 48 hours, 72 hours, or 120 hours. Any range of determined intervals or specified periods of time may be used.

Further, the application step 500, 600 may be performed manually or automatically, automation being performed using a robotic liquid handling apparatus, a piston assembly nestably engaged with the fluidics device, a cover tray in combination with a wick, or using other embodiments described herein. Additionally, as fluid is repeatedly being added, excess fluid may need to be removed to prevent spillage or overflow amongst the wells. In some embodiments, the methods described herein may include the additional step of syphoning fluid from the downstream well furthest from the dosing well when the step of applying the fluid is repeated. The additional step of syphoning fluid may be performed manually or automatically, automation being performed using a robotic liquid handling apparatus, a piston assembly nestably engaged with the fluidics device, a reservoir tray in combination with a wick, or using other embodiments described herein. In some embodiments, in which the application step 500, 600 is being performed, syphoning may not be necessary; instead, a collection well, an overflow structure, or additional fluidics devices may permit excess or overflow to properly accumulate without affecting the performance of the in vitro assay method.

In step 510 (or step 610), a fluid EC50 for an effect (or cytotoxicity) on the cell culture for at least one of the plurality of wells is determined. Subsequently, in step 520 (or step 620), the at least one fluid EC50 is compared to a static EC50 for the effect on the cell culture (or cytotoxicity of the cell culture) determined for the test compound in a static system. In step 522 (or 622), a lower value of the at least one fluid EC50 relative to the static EC50 is determined, which is predictive of the cell culture response to the test compound enhancing the effect (or cytotoxicity). In step 524 (or 624), a higher value of the at least one fluid EC50 relative to the static EC50 is determined, which is predictive of the cell culture response to the test compound diminishing the effect (or cytotoxicity). In step 526 (or 626), a substantially similar value of the at least one fluid EC50 relative to the static EC50 is determined, which is predictive of a cell culture response to the test compound substantially not affecting the effect (or cytotoxicity) or may not be predictive of the effect (or cytotoxicity). A cell culture response may be comprised of one or more of a pharmacokinetic response, a pharmodynamic response, metabolism of the test compound, metabolism of a fluidic component, cytotoxicity, cell receptor response, cell feedback signals, cell growth, cell differentiation, or cell regeneration.

A dose-response curve (or concentration-response curve) may be used to plot the results of many kinds of experiments; the X-axis of the dose-response curve plots the concentration of a substance (e.g., the test compound), whereas the Y-axis plots the response to the substance by a particular environment (e.g., the effect, cytotoxicity). Generally, the EC50 may simply be defined as the concentration of the substance (e.g., the test compound) that provokes the response (e.g., the effect, cytotoxicity) halfway between the bottom baseline and top maximum response. In other words, the EC50 may be considered a measure of the substance's potency. The IUPAC defines EC50 as the statistically derived median concentration of a substance in an environmental medium expected to produce a certain effect in 50% of test organisms in a given population under a defined set of conditions. General guidelines for EC50 determinations can be found in the publication by J. L. Sebaugh entitled "Guidelines for accurate EC50/IC50 estimation", found in Pharm Stat. 2011 March-April; 10(2):128-34, which is incorporated herein by reference in its entirety.

In embodiments of the present invention, a fluid EC50 for an effect (or cytotoxicity) on the cell culture for at least one of the plurality of wells is determined. Further, in some embodiments, a static EC50 for an effect on the cell culture (or cytotoxicity of the cell culture) for the test compound in a static system is determined. In other words, the fluid EC50 may be determined for one or more individual wells of a fluid system of a fluidics device including a plurality of wells in fluid communication or connected by at least one fluid flow channel. In contrast, the static EC50 may be determined for one or more individual wells of a static system, the static system may or may not be included in a fluidics device, so long as the one or more individual wells are not in fluid connection or, if at least one fluid flow channel between the wells exists, the at least one fluid flow channel is not permitting fluid flow between the one or more individual wells.

In one or more embodiments the static EC50 may be determined by testing multiple concentrations of the test compound in the at least one individual well, or an average of individual wells, of a static system without fluid exchange. In one embodiment, the static EC50 may be determined using a sigmoid E max pharmacodynamics model generated from the magnitude of the effect (e.g., cytotoxicity) of at least five drug concentrations that are multiplied by the amount of time the cells are exposed. Although the generated model may include a sigmoid curve, in some embodiments a linear model may also be used. Similarly, the at least one fluid EC50 may be determined. Additional EC50 determination methods are found in the Examples outlined infra.

Various methods, some well-known in the art and some novel to this disclosure, may be used when determining the EC50s in steps 510 (or step 610) and/or step 520 (or step 620). In some embodiments, the in vitro assay method further includes the step of applying a tracing fluid having a known concentration of a detectable tracing compound to a second dosing well of the fluidics device in a separate row, thereby using the known concentration of the tracing compound as a standard curve to calculate a concentration of the test compound in each of the plurality of wells. In one embodiment, the tracing compound may be detectable by one or more of radioactivity, optically, fluorescence, luminescence, histochemistry, immunohistochemistry, or light absorbance. In another embodiment, the tracing compound may be fluorescein salt at a concentration between 0.5 uM and 5 uM as dissolved in cell culture media, the fluorescein salt being detectable by fluorescence excitation at wavelength between 470 nm and 490 nm emission between 515 and 535 nm in a plate fluorescence reading instrument.

In yet another embodiment, the tracing compound may be applied to any dosing well 110 for use in detecting the flow of a substrate, metabolite, etc. The tracing compound may be activated by cells during flow and could be used as a mass spectroscopy surrogate. The activation may result in fluorescence.

In other embodiments, the in vitro assay method further includes a cytotoxicity detection reagent present in the plurality of wells having a cell culture therein; in these embodiments, the step of determining the fluid EC50 may include detection of the cytotoxicity detection reagent. In one embodiment, the cytotoxicity detection reagent may be detectable by fluorescence. In another embodiment, the cytotoxicity detection reagent may comprise a reagent that fluoresces when bound to double stranded DNA, the cytotoxicity detection reagent detectable by fluorescence excitation at wavelength between 470 nm and 490 nm emission between 515 and 535 nm in a fluorescence plate reading instrument. In an alternative embodiment, the cytotoxicity detection reagent is detected by imaging the individual cells in a plate imaging device.

In alternative embodiments, the in vitro assay method further includes an effect detection reagent present in the plurality of wells having a cell culture therein; in these embodiments, the step of determining the fluid EC50 may include detection of the effect detection reagent. In one embodiment, the effect detection reagent may be detectable by fluorescence. In another embodiment, the effect detection reagent may be detectable by one or more of radioactivity, optically, fluorescence, luminescence, histochemistry, immunohistochemistry, or light absorbance. In an alternative embodiment, the effect detection reagent is detected by imaging the individual cells in a plate imaging device.

In step 520 (or step 620), the at least one fluid EC50 is compared to a static EC50 for the effect on the cell culture (or, for step 620, cytotoxicity of the cell culture) determined for the test compound in a static system. When the at least one fluid EC50 is determined using a tempered gradient in a plurality of wells connected by fluidics, one can compare it to the static EC50 in order to predict if the "measured effect" of a test compound is enhanced by biological activity or diminished; in other words, one can predict whether the cell culture response to the test compound results in the effect (or cytotoxicity) enhancing or diminishing. In one embodiment, a lower value of the at least one fluid EC50 relative to the static EC50 may be determined 522, 622, which is predictive of the cell culture response to the test compound enhancing the effect (or cytotoxicity). In another embodiment, a higher value of the at least one fluid EC50 relative to the static EC50 may be determined 524, 624, which is predictive of the cell culture response to the test compound diminishing the effect (or cytotoxicity). In another embodiment, a substantially similar value of the at least one fluid EC50 relative to the static EC50 may be determined 526, 626, which is predictive of a cell culture response to the test compound substantially not affecting the effect (or cytotoxicity) or may not be predictive of the effect (or cytotoxicity).

In some embodiments, by examining the trend of the fluid EC50 of the plurality of wells downstream from the dosing well in comparison with the static EC50, it may be predicted whether the interaction of the test compound with in vivo cells similar to the cell culture would diminish or enhance particular effects (e.g., cytotoxicity). For example, a lower value of the fluid EC50 from the at least one of the plurality of wells relative to the static EC50 may be predictive that cellular activity is enhancing the effect (e.g., cytotoxicity) of the test compound, whereas a higher value may be predictive that cellular activity is diminishing the effect (e.g., cytotoxicity) of the test compound. Furthermore, in some embodiments, these predictions may occur without any, or with a minimum of, a priori knowledge of the cellular activity occurring within the fluid.

The various in vitro assay methods described herein may be helpful in determining the effects resulting from the test compound being metabolized by the cell culture without requiring knowledge of the actual metabolism byproducts and processes occurring within the successive wells. In some experiments, it has been shown that as the test compound moves through successive wells of a fluidics device, the ratio of the test compound to the metabolic products produced by the cell changes. Metabolic products are being produced from chemical reactions in the cells directed at the test compound therefore reducing the concentration of the test compound and increasing the concentration of the metabolic products of the test compound. Therefore, in some embodiments, the fluid EC50 for cytotoxicity in each successive well of the plate may reflect at any moment in time the effects of a particular ratio of test to metabolite product.

In addition to systems and methods described herein, the present invention may also include features and/or method steps for controlling the fluid flow between wells 120 of the fluidic device 100. Notably, fluid may refer to a gas, a liquid or both. Bioassays may be performed on the liquid fluid within the fluidics device 100, the gaseous fluid within the fluidics device 100, or both. The wells 120 and/or dosing wells 110 may be segmented with an air/fluid interface through the use of a channel cover 230, a dosing well channel cover 160, a cover tray 260 or any other portion or component of the fluidics device 100.

By controlling the fluid flow between adjacent wells 120, the embodiments disclosed herein further control the exposure and non-exposure of downstream wells to the biological responses of upstream wells without disrupting the established gradient between wells 120. When the fluidic flow is sufficiently dampened or stopped, the present invention enables the user to sample, conduct analytical evaluations and/or comparatively evaluate the static interaction of a drug with a specific cell line using historical plate readers, imagers, and currently available fixed volume biochemistry assays. The pause in fluid flow will allow traditional assays to be completed in non-changing environments. A permanent stoppage of flow is less desired, as it is advantageous to temporarily block flow of the time-resolved fluids while sustaining gradients of chemical, toxicant, or cell metabolism, for example. Once measurements have been made, fluid flow can be restarted in the same channel by removing the blockage. The blockage may be a liquid and/or physical plug 700, 800 for stopping flow, which will effectively isolate the products of the bioassay within a well 120, preventing, or at least significantly reducing, leakage of fluidic media into the subsequent well. Minimal interference, or not interference at all, with the chemistry and/or media of the bioassay is desired when stopping and restarting flow. One goal of providing and/or using a physical plug 700 or liquid plug 800 is to be able to stop, or at least significantly dampen, fluid flow between wells 120 to perform a bioassay or analysis, and then re-start the flow in order to continue the experiment, allowing later time points to be evaluated once the wells are again fluidly engaged with each other.

In at least one embodiment of the present invention a physical plug 700 is provided to mechanically control flow amongst wells 120, channels 130 and/or microchannels 200 of a fluidics device 100. The physical plug 700 may be comprised of any number of non-permeable materials. For example, the physical plug 700 may be comprised of one of a polymer, a synthetic polymer, a biodegradable polymer, a plastic, a biodegradable plastic, a thermoplastic, a polystyrene, a polyethylene, a polypropylene, a polyvinyl chloride, a polytetrafluoroethylene, a silicone, a glass, a PYREX, a borosilicate, and combinations thereof. Further, the physical plug 700 may be coated with, or comprise an additional external layer of, any of these materials to define a deformable portion 710 for conforming the shape of the physical plug 700 to the shape of fluidics device 100 to which the plug 700 is engaged. The physical plug 700 and/or deformable portion 710 may be malleable enough to conform to a shape of the fluidics device 100, and in some embodiments compressible to conform even more closely to a shape, but may also be strong enough to withstand multiple engagements and disengagements without sustaining damage. Rubber coatings of various thicknesses, hardness, and chemical compositions may be used according to the shapes and uses desired.

Figure 42:
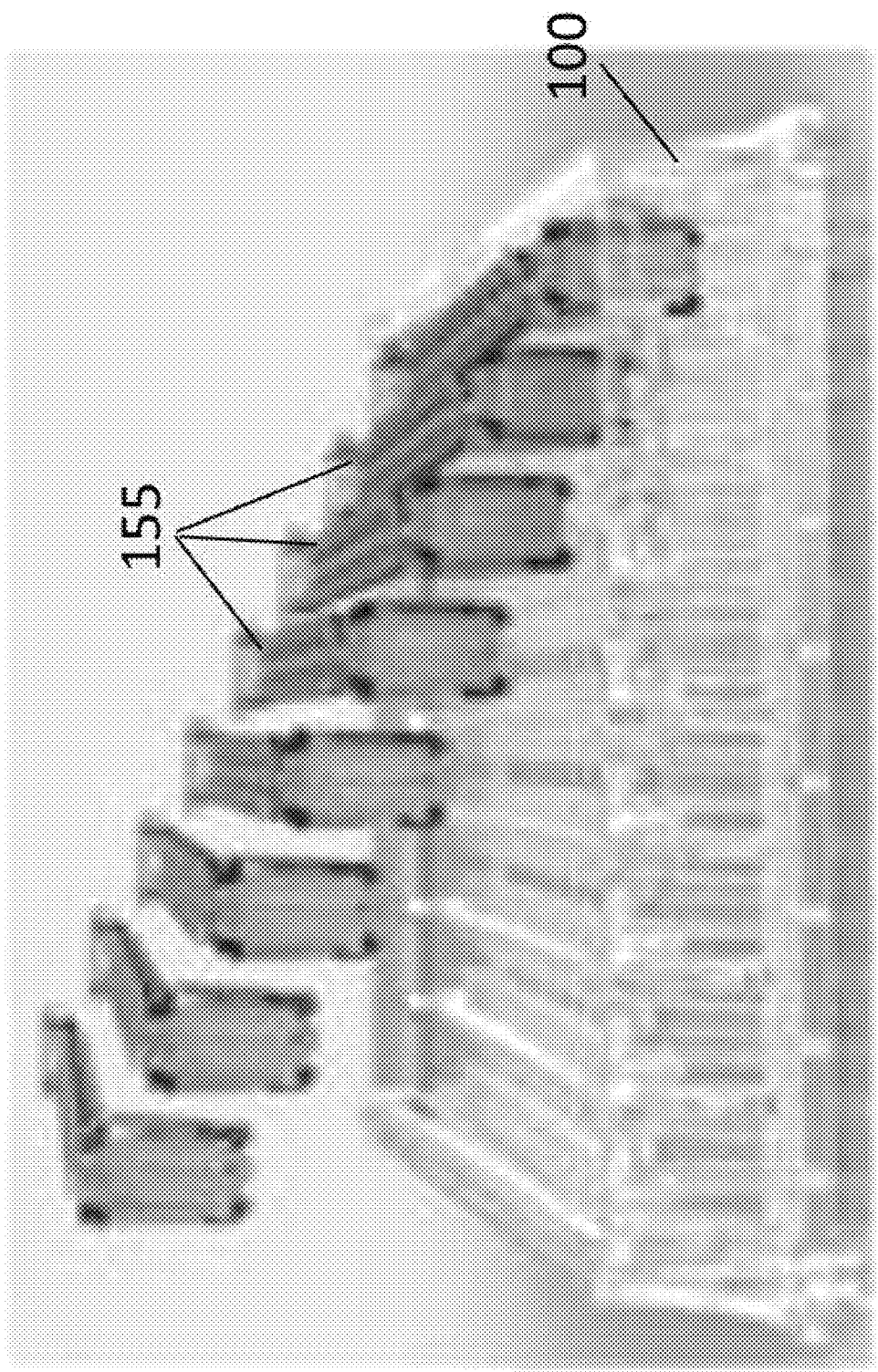
FIG. 42 depicts the rows of wells of a fluidics device according to one or more embodiments of the present invention.

As described supra, the fluidics device 100 may include a number of wells 120 interconnected by a fluid flow channel 130 and/or microchannel(s) 200. Further, the fluidics device 100 may contain a number of rows (see, e.g., FIG. 42). As is illustrated by FIGS. 41 and 42, the shape of the channels 130 may be defined by an insert 155 positioned within each row of the fluidics device 100. The channels 130 may be further defined by a channel cover 230 engaged with the insert 155 or the fluidics device 100 (see, e.g., FIG. 41). The channel cover 230 may define microchannels 200 therein or may merely cap the channel 130. The channel cover 230 may define microchannel apertures 205 in fluidic engagement with the adjacent wells 120 for accepting fluid flow therethrough. Further, the channel cover 230 may define a well engagement portion 235 for engaging an upper portion 125 of each well 120.

Figure 45:
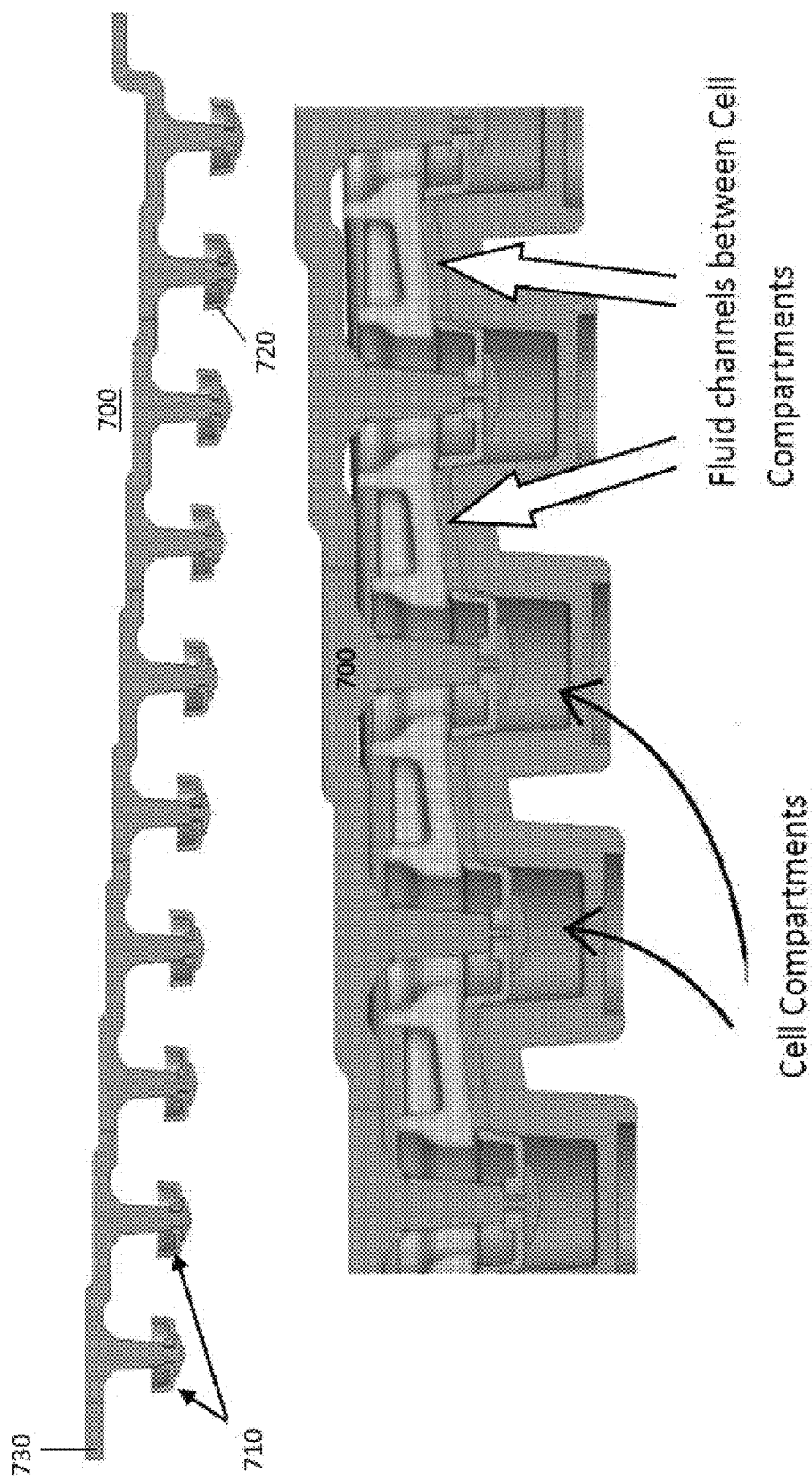
FIG. 45 depicts a physical plug for controlling fluid flow according to one or more embodiments of the present invention.

In order to dampen or stop fluidic flow from one well 120 to a downstream adjacent well 120, the physical plug 700, or deformable portion 710 thereof, may be shaped to sealingly engage the upper portion 125 of the well 120 of the insert 155 or fluidics device 100, the well engagement portion 235 of the channel cover 160, the channels 130 of the insert 155 or fluidics device 100, and/or the microchannel apertures 205 of the channel cover 230. For example, one embodiment of the invention may include the physical plug 700 illustrated in FIG. 45, which includes well engagement portions 235 shaped to sealingly engage the wells 120, thereby preventing fluidic engagement with the fluid channels 130, microchannels 200 or microchannel apertures 205.

In some embodiments the physical plug 700 may sealingly engage and/or prevent fluidic flow of at least one well 120, at least one row of wells 120, at least one column of wells 120, an assortment of wells 120, or each well 120 of the fluidics device 100. The sealing engagement and/or prevention of fluidic flow may be provided in part or in whole by the deformable portion 710 of the physical plug 700. In some embodiments the deformable portion 710 may be unitary in construction or may be in the form of a spray-on application applied to a surface of the physical plug 700. In other embodiments, the deformable portion 710 may be comprised of a plurality of discrete portions.

A method of using the fluidics device 100 may include the engagement and/or disengagement of the physical plug 700 with the fluidics device 100. For example, the physical plug 700 may define at least one insert engagement aspect 720 for engaging at least one well 120. The engagement of the insert engagement aspect 720 to the corresponding well 120 may be effected using applied pressure to the physical plug 700. The well 120 and the insert engagement aspect 720 may be advantageously shaped to permit selective engagement of the two 120, 720 such that minimal force is required yet the two 120, 720 are effectively engaged to control fluidic flow. In one embodiment, the physical plug 700 may be first engaged to the most downstream well 120, then each subsequent upstream well 120, while in another embodiment the physical plug may be first engaged to the dosing well 110 then to each subsequent downstream well 120. Some embodiments of the physical plug 700 may include or define a tab 730 on one or both ends for easier disengagement of the plug 700 from the fluidics device 100. As with engagement, disengagement of the plug 700 may be performed sequentially along the row in either direction, or may be performed substantially simultaneously using a leveraged motion.

In some embodiments, the method of using the fluidics device 100 may further include steps of removing liquid from one or more wells 120 before applying the physical plug 700 and/or may include steps of adding liquid to the one or more wells 120 after disengaging the physical plug 700 from the fluidics device 100. Further, sterilization of the physical plug 700 may be necessary before engaging the fluidics device 100. Because application of the physical plug 700 of some embodiments to the fluidics device 100 may result in displacement of fluids, removal of fluids may be desired to prevent any increase in pressure to either alter the chemistry or cells of the fluid or to prevent overflow of the fluids. In some embodiments, displacement of fluids may safely occur without the additional step of removing fluids by employing a physical plug 700 defining a shape for permitting displacement of fluids therein. For example, in an embodiment wherein the physical plug 700 includes a well engagement aspect 720, the bottommost side of the well engagement aspect 720 may be concave in shape to permit displacement of fluids therewithin.

In at least one embodiment, the physical plug 700 may be forced to engage the fluidics device 100 or forced to increase engagement with the fluidic device 100 through the use of a switch, lever or other actionable item for applying pressure to the physical plug 700. Applying pressure to the physical plug 700, in at least the direction of the fluidics device 100, may cause the deformable portion 720 of the plug 700 to more snugly engage the fluidics device and/or create a greater seal for controlling the flow of the fluids. In one embodiment, the physical plug 700 may be embodied within, or engageable to, the channel cover 230 for applying pressure to the portion of the channel cover forming the microchannel(s) 200, and thereby closing the fluid flow within the microchannel(s) 200, when the actionable item is translated or rotated. For example, a wedge-shaped physical plug 700 may be rotated such that an apex of the wedge is forced into position immediately above at least one microchannel 200 within a channel cover 230, thereby forcing the channel cover 230 to collapse and close the microchannel(s) 200 and prevent fluid flow therethrough.

In at least another embodiment of the invention, a liquid plug 800 may be provided for controlling the flow of liquid between wells 120, channels 130 and/or microchannels 200. The liquid plug may be a liquid having a higher viscosity than the media of the fluidics device 100 or, alternatively, may be a liquid capable of changing to a more viscous state upon proper stimulation (e.g., agar when experiencing a decrease in temperature). The method of using a fluidics device 100 may further include additional steps for using the liquid plug 800 for controlling the flow of liquids.

In some embodiments, the method of using the fluidics device 100 may further include steps of removing liquid from one or more wells 120. Subsequently, the liquid plug 800 may be added to one or more of the wells 120. In one embodiment of the method, the liquid from an entire well 120 may be removed and replaced with the liquid plug 800. In some embodiments, the liquid of every other well 120 of a row may be replaced with the liquid plug 800 to control the flow of liquids between the wells 120, channels 130 and/or microchannels 200. In wells 120 where the liquid plug 800 replaces the media of the well 120, the cell culture of the well 120 may be sacrificed. The inter-well method (see FIG. 44) of using the liquid plug 800 to replace the liquid media may also include alternating the wells 120 in which the liquid plug 800 is used in adjacent rows of the fluidics device 100. In this manner, alternate cell cultures may be sacrificed, as opposed to sacrificing only cell cultures of wells 120 of the same column, so that data may be replicated across the rows and be interpolated to the sacrificed wells 120.

In other embodiments, the method of using a fluidics device 100 may include removing only a portion of the liquid from one or more wells 120. Enough liquid may be removed so that the liquid remaining in the well 120 is below the channel 130 or microchannel 200 level, thereby weakening the capillary and surface energy forces wicking the liquid from one well 120 to an adjacent downstream well 120. Although the capillary and surface energy forces are weakened when the liquid media is withdrawn, they may still exist to such a degree as to provide some fluidic flow. To further control the flow of the liquid, the liquid plug 800 may be added to each well 120 from which liquid was drawn. In some embodiments, the liquid plug 800 may flow through the channels 130 and/or microchannels 200 via capillary action, thereby controlling the flow of the liquid media between the wells 120. In other embodiments, the liquid plug 800 may also be added to one or more channels 130 or microchannels 200 engaging the wells 120 from which liquid was drawn. This intra-well method (see FIG. 43) of using liquid plugs 800 to 'cap off' wells 120 from which liquid was drawn permits a user to take advantage of the differing refractory indices between the liquid media and the liquid plug 800 when reading the fluidics device wells 120 from the bottom. For example, when detecting fluorescence, the detection of the fluorescence may be enhanced by the mirror-like effect of the change in refractory indices—at the interface/boundary of the liquid plug 800 and the liquid media. In some embodiments, the liquid plug 800 may be optically clear or minimally opaque.

In any of the embodiments described supra, the liquid plug 800 may be, for example, olive oil, baby oil, mineral oil, canola oil, glycerin, glycerol, gelatin, agar or a combination thereof. Liquid plugs 800 of differing viscosities, densities, surface tensions, and cohesive forces may be used. To achieve maximum effectiveness, the liquid plug 800 may be capable of overcoming both gravity-driven and capillary-driven fluidic forces, thereby ensuring that the liquid plug 800 remains layered above the liquid media of the well 120 once settled and resists flow between the wells 120, channels 130 and microchannels 200, preferably to the point of being inert. Compared to the physical plug 700, the liquid plug 800 generally has the advantage of having a lower risk of contamination of the culture and media in the well, as well as of permitting greater flexibility with plate reader analyses. Like the physical plug 700 though, the user may ensure that the liquid plug 800 is sterile, as well as biocompatible, to avoid contaminating the liquid media and/or damaging the long-term viability of the cell culture.

Liquid media and/or liquid plug 800 may be added in any number of ways to perform the steps described herein. For example, a pipette may be used to add liquid media or liquid plug 800 to at least one well 120, channel 130 or microchannel 200. The pipette's control of volume to be disposed may be controlled manually, digitally or mechanically. In some embodiments, a piston assembly 300 similar or the same as the assemblies 300 described herein may be provided to add liquid media or liquid plug 800 to the fluidics device 100.

Liquid media and/or liquid plug 800 may be removed in any number of ways to perform the steps described herein. When removing liquid media, care is taken not to disturb the cell cultures of the wells 120 and the gradient between wells. When removing liquid plug 800 care is taken not to remove or disturb not only the cell cultures and gradient, but the liquid media in which they reside. In at least one embodiment, a pipette may be used to remove liquid plug 800 from at least one channel 130 and/or microchannel 200, to remove the layer of liquid plug 800 residing above the liquid media of at least one well 120, and/or to remove the liquid plug 800 from within a well 120. In order to effectively handle the higher viscosity of the liquid plug 800, the pipette may be a large bore pipette or a positive displacement pipette. In other embodiments, a wick may be used to draw liquid media or liquid plug 800 from each well individually. Alternatively, when removing liquid plug 800, a wick or a vacuum may be positioned in the most downstream well or the reservoir to draw liquid plug 800 through the channels 130 and/or microchannels 200 so that a sufficient amount of the liquid plug 800 is removed. In such an embodiment, once a sufficient amount of the liquid plug 800 is removed, liquid media may be added into at least one well 120. Once the liquid media and liquid plug 800 settle, as is necessary whenever either is added to the fluidics device, the additional liquid media effectively raising the layer of liquid plug 800 still remaining so that the remaining layer of liquid plug 800 is able to be wicked or vacuumed. In yet another embodiment, the liquid plug 800 may be removed through the use of a plug chemical for dissolving the liquid plug 800 and/or reducing the viscosity of the plug 800 held within the fluidics device 100.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

EXAMPLE 1

Title. Examining the Effects of Tamoxifen on HepG2 Cells Comparing Cytotoxicity between Several Experimental Approaches.

Introduction.

A new paradigm in predictive toxicology includes assessment of early initiating cellular events due to toxicant or drug exposure. One of the major challenges of this paradigm is determining whether such initiating events are adaptive or will lead to toxicity. Cell culture models that relate cellular events, such as changes in mRNA levels, with cytotoxic outcomes are often used to distinguish an adverse response from an adaptive response. The exposure levels required to produce each of the responses is then extrapolated to probable in vivo exposure scenarios through dose-response curves.

The fluidics device is a versatile system that enables application of fluidic motion and gradient toxicant exposure to cell-based assays. Time-resolved dynamic exposure scenarios afforded by the fluidics device is more in vivo-like and could enable more accurate assessment of adaptive versus toxic mechanisms. Moreover, the dynamic exposure scenario allows ascertainment of actual thresholds rather than extrapolating from endpoint dose-response curves.

To demonstrate the use of the fluidics device and the effects of gradient exposures on cytotoxicity, we conducted a series of experiments examining the effects of Tamoxifen on HepG2 cells comparing cytotoxicity between several experimental approaches.

Materials and instruments used include: HepG2 Cells; at least one fluidics device; culture media including DMEM supplemented with 10% FBS, 1× Glutamax, 1× Pen/Strep; CellTox™ Green; Tamoxifen dissolved in DMSO; Fluorescein salt; Tecan Infinite M1000 Pro Multimode plate reader.

Methods.

Optimizing Z-height focus in the Tecan Infinite M1000 Pro. The fluidics device is an SBS formatted microtiter plate designed to be compatible with plate-readers, imagers, and automated liquid handling. In order to enable gravity pull of fluids across the fluidics device, it was designed with well-heights elevated at one end of the plate and subsequently each well is 0.5 mm lower. As such the distance between the bottom of the wells in column 2 of the fluidics device is 6 mm higher than the bottom of well in column 11. The Tecan Infinite M1000 Pro features the ability to empirically determine the optimal height of each measurement and therefore negate the effects of well height on measurements.

To determine optimal height for measurement of CellTox™ Green, HepG2 cells were plated to the wells of the fluidics device and then lysed with detergent in the presence of CellTox™ Green. In each well this caused maximal CellTox™ Green fluorescence that served as a focal point for optimizing z-height. The z-heights determined for the fluidics device are listed in FIG. 32. To improve speed of analysis, subsequent experiments used this set height parameter rather than optimizing with each read.

Creation of a Fluorescein Standard Curve.

The fluidics device is designed to allow application of a toxicant in a specified source well from which a combination of gravity, surface tension, and diffusion causes the toxicant to flow to downstream wells. Because the concentration is changing in each well over time, to determine the concentration of toxicant or drug at any given time for data analysis requires co-application of a standard. Fluorescein salt is a relatively non-toxic dye that does not penetrate the plasma membrane and is commonly used as a medical and environmental tracer dye (reference). To utilize Fluorescein as a tracer dye, a standard curve of known fluorescein concentrations is created. This standard curve creates a line equation where experimental fluorescent readings are used to calculate an absolute fluorescein concentration. This experimental concentration is then multiplied by the starting concentration of experimental substrate to obtain the level of each at any given time in the experiment.

To create the Fluorescein standard curve, each row of the fluidics device was filled with a single concentration from 0.001 uM to 1 uM of Fluorescein dissolved in complete media. Plate was then read at ex485/em525 using the Tecan Infinite M1000 Pro using z-heights in FIG. 32. The instrument was set to determine optimal gain settings for the 1 uM dilution. The values from each row were averaged and plotted against concentrations resulting in a linear standard curve (see FIG. 33). The equation for this curve was determined using linear regression analysis. Gain settings were recorded for use in later experiments.

Figure 39:
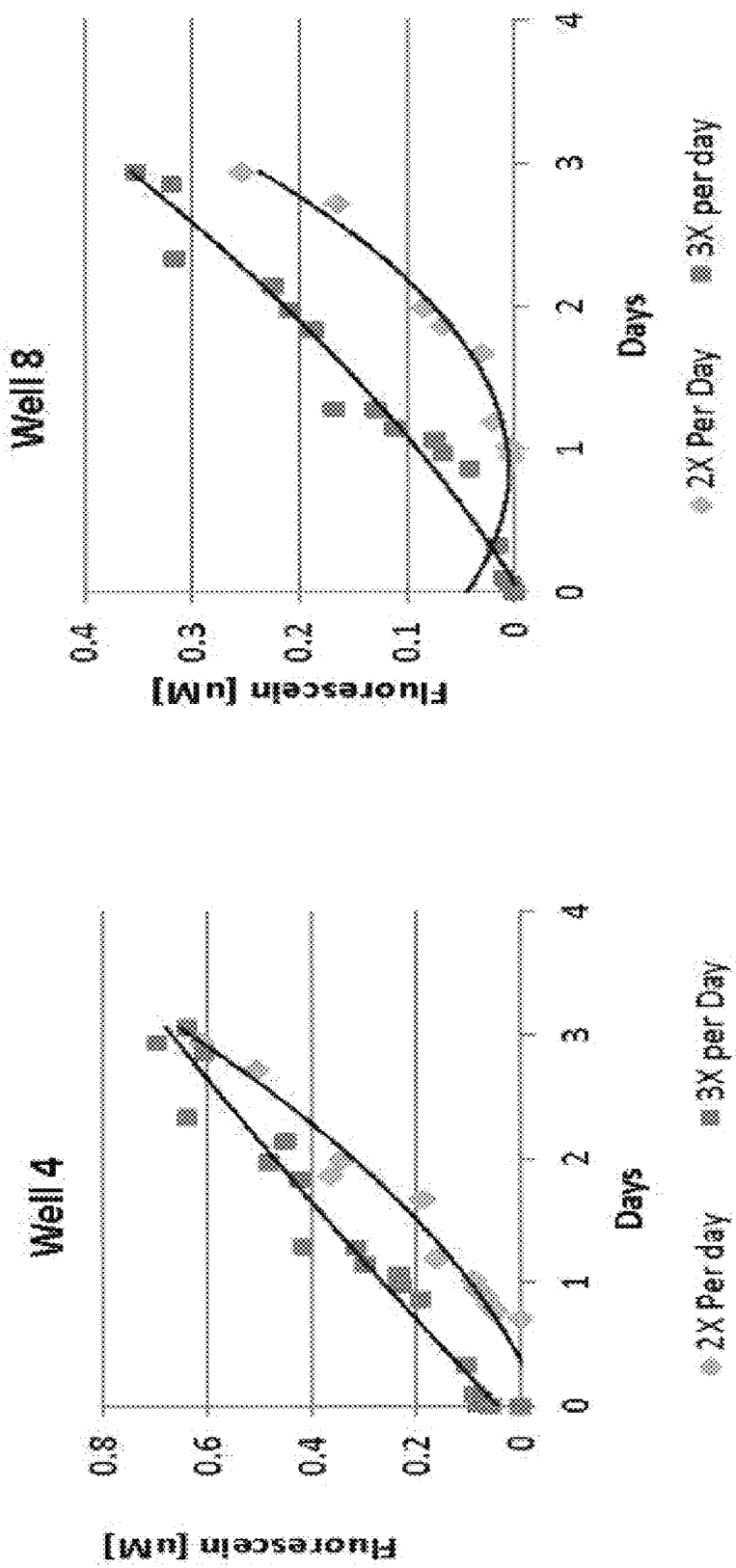
FIG. 39 depicts Fluorescein concentrations in two wells plotted over 72 hours.

User-defined dynamics of exposure using the fluidics device. Because the fluid is moving towards a state of equilibrium, it is important to replenish the source well at defined intervals to maintain fluid flow in the system. The cadence of replenishment determines how quickly toxicant moves through the system. To demonstrate the effect of replenishment cadence on gradient formation, the wells of the fluidics device were filled with 100 uL complete media in wells 2-11. 400 uL of media was added to the source well followed by 200 uL of 1 uM Fluorescein. Fluorescein concentration was monitored over time using a Tecan Infinite Pro 1000 plate reader set for ex/em 485 nm/525 nm. To replenish the system, 100 uL of media was removed from well 11 and 100 uL 1 uM Fluorescein was added to the source well. This was repeated either two or three times per day. FIG. 39 depicts Fluorescein concentration curves in representative wells 4 and 8 according to replenishment cadence over 72 hours. Replenishing 3× per day resulted in more significant concentration rise as compared to 2× per day.

Figure 40:
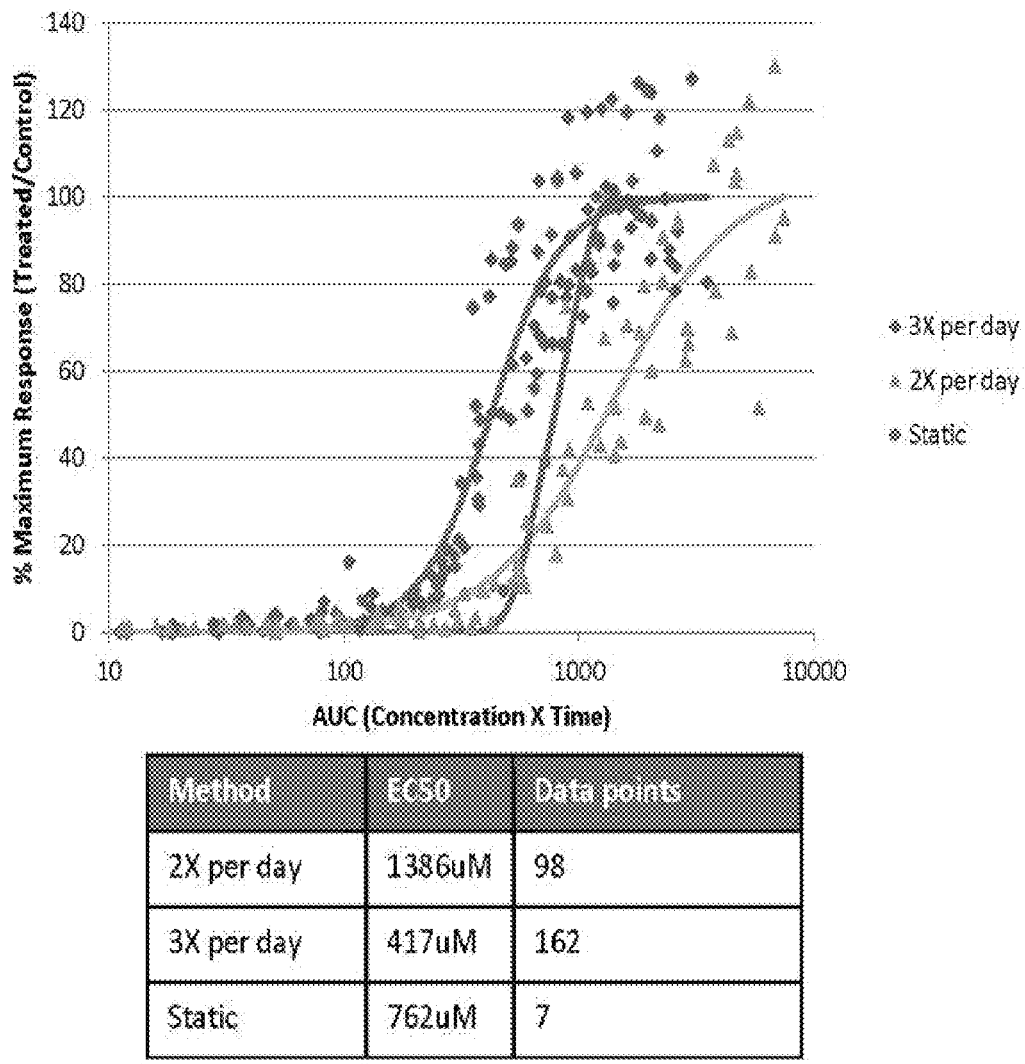
FIG. 40 depicts the effect of flow on HepG2 response to Tamoxifen.

Effect of Flow Rate on Response of HepG2 Cells to Tamoxifen using CellTox™ Green. To compare the effects of flow on response of HepG2 cells to Tamoxifen, cells were treated in the wells of the fluidics device where the drug was applied either to the source well at two different rates (2× and 3×), or was applied directly to individual wells in the absence of flow (static). For each condition, HepG2 cells were seeded into the individual wells of the fluidics device at a density of 30,000 cells per well in 50 uL media. This density corresponded to approximately 60% confluence. FIG. 40 depicts the effect of flow on HepG2 response to Tamoxifen, including the concentration multiplied by time effect of cytotoxicity of Tamoxifen. HepG2 cells in a fluidics device were treated with increasing concentrations of Tamoxifen over time. 150 uM of Tamoxifen was infused into the source well of the fluidics device either 2 times per day (2×) or three times per day (3×). Two acellular rows were infused with 1 uM Fluorscein to enable calculation of absolute concentration at any given time. The reagent CellTox™ Green was used to monitor cellular toxicity. Area under the curve values for each timepoint were obtained and plotted against effect expressed as a % maximum of (treated/control). Data was pooled together to obtain a single plot. EC50 values were calculated by a Sigmoid EMax model in PKSolver.

Flow-based Treatment. For the 2× and 3× experiment, to utilize Fluorescein as a standard for concentration, rows A and B remained acellular. After acclimating one day, media was changed to media containing a 1:2000 dilution of CellTox™ Green using volume of 100 uL per well. 400 uL of CellTox™ Green containing media was also added to the source well. Fluidic connections were allowed to form and stabilize for 30 minutes at 37° C. in a humidified incubator. Once fluid connections in each row was confirmed, 200 uL of media containing CellTox™ Green with either 150 uM Tamoxifen in 0.1% DMSO or 0.1% DMSO alone was added to the source well. To rows A&B, 200 uL of 1 uM Fluorescein in 0.1% DMSO was added to the source well. For all conditions, fluorescence was monitored using a Tecan Infinite Pro M1000 multimode plate reader optimized for Z-heights focal plane. For the 2× and 3× plates, media flow was maintained by syphoning 100 uL from well 11 and applying 100 uL fresh dosing solution to the source well at cadence corresponding to twice pre day (2×) or three times per day (3×).

Static Treatments. For static fluid conditions, after seeding, cells acclimated for one day and then media was changed to 50 uL of media containing the noted concentration of Tamoxifen in 0.1% DMSO or 0.1% DMSO alone. Incubation proceeded for 24 hours where analysis of fluorescence determined the degree of cell death in each well. Nine replicates of each concentration were averaged.

Data Analysis. For determining the concentration at any given time in the 2× and 3× flow plates, the RFU values obtained from the a-cellular Fluorescein control rows were averaged for each column and an actual Fluorescein concentration was determined using the Fluorescein Standard curve (see FIG. 33). The starting concentration of Fluorescein was 1 uM and the starting concentration of Tamoxifen was 150 uM therefore, the amount of fluorescein in each well was multiplied by 150 to obtain the corresponding concentration of Tamoxifen. The area under the curve (AUC) for each timepoint was obtained by multiplying the concentration value by the time in hours since the last time point using the AUCt function in PKSolver. For static conditions, the concentration was constant for the entire treatment time, therefore to obtain AUC the concentration was multiplied by 24 hours. The effect level is obtained by dividing treated values by control values and normalizing to 100% maximum response. The "Sigmoid Emax" pharmacodynamics model in PKSolver was used to generate EC50 values and line-fits (see FIGS. 35-37). For more details, see Zhang, et al., "Computer methods and programs in biomedicine", 99 (2010) 306-314, which is incorporated herein by reference in its entirety.

Conclusions. Difference in curves between treatment in the fluidics device under flow conditions verses static culture provides an avenue to determining molecular mechanisms involved in cytotoxicity.

EXAMPLE 2

Title. Differences in Predicted EC50s Using Time-Resolved, Non-Linear Toxicant Exposure Compared to Static Exposures In Vitro.

Abstract. Standard 2-dimensional static cell culture systems are limited tools for toxicology evaluations in vitro. Cells grown in monolayers do not form appropriate cell-cell contacts and cells grown in static culture wells are subjected to increasing amounts of waste products and decreasing amounts of dissolved oxygen leading to potential stress responses and toxicity not related to the toxicant added. To overcome these limitations, researchers are turning to 3D scaffolds, spheroids, hydrogels, and fluidics systems to improve the physiological relevance of the environment to which cells are introduced. We show here the evaluation of a fluidics system engineered to connect 10-wells of each row in a 96-well plate together with a microfluidic channel. This system sequentially links wells together to form a cascade of cell chambers through which drugs or toxicants can be applied. Toxicants interact with cells in the upstream compartments creating metabolites that will mix and interact in downstream wells forming a parent-metabolite gradient in a time-resolved fashion. Such a system, enables concentration by time kinetics of toxicity measurements in a more life-like environment. To demonstrate the value of this system, we have evaluated the effects of Tamoxifen on HepG2 cells in comparison to static conditions using the reagent CellTox™ Green. Using a fluorescein tracer molecule we could demonstrate that exposures in the fluidic system were non-linear and shaped similar to an expected plasma curve in vivo. Comparisons of AUC between static and flow systems revealed dramatically different dose-response curve shapes and EC-50s with HepG2 cells in the flow system approximately 4 fold less sensitive to Tamoxifen than cells in static systems.

Background.

A new paradigm in predictive toxicology includes assessment of early initiating cellular events due to toxicant or drug exposure. One of the major challenges of this paradigm is determining whether such initiating events are adaptive or will lead to toxicity. Cell culture models that relate cellular events, such as changes in mRNA levels, with cytotoxic outcomes are often used to distinguish an adverse response from an adaptive response. The exposure levels required to produce each of the responses is then extrapolated to probable in vivo exposure scenarios through dose-response curves.

The fluidics device is a versatile system that enables application of fluidic motion and gradient toxicant exposure to cell-based assays. Time-resolved dynamic exposure scenarios afforded by the fluidics device is more in vivo-like and could enable more accurate assessment of adaptive vs toxic mechanisms. Moreover, the dynamic exposure scenario allows ascertainment of actual thresholds rather than extrapolating from endpoint dose-response curves.

To demonstrate the use of the fluidics device and the effects of gradient exposures on cytotoxicity, a series of experiments were conducted examining the effects of Tamoxifen and Acetaminophen (APAP) on HepG2 cells comparing cytotoxicity between several experimental approaches.

Objectives. Evaluate total time-resolved exposure cell death EC50 for Tamoxifen or Acetaminophen (APAP) treated HepG2 cells using a fluid culture of a fluidics device versus standard static fluid culture.

Figure 29:
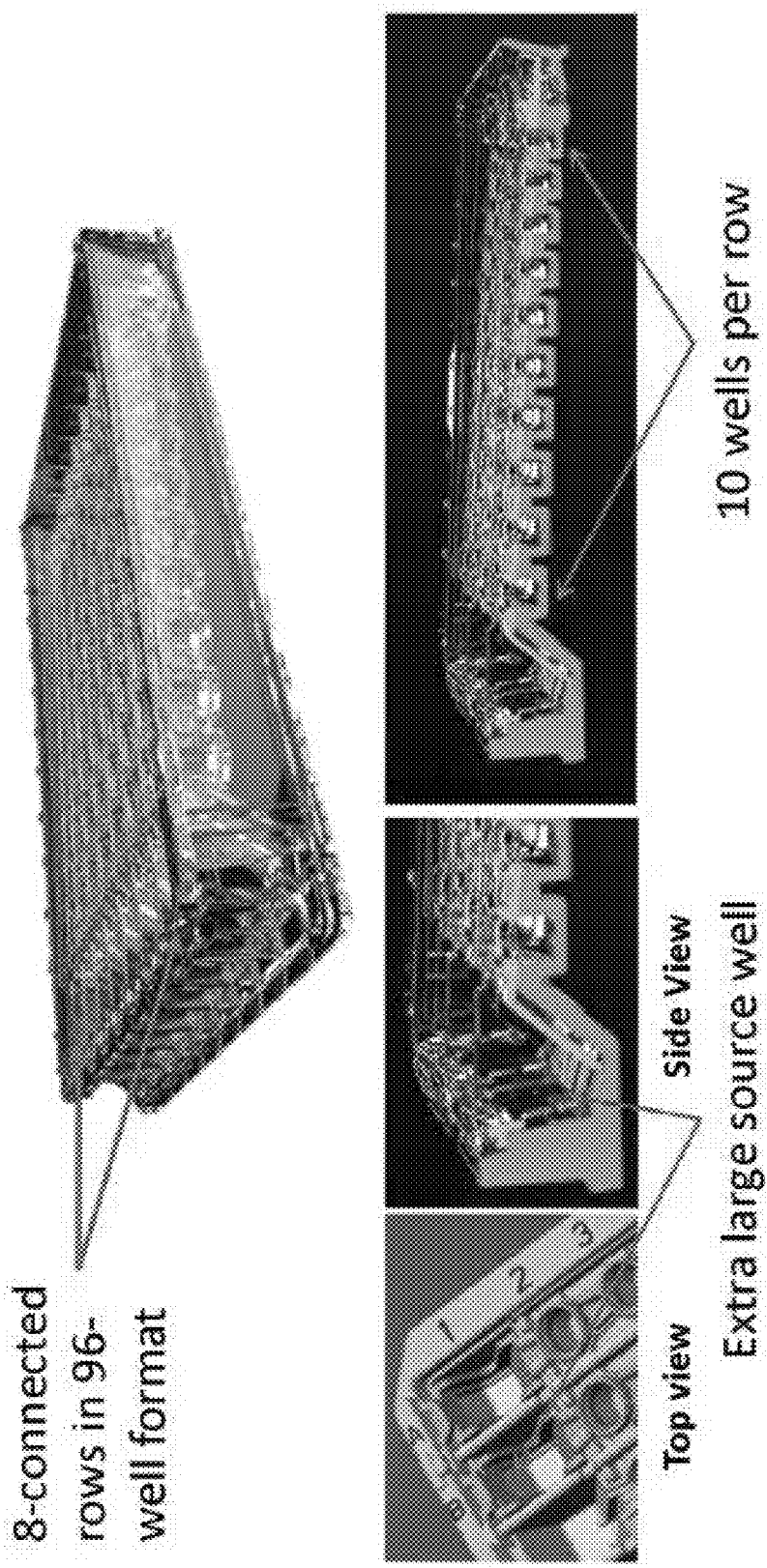
FIG. 29 depicts the design features of the fluidics device used in EXAMPLE 2.
Figure 30:
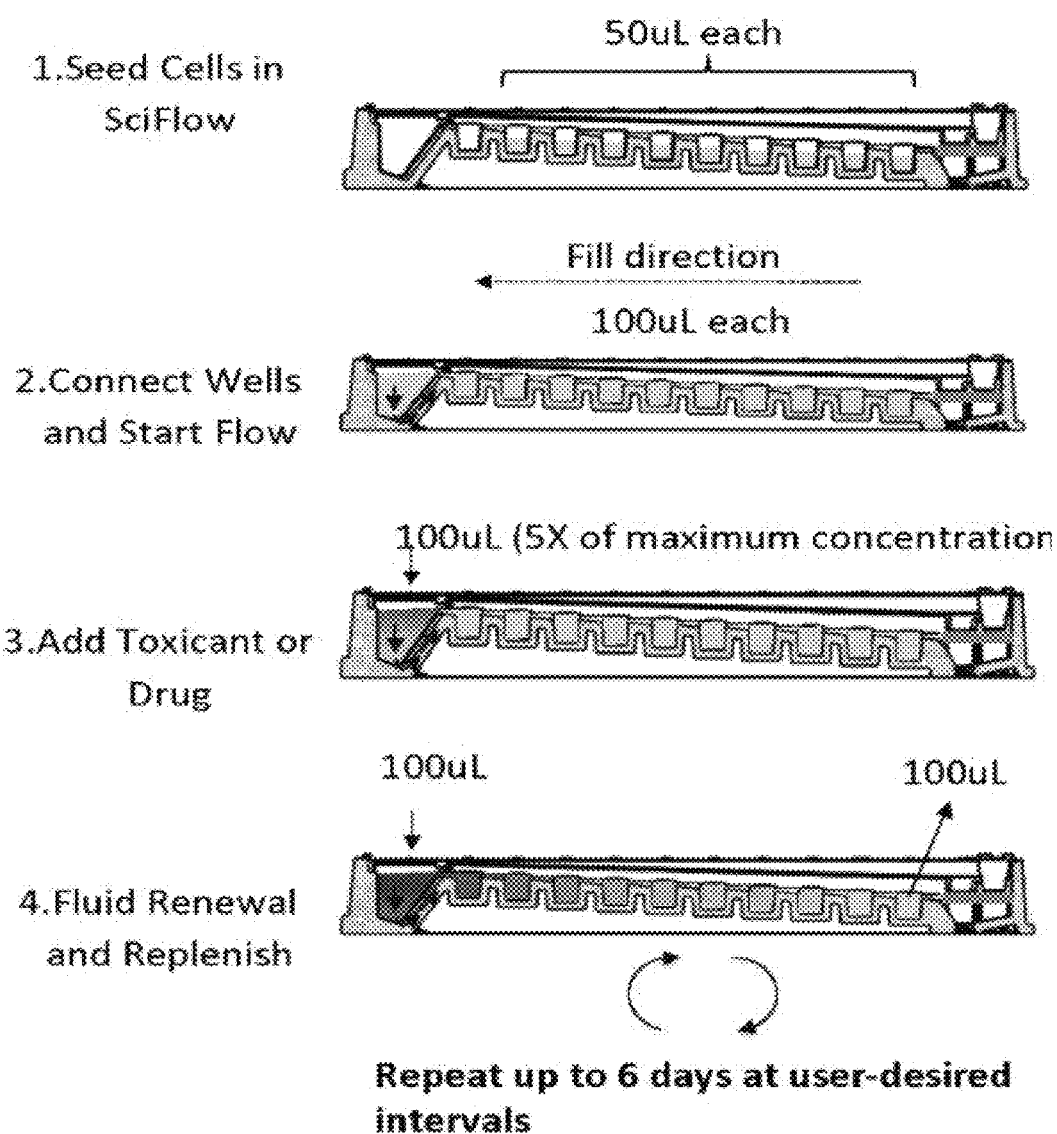
FIG. 30 depicts the use overview of the fluidics device used in EXAMPLE 2.
Figure 31:
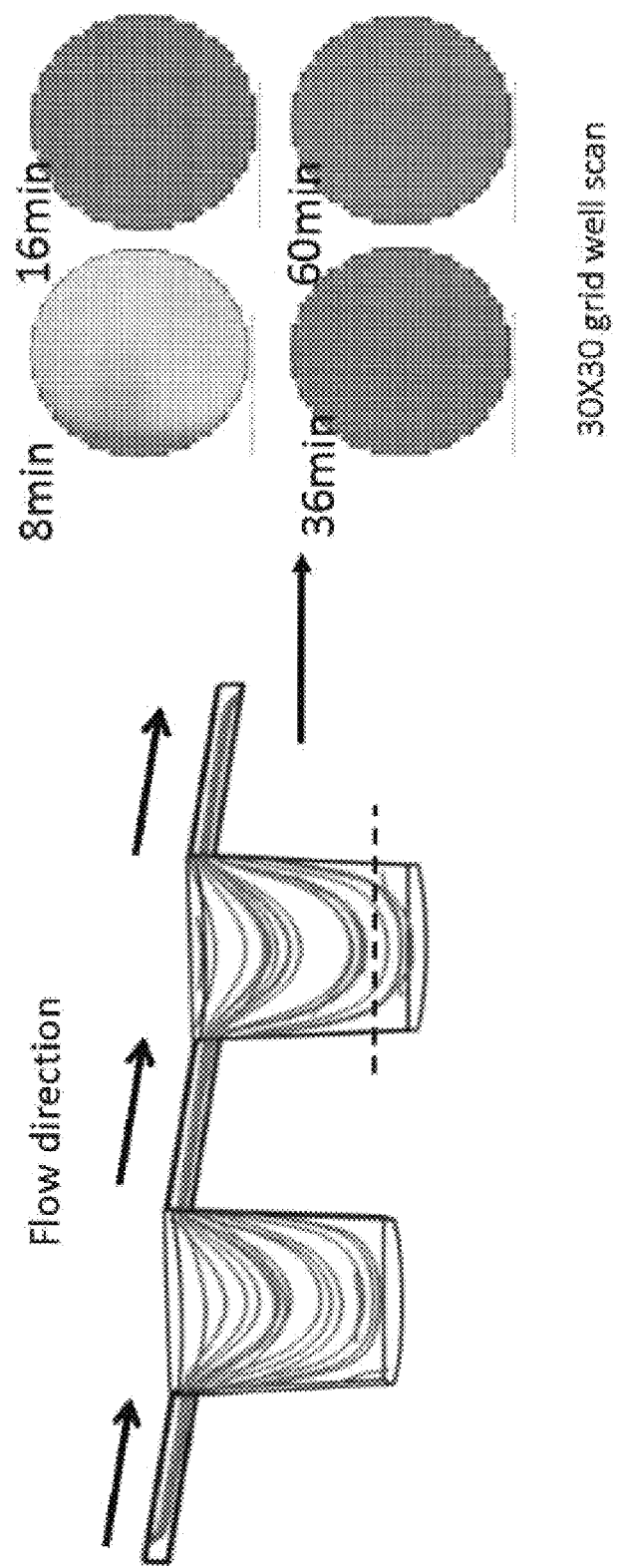
FIG. 31 depicts the fluidics and mixing with the exemplar wells of the fluidics device used in EXAMPLE 2.

Overview of Design of Fluidics Device. See FIGS. 29-31. FIG. 29 depicts the design features of the fluidics device used in EXAMPLE 2. The fluidics device was designed to feature an extra-large source well capable of holding up to 600 uL of media. Each subsequent well of each row is connected together by a microchannel running across the top surface of the plate. A row cover serves to create a closed channel system with open wells to allow full access to both the media and cells in the system. A porous wick at well 12 serves as a sink for excess fluid. FIG. 30 depicts the use overview of the fluidics device used in EXAMPLE 2. The fluidics devices is used to seed cells and tissues, initiate flow, and renew and replenish for long term culturing. FIG. 31 depicts the fluidics and mixing with the exemplar wells of the fluidics device used in EXAMPLE 2. Fluid vector lines showing the direction of fluid moving throughout an individual well. Images acquired using the Wellscan feature of the Clariostar Multimode Reader from BMG LabTech. A 30×30 2D grid was measured for fluorescence intensity at indicated times to measure mixing kinetics. By 60 minutes, the % CV across the grid was less than 2% indicating nearly complete mixing.

Methods. Optimize Z-height focus for measuring fluorescence along rows of the fluidics device. Create Fluorescein standard curve for extrapolating real-time concentration gradients. Determine EC50 for Tamoxifen and APAP induced cell death using HepG2 cells and CellTox™ Green (cytotoxicity reagent).

Results.

See FIGS. 32-37. FIG. 32 is a table showing the determined optimal Z-height focus. Optimal Z-heights were determined by plating HepG2 cells to the wells of the fluidics device in the presence of CellTox™ Green. Cells were then lysed to generate maximum signal. The Tecan Infinite M1000 Pro z-scan settings were used to identify optimal focal height.

Figure 33:
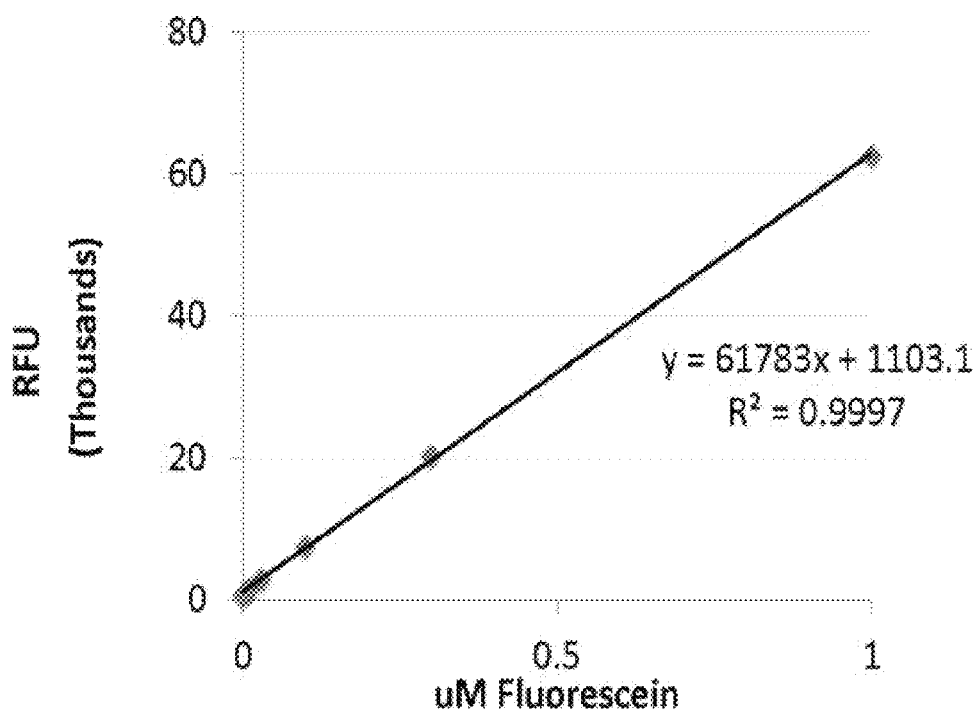
FIG. 33 is a graph plotting the determined Fluorescein standard curve.

FIG. 33 is a graph plotting the determined Fluorescein standard curve. To create the Fluorescein standard curve, each row of the fluidics device was filled with a single concentration from 0.001 uM to 1 uM of Fluorescein dissolved in complete media. Plate was then read at ex485/em525 using the Tecan Infinite M1000 Pro using z-heights in table. The instrument was set to determine optimal gain settings for the 1 uM dilution. The values from each row were averaged and plotted against concentrations resulting in a linear standard curve. The equation for this curve was determined using linear regression analysis. Gain settings were recorded for use in later experiments.

FIG. 34 depicts the experimental plate configuration. Acellular wells were treated exactly the same as cells seeded with 30000 HepG2 cells. After seeding and attachment, media was changed to media containing 1:2000 dilution of CellTox™ Green. Toxicant, Vehicle, or 1 uM Fluorescent tracers was applied to source wells as indicated.

An overview of the data analysis procedure to obtain an EC50 based on AUC exposure is provided. RFU values in rows A and B are converted to [uM] Fluorescein using the standard curve. Calculated uM Fluorescein (XFL) is converted to "Expected" toxicant concentration (XE) by: XE=XFL*Xi: where Xi is the initial toxicant concentration applied to source well in the fluidics device. Area-under-the-curve (AUC) concentrations are calculated by using the linear trapezoidal method for each timepoint. See PKSolver: Computer Methods and Programs in Biomedicine Volume 99, Issue 3, September 2010, Pages 306-314 for further details, which is incorporated herein by reference in its entirety.

Figure 35:
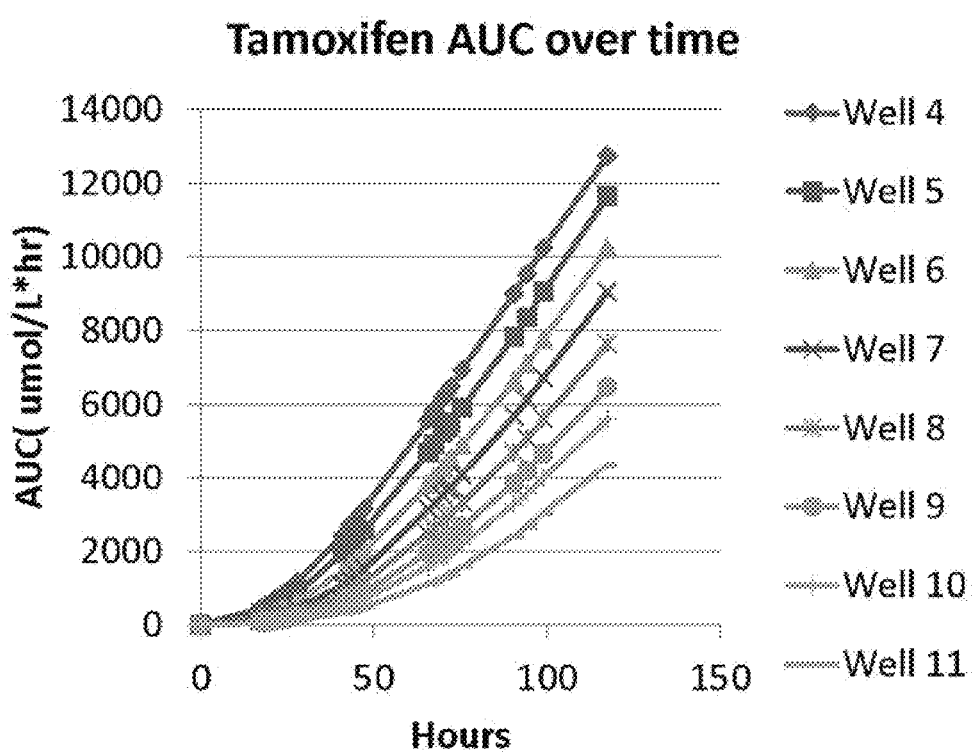
FIG. 35 depicts the effects of Tamoxifen AUC over time.
Figure 36:
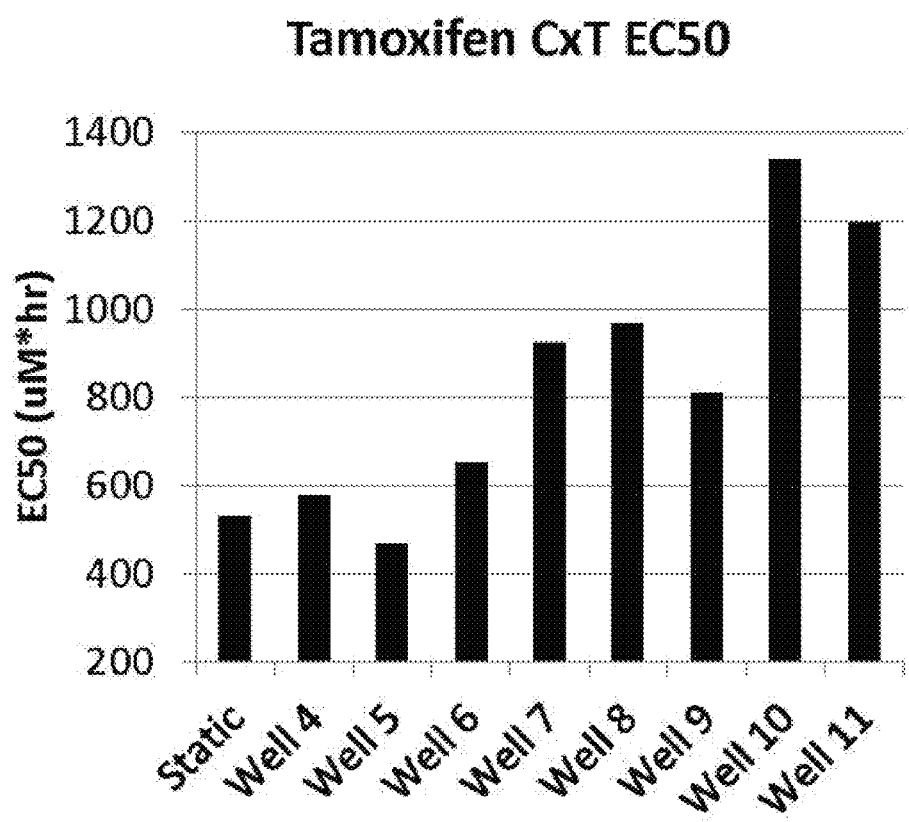
FIG. 36 depicts Tamoxifen concentration multiplied by time EC50s.
Figure 37:
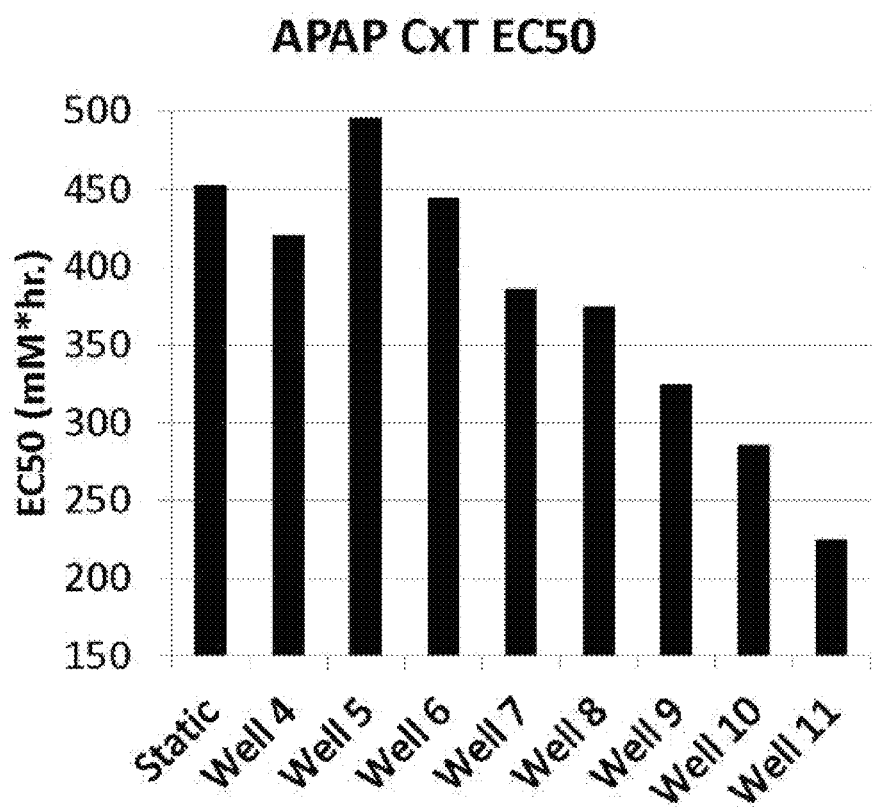
FIG. 37 depicts APA concentration multiplied by time EC50s.

FIGS. 35-37 depict the effects of concentration multiplied by time exposures on EC50s of cytotoxicity. FIG. 35 depicts the effects of Tamoxifen AUC over time. HepG2 cells in the fluidics device were treated with increasing concentrations of Tamoxifen over time. FIG. 36 depicts Tamoxifen concentration multiplied by time EC50s. Calculated EC50 for each well following repeated infusion of Tamoxifen. 150 uM of Tamoxifen was infused into the fluidics device source well three times per day. Two acellular rows were infused with 1 uM Fluorscein to enable calculation of absolute concentration at any given time. The reagent CellTox™ Green was used to monitor cellular toxicity. Area under the curve values for each timepoint were obtained and plotted against effect expressed as a % maximum of (treated/control). EC50 values were calculated by Sigmoid EMax model in PKSolver. FIG. 37 depicts APA concentration multiplied by time EC50s. The calculations were the same as FIG. 36 calculations, except using 50 mM APAP.

Conclusion.

The fluidics device enables generation of robust time-resolved toxicant gradients. Observed EC-50 of Tamoxifen and APAP in downstream wells were different from expected when using standard static culture methods. Tamoxifen observed EC50 suggests deactivation whereas APAP observed EC50s suggest bio-activation of a toxic intermediate consistent with what is known about these toxicants behavior in HepG2 cells.

Figure 38:
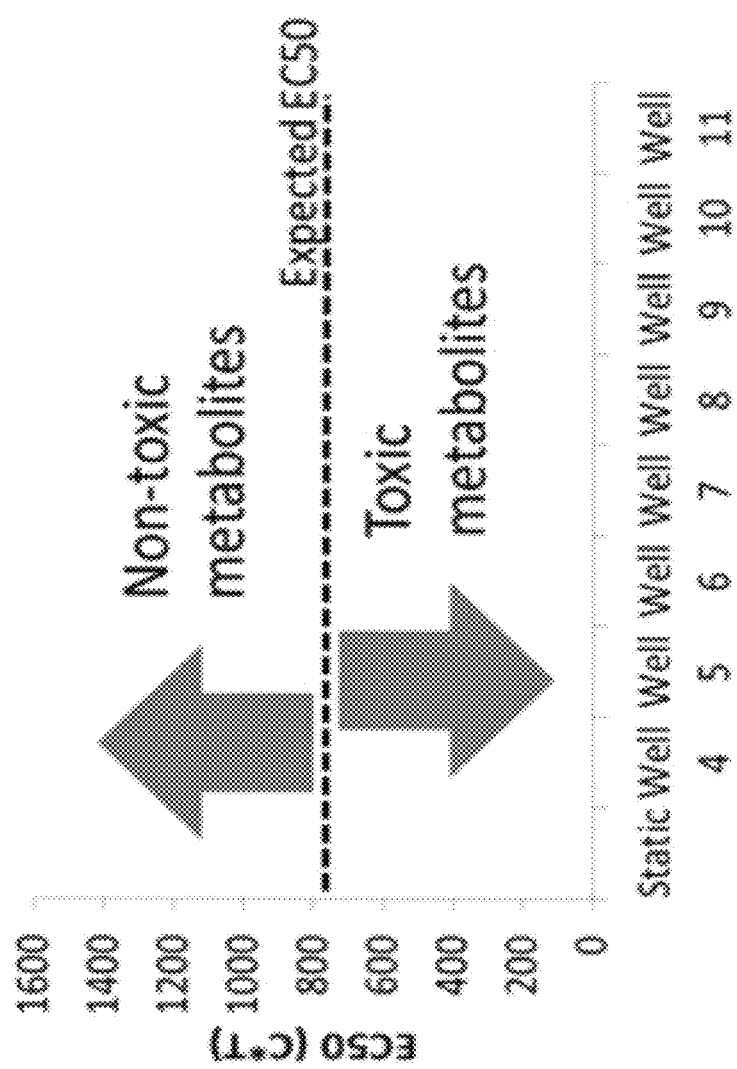
FIG. 38 depicts an embodiment where at least one fluid EC50 is compared to a static EC50.

As the metabolite to parent ratio increases through successive metabolism in each well of the fluidics device, the nature of the EC50 for total parent plus metabolite concentration in each well indicates whether the metabolites being introduced into the system are toxic. Decreasing EC50 with increasing metabolism (e.g. increasing metabolite to parent ratio) indicates the metabolites being produced are less toxic than the parent. Conversely, decreasing EC50 with increasing metabolism indicates the metabolites being produced are more toxic than the parent. By drawing a line where the expected EC50 would be if metabolism had no effect on the outcome, we present the ability to provide a true/false (i.e., Boolean) reflection of the toxicity of metabolites without a-priori knowledge of the structures of those metabolites. Such an approach could be used in hit-to-lead and lead optimization efforts as a way to sort chemicals by whether metabolism has important bioactivity prior to any extensive work to identify, isolate, purify, and test any metabolites (see FIG. 38). FIG. 38 depicts an embodiment where at least one fluid EC50 is compared to a static EC50.

EXAMPLE 3

Figure 46:
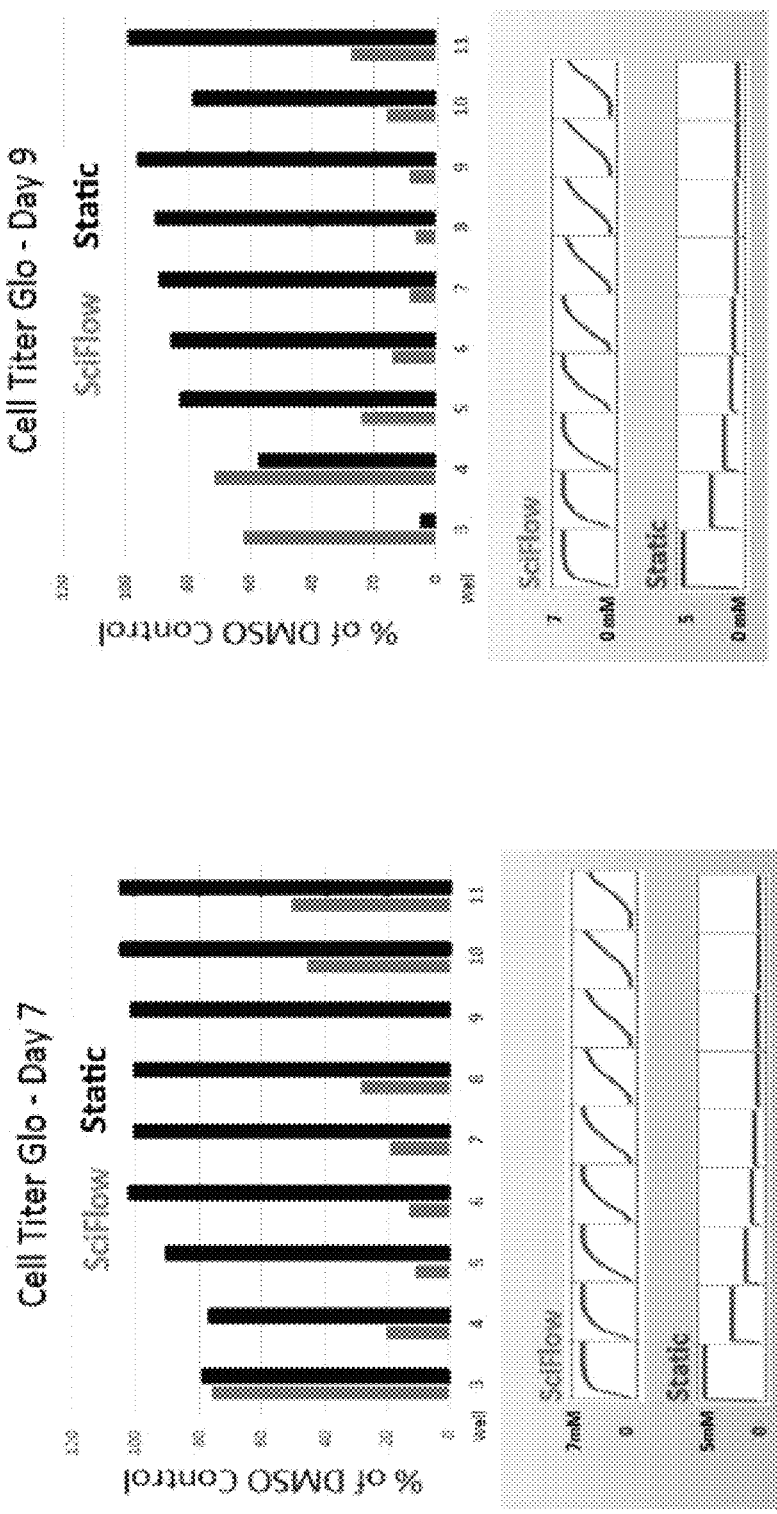
FIG. 46 depicts a comparison of cultured cells treated with acetaminophen over 7 and 9 days in the fluidics device and static plates.

Referring to FIG. 46, a comparison of static plates and fluidics device 100 cultured cells treated with acetaminophen (APAP) over 7 and 9 days is depicted. CellTiter-Glo was used to measure viable cells. Data is normalized to vehicle (DMSO) control. Day 7: toxicity of APAP in static plates (black) is marginally detectable only at highest concentration. The fluidics device 100 (grey) shows a downstream cell death effect which is characteristic of a toxic/reactive metabolite which is produced in the upstream cells and flows downstream. Day 9: obvious cell death in static plate at the highest APAP concentration (5 mM), and marginal effect at 2.5 mM. More pronounced downstream metabolite effect in the fluidics device 100, which provides insights into mechanisms of toxic drug response.

The invention claimed is:

1. An in vitro assay method for determining whether a parameter was diminished or enhanced by a cell culture response to a test compound, comprising:
    applying a dynamic fluid including the test compound to a dynamic dosing well of a fluidics device, wherein the fluidics device includes a plurality of dynamic wells each containing a cell culture therein positioned downstream from the dynamic dosing well and in fluid communication therewith;
    applying a control fluid not including the test compound to a control dosing well of the fluidics device, wherein the fluidics device further includes a plurality of control wells each containing a cell culture therein positioned downstream from the control dosing well and in fluid communication therewith;
    performing a dynamic bioassay to measure the parameter of at least one of the plurality of dynamic wells and determining a dynamic value;
    performing a control bioassay to measure the parameter of at least one of the plurality of control wells and determining a control value;
    comparing the dynamic value to the control value for determining whether the parameter was diminished or enhanced by the cell culture response to the test compound.

2. The method of claim 1, comprising:
    applying a static fluid including the test compound to a static well;
    performing a static bioassay to measure the parameter of the static well and determining a static value;
    comparing the dynamic value to the static value for determining whether the parameter was diminished or enhanced by the cell culture response to the test compound.

3. The method of claim 2, further comprising:
    wherein the dynamic value includes a dynamic effective concentration at a percentage X (ECx) for the parameter, wherein $0 \leq X \leq 100$;
    wherein the static value includes a static ECx for the parameter; and
    wherein a lower value of the at least one dynamic ECx relative to the static ECx is predictive of the cell culture response to the test compound enhancing the parameter and a higher value of the at least one dynamic ECx relative to the static ECx is predictive of the cell culture response to the test compound diminishing the parameter.

4. The method of claim 3, wherein an effect detection reagent is present in the plurality of dynamic wells having a cell culture therein, and wherein determination of the dynamic ECx includes detection of the effect detection reagent.

5. The method of claim 2, further comprising:
removing a portion of the dynamic fluid from at least one stop well, the stop well being one of the plurality of dynamic wells; and
applying a stop to the at least one stop well for controlling the flow of the dynamic fluid in preparation for the dynamic bioassay.

6. The method of claim 2, wherein the performing of any one or more of the bioassays includes removing an aliquot of the respective fluid from the respective well at one or more time periods.

7. The method of claim 2, wherein the applying of the dynamic fluid and/or the control fluid is repeated using a specific volume at determined intervals over a specified period of time.

8. The method of claim 7, wherein the applying of the dynamic fluid and/or the control fluid is performed automatically by a robotic liquid handling apparatus or by using a piston assembly nestably engaged with the fluidics device.

9. The method of claim 7, further comprising syphoning the respective fluid from the downstream well furthest from the respective dosing well when the applying of the dynamic fluid and/or the control fluid is repeated.

10. The method of claim 9, where the syphoning the respective fluid is performed automatically by a robotic liquid handling apparatus.

11. The method of claim 2, further comprising:
applying a tracing fluid having a known concentration of a detectable tracing compound to a tracing dosing well of the fluidics device, wherein the fluidics device further includes a plurality of tracing wells each containing a cell culture therein positioned downstream from the tracing dosing well and in fluid communication therewith;
determining the concentration of the tracing compound as a standard curve to calculate a concentration of the test compound in each of the plurality of dynamic wells.

12. The method of claim 1, further comprising:
wherein the dynamic value includes a dynamic effective concentration at a percentage X (ECx) for the parameter, wherein $0 \leq X \leq 100$;
wherein the control value includes a control ECx for the parameter; and
wherein a lower value of the at least one dynamic ECx relative to the control ECx is predictive of the cell culture response to the test compound enhancing the parameter and a higher value of the at least one dynamic ECx relative to the control ECx is predictive of the cell culture response to the test compound diminishing the parameter.

13. The method of claim 12, wherein an effect detection reagent is present in the plurality of dynamic wells having a cell culture therein, and wherein determination of the dynamic ECx includes detection of the effect detection reagent.

14. The method of claim 1, further comprising:
removing the dynamic fluid, or a portion thereof, from at least one stop well, the stop well being one of the plurality of dynamic wells; and
applying a stop to the at least one stop well for controlling the flow of the dynamic fluid in preparation for the dynamic bioassay.

15. The method of claim 1, wherein the performing of any one or more of the bioassays includes removing an aliquot of the respective fluid from the respective well at one or more time periods.

16. The method of claim 1, wherein the applying of the dynamic fluid and/or the control fluid is repeated using a specific volume at determined intervals over a specified period of time.

17. The method of claim 16, wherein the applying of the dynamic fluid and/or the control fluid is performed automatically by a robotic liquid handling apparatus or by using a piston assembly nestably engaged with the fluidics device.

18. The method of claim 16, further comprising syphoning the respective fluid from the downstream well furthest from the respective dosing well when the applying of the dynamic fluid and/or the control fluid is repeated.

19. The method of claim 18, where the syphoning the respective fluid is performed automatically by a robotic liquid handling apparatus.

20. The method of claim 1, further comprising:
applying a tracing fluid having a known concentration of a detectable tracing compound to a tracing dosing well of the fluidics device, wherein the fluidics device further includes a plurality of tracing wells each containing a cell culture therein positioned downstream from the tracing dosing well and in fluid communication therewith;
determining the concentration of the tracing compound as a standard curve to calculate a concentration of the test compound in each of the plurality of dynamic wells.

* * * * *